United States Patent
Ismagilov et al.

(10) Patent No.: US 9,803,237 B2
(45) Date of Patent: Oct. 31, 2017

(54) SLIP-INDUCED COMPARTMENTALIZATION

(71) Applicants: California Institute of Technology, Pasadena, CA (US); SlipChip Corporation, Pasadena, CA (US)

(72) Inventors: Rustem F. Ismagilov, Altadena, CA (US); Feng Shen, Pasadena, CA (US)

(73) Assignees: California Institute of Technology, Pasadena, CA (US); SlipChip Corporation, Chicago, IL (US)

(*) Notice: Subject to any disclaimer, the term of this patent is extended or adjusted under 35 U.S.C. 154(b) by 1226 days.

(21) Appl. No.: 13/869,856

(22) Filed: Apr. 24, 2013

(65) Prior Publication Data

US 2013/0281316 A1    Oct. 24, 2013

Related U.S. Application Data

(60) Provisional application No. 61/637,661, filed on Apr. 24, 2012.

(51) Int. Cl.
  *C12Q 1/68* (2006.01)
  *B01L 3/00* (2006.01)
  *B01L 7/00* (2006.01)

(52) U.S. Cl.
  CPC ........ *C12Q 1/686* (2013.01); *B01L 3/502738* (2013.01); *B01L 7/52* (2013.01); *B01L 2200/0668* (2013.01); *B01L 2200/0673* (2013.01); *B01L 2300/069* (2013.01); *B01L 2300/0681* (2013.01); *B01L 2300/0864* (2013.01); *B01L 2300/0867* (2013.01); *B01L 2300/161* (2013.01);

(Continued)

(58) Field of Classification Search
  CPC ............... B01L 3/502738; B01L 7/52; B01L 2200/668; B01L 2400/65
  See application file for complete search history.

(56) References Cited

U.S. PATENT DOCUMENTS

| 2,541,413 A | 2/1951 | Gorey |
| 5,026,113 A | 6/1991 | Dicarlo et al. |
| 5,114,208 A | 5/1992 | Ikeda et al. |

(Continued)

FOREIGN PATENT DOCUMENTS

| EP | 1110084 B1 | 7/1999 |
| WO | WO 99/29703 A2 | 6/1999 |

(Continued)

OTHER PUBLICATIONS

Abrams, et al. "Development of a microfluidic device for detection of pathogens in oral samples using upconverting phosphor technology (UPT)." Annals of the New York Academy of Sciences. 2007, 1098.1: 375-388.

(Continued)

*Primary Examiner* — Sam P Siefke
(74) *Attorney, Agent, or Firm* — Fenwick & West LLP

(57) ABSTRACT

The present invention relates to fluidic devices for compartmentalizing samples. In particular, the devices and related systems and methods allow for compartmentalization by using one or more first chambers connect by a first channel (e.g., where the cross-sectional dimension of the first channel is less than the cross-sectional dimension of at least one first chamber).

32 Claims, 16 Drawing Sheets

(52) U.S. Cl.
CPC ............... B01L 2400/0409 (2013.01); B01L 2400/0487 (2013.01); B01L 2400/065 (2013.01)

(56) References Cited

U.S. PATENT DOCUMENTS

| | | | |
|---|---|---|---|
| 5,234,809 A | 8/1993 | Boom et al. | |
| 5,582,988 A | 12/1996 | Backus et al. | |
| 5,658,548 A | 8/1997 | Padhye et al. | |
| 5,688,651 A | 11/1997 | Solomon | |
| 5,705,628 A | 1/1998 | Hawkins | |
| 5,805,947 A | 9/1998 | Miyamoto et al. | |
| 5,808,041 A | 9/1998 | Padhye et al. | |
| 6,162,356 A | 12/2000 | Ikeda et al. | |
| 6,300,138 B1 | 10/2001 | Gleason et al. | |
| 6,426,230 B1 | 7/2002 | Feistel | |
| 6,645,717 B1 | 11/2003 | Smith et al. | |
| 6,718,742 B1 | 4/2004 | Baker | |
| 6,914,137 B2 | 7/2005 | Baker | |
| 6,949,575 B2 | 9/2005 | Barta et al. | |
| 7,003,104 B2 | 2/2006 | Lee | |
| 7,129,091 B2 | 10/2006 | Ismagilov et al. | |
| 7,319,004 B2 | 1/2008 | Harper et al. | |
| 7,329,485 B2 | 2/2008 | Zlotnick | |
| 7,375,190 B2 | 5/2008 | Cheng et al. | |
| 7,429,470 B2 | 9/2008 | Lee et al. | |
| 7,601,497 B2 | 10/2009 | Nazarenko et al. | |
| 7,629,165 B2 | 12/2009 | Wyatt et al. | |
| 7,655,470 B2 | 2/2010 | Ismagilov et al. | |
| 7,718,262 B2 | 5/2010 | Chandler et al. | |
| 7,767,447 B2 | 8/2010 | Breidenthal et al. | |
| 7,780,336 B2 | 8/2010 | Breidenthal et al. | |
| 7,871,813 B2 | 1/2011 | Wyatt et al. | |
| 7,901,939 B2 | 3/2011 | Ismagilov et al. | |
| 7,955,801 B2 | 6/2011 | Lee et al. | |
| 8,052,929 B2 | 11/2011 | Breidenthal et al. | |
| 8,211,367 B2 | 7/2012 | Wyatt et al. | |
| 8,247,176 B2 | 8/2012 | Peterson et al. | |
| 8,273,573 B2 | 9/2012 | Ismagilov et al. | |
| 8,283,037 B2 | 10/2012 | Chandler et al. | |
| 8,304,193 B2 | 11/2012 | Ismagilov et al. | |
| 8,323,899 B2 | 12/2012 | Sherman et al. | |
| 8,329,407 B2 | 12/2012 | Ismagilov et al. | |
| 8,480,976 B2 | 7/2013 | Breidenthal et al. | |
| 8,491,178 B2 | 7/2013 | Breidenthal et al. | |
| 8,574,833 B2 | 11/2013 | Jenison et al. | |
| 8,615,368 B2 | 12/2013 | Light, II et al. | |
| 8,637,250 B2 | 1/2014 | Jenison | |
| 8,784,745 B2 | 7/2014 | Nelson et al. | |
| 2003/0008320 A1 | 1/2003 | Baker | |
| 2003/0022243 A1 | 1/2003 | Kondejewski et al. | |
| 2003/0054395 A1 | 3/2003 | Baker | |
| 2003/0130499 A1 | 7/2003 | Baker | |
| 2003/0173284 A1 | 9/2003 | Baker | |
| 2004/0119070 A1* | 6/2004 | Roach ............... B01L 3/502715 257/48 | |
| 2005/0003399 A1 | 1/2005 | Blackburn et al. | |
| 2005/0009582 A1 | 1/2005 | Vooi-kia et al. | |
| 2005/0019792 A1 | 1/2005 | Mcbride et al. | |
| 2005/0053941 A1 | 3/2005 | Baker et al. | |
| 2005/0087122 A1 | 4/2005 | Ismagilov et al. | |
| 2005/0142565 A1 | 6/2005 | Samper et al. | |
| 2005/0172476 A1 | 8/2005 | Stone et al. | |
| 2005/0221339 A1 | 10/2005 | Griffiths et al. | |
| 2006/0003439 A1 | 1/2006 | Ismagilov et al. | |
| 2006/0024712 A1 | 2/2006 | Baker et al. | |
| 2006/0078888 A1 | 4/2006 | Griffiths et al. | |
| 2006/0078893 A1 | 4/2006 | Griffiths et al. | |
| 2006/0094051 A1 | 5/2006 | Lee et al. | |
| 2006/0110725 A1 | 5/2006 | Lee et al. | |
| 2006/0154247 A1 | 7/2006 | Baker et al. | |
| 2006/0159962 A1 | 7/2006 | Chandler et al. | |
| 2006/0163385 A1 | 7/2006 | Link et al. | |
| 2006/0263780 A1 | 11/2006 | Baker et al. | |
| 2007/0003442 A1 | 1/2007 | Link et al. | |
| 2007/0015188 A1 | 1/2007 | Luo et al. | |
| 2007/0052781 A1 | 3/2007 | Fraden et al. | |
| 2007/0092914 A1 | 4/2007 | Griffiths et al. | |
| 2007/0122809 A1 | 5/2007 | Stevenson et al. | |
| 2007/0155451 A1 | 7/2007 | Lee | |
| 2007/0172954 A1 | 7/2007 | Ismagilov et al. | |
| 2007/0184489 A1 | 8/2007 | Griffiths et al. | |
| 2007/0195127 A1 | 8/2007 | Ahn et al. | |
| 2007/0221563 A1 | 9/2007 | Sakaino et al. | |
| 2007/0238114 A1 | 10/2007 | Lee et al. | |
| 2008/0003142 A1 | 1/2008 | Link et al. | |
| 2008/0003693 A1 | 1/2008 | Torres | |
| 2008/0014589 A1 | 1/2008 | Link et al. | |
| 2008/0038725 A1 | 2/2008 | Luo et al. | |
| 2008/0058039 A1 | 3/2008 | Lee et al. | |
| 2008/0132694 A1 | 6/2008 | Himmelreich et al. | |
| 2008/0161553 A1 | 7/2008 | Ohnishi et al. | |
| 2008/0166703 A1 | 7/2008 | Himmelreich et al. | |
| 2008/0166793 A1 | 7/2008 | Beer et al. | |
| 2008/0318279 A1 | 12/2008 | Lee et al. | |
| 2009/0021728 A1 | 1/2009 | Heinz et al. | |
| 2009/0215050 A1 | 8/2009 | Jenison | |
| 2009/0221096 A1 | 9/2009 | Torres | |
| 2010/0036104 A1 | 2/2010 | Nazarenko et al. | |
| 2010/0078077 A1 | 4/2010 | Ismagilov et al. | |
| 2010/0178709 A1 | 7/2010 | Chandler et al. | |
| 2010/0190240 A1 | 7/2010 | Jiang et al. | |
| 2010/0233026 A1 | 9/2010 | Ismagilov et al. | |
| 2010/0285578 A1 | 11/2010 | Selden et al. | |
| 2010/0304387 A1 | 12/2010 | Jenison et al. | |
| 2011/0059442 A1 | 3/2011 | Luo et al. | |
| 2011/0059866 A1 | 3/2011 | Luo et al. | |
| 2011/0112503 A1 | 5/2011 | Ismagilov et al. | |
| 2011/0142734 A1 | 6/2011 | Ismagilov et al. | |
| 2011/0165037 A1 | 7/2011 | Ismagilov et al. | |
| 2011/0176966 A1 | 7/2011 | Ismagilov et al. | |
| 2011/0177586 A1 | 7/2011 | Ismagilov et al. | |
| 2011/0177588 A1 | 7/2011 | Lee et al. | |
| 2011/0183325 A1 | 7/2011 | Lee et al. | |
| 2011/0318728 A1 | 12/2011 | Phan et al. | |
| 2012/0028342 A1* | 2/2012 | Ismagilov ......... B01L 3/502738 435/283.1 | |
| 2012/0077188 A1 | 3/2012 | Nelson et al. | |
| 2012/0196944 A1 | 8/2012 | Baker | |
| 2012/0197009 A1 | 8/2012 | Baker | |
| 2012/0214168 A1 | 8/2012 | Young et al. | |
| 2012/0264132 A1 | 10/2012 | Ismagilov et al. | |
| 2012/0329171 A1 | 12/2012 | Ismagilov et al. | |
| 2013/0030163 A1 | 1/2013 | Fabis et al. | |
| 2013/0101995 A1 | 4/2013 | Rustem et al. | |
| 2013/0130226 A1 | 5/2013 | Lim et al. | |
| 2013/0280725 A1 | 10/2013 | Ismagilov et al. | |
| 2013/0288348 A1 | 10/2013 | Breidenthal et al. | |
| 2013/0309679 A1 | 11/2013 | Ismagilov et al. | |
| 2013/0331298 A1 | 12/2013 | Rea | |
| 2014/0017730 A1 | 1/2014 | Hicke et al. | |
| 2014/0038200 A1 | 2/2014 | Jenison et al. | |
| 2014/0134619 A1 | 5/2014 | Jenison | |

FOREIGN PATENT DOCUMENTS

| | | |
|---|---|---|
| WO | WO 00/13014 | 3/2000 |
| WO | WO 01/03149 A1 | 1/2001 |
| WO | WO 01/88185 A2 | 11/2001 |
| WO | WO 02/48164 A2 | 6/2002 |
| WO | WO 03/046177 A1 | 6/2003 |
| WO | WO 03/097831 A1 | 11/2003 |
| WO | WO 03/101494 A1 | 12/2003 |
| WO | WO 2004/038363 A2 | 5/2004 |
| WO | WO 2005/012521 A1 | 2/2005 |
| WO | WO 2006/004611 A2 | 1/2006 |
| WO | WO 2006/096571 A2 | 9/2006 |
| WO | WO 2006/101851 A2 | 9/2006 |
| WO | WO 2007/030501 A2 | 3/2007 |
| WO | WO 2007/070832 | 6/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/089541 A2 | 8/2007 |

(56) References Cited

FOREIGN PATENT DOCUMENTS

| | | |
|---|---|---|
| WO | WO 2007/089777 A2 | 8/2007 |
| WO | WO 2007/133710 A2 | 11/2007 |
| WO | WO 2007/146923 | 12/2007 |
| WO | WO 2008/063227 A2 | 5/2008 |
| WO | WO 2008/069884 A2 | 6/2008 |
| WO | WO 2008/079274 A1 | 7/2008 |
| WO | WO 2009/015390 A2 | 1/2009 |
| WO | WO 2009/048673 A2 | 4/2009 |
| WO | WO 2009/070640 | 6/2009 |
| WO | WO 2009/070742 | 6/2009 |
| WO | WO 2009/105648 | 8/2009 |
| WO | WO 2009/149257 A1 | 12/2009 |
| WO | WO 2010/078420 | 7/2010 |
| WO | WO 2010/111265 * | 9/2010 |
| WO | WO 2010/111265 A1 | 9/2010 |
| WO | WO 2011/109762 | 9/2011 |
| WO | WO 2013/123238 | 8/2013 |

OTHER PUBLICATIONS

Bellisario, et al. Simultaneous measurement of thyroxin and thyrotropin from newborn dried blood-spot specimens using a multiplexed fluorescent microsphere immunoassay. Clin Chem. 2000, 46:1422-1424.
Boom, et al. "Rapid and simple method for purification of nucleic acids." Journal of clinical microbiology. 1990, 28.3: 495-503.
Cady, Nathaniel C., et al. "A microchip-based DNA purification and real-time PCR biosensor for bacterial detection." Sensors, Proceedings of IEEE. Oct. 24-27, 2004, 3:1191-1194. DOI: 10.1109/ICSENS.2004.1426391.
Cassol, et al. "Use of dried blood spot specimens in the detection of human immunodeficiency virus type 1 by the polymerase chain reaction." Journal of clinical microbiology. 1991, 29.4: 667-671.
Chu, et al. "A nanoporous silicon membrane electrode assembly for on-chip micro fuel cell applications." Microelectromechanical Systems Journal. 2006, 15.3: 671-677.
Cohen, et al. "Microfabrication of silicon-based nanoporous particulates for medical applications." Biomedical Microdevices, 2003. 5.3: 253-259.
De Jesus, et al. Development and evaluation of quality control dried blood spot materials in newborn screening for lysosomal storage disorders. Clin Chem. 2009. 55:158-164.
De Jong, et al. "New replication technique for the fabrication of thin polymeric microfluidic devices with tunable porosity." Lab on a Chip. 2005, 5.11: 1240-1247.
Desai, et al. "Nanoporous anti-fouling silicon membranes for biosensor applications." Biosensors & Bioelectronics. 2000, 15: 453-462.
Du, et al. "High-throughput nanoliter sample introduction microfluidic chip-based flow injection analysis system with gravity-driven flows." *Analytical chemistry*. 2005, 77.5: 1330-1337.
Fukaya, et al. "Evaluation of a series of imidazolium based ionic liquids as solvents for nucleic acids". AE1—Fourteenth International Symposium on Molten Salts Joint International Meeting, Oct. 3-Oct. 8, 2004. Abstract 2437.
Great Basin Corporation. Isothermal Amplification. Available at www.gbscience.com/technology/iso-amp. Accessed Jan. 6, 2014.
Great Basin Corporation. Sample-to-Result Molecular Diagnostics. Available at www.gbscience.com. Accessed Jan. 6, 2014.
Great Basin Corporation. Technology—Early appropriate treatment of infections is critical for good patient outcomes and to manage treatment costs. Available at www.gbscience.com/technology. Access Jan. 6, 2014.
Gulliksen, et al. "Parallel nanoliter detection of cancer markers using polymer microchips." Lab on a Chip. 2005, 5.4: 416-420.
Hong, et al. "A nanoliter-scale nucleic acid processor with parallel architecture." Nature biotechnology. 2004, 22.4: 435-439.
Huang, et al. "Counting low-copy number proteins in a single cell." Science. 2007, 315.5808: 81-84.

Kaigala, et al. "Automated screening using microfluidic chip-based PCR and product detection to assess risk of BK virus-associated nephropathy in renal transplant recipients." Electrophoresis. 2006, 27.19: 3753-3763.
Koh, et al. "Integrating polymerase chain reaction, valving, and electrophoresis in a plastic device for bacterial detection." Analytical Chemistry. 2013, 75.17: 4591-4598.
Lapizco-Encinas, et al. "An insulator-based (electrodeless) dielectrophoretic concentrator for microbes in water." Journal of microbiological methods. 2005, 62.3: 317-326.
Leamon, et al. "Overview: methods and applications for droplet compartmentalization of biology." Nature methods. 2006, 3.7: 541-543.
Li, et al. "Dried blood spot sampling in combination with LC-MS/MS for quantitative analysis of small molecules." Biomedical Chromatography. 2010. 24.1: 49-65.
Liu, et al. "A nanoliter rotary device for polymerase chain reaction." Electrophoresis. 2002, 23 (2002): 1531-1536.
Macek, et al. "Papers, ready-for-use plates, and flexible sheets for chromotography." Chromatographic Reviews. 1971, vol. 15, No. 1, pp. 1-28 DOI: 10.1016/0009-5907(71)80007-8.
Martinez, Andres W., et al. "Simple telemedicine for developing regions: camera phones and paper-based microfluidic devices for real-time, off-site diagnosis." Analytical Chemistry. 2008, 80.10: 3699-3707.
Martinez, et al. "FLASH: a rapid method for prototyping paper-based microfluidic devices." Lab on a Chip. 2008, 8.12: 2146-2150.
Martinez, et al. "Patterned paper as a platform for inexpensive, low-volume, portable bioassays." Angewandte Chemie International Edition. 2007, 46.8: 1318-1320.
Matsubara, et al. "Microchamber array based DNA quantification and specific sequence detection from a single copy via PCR in nanoliter volumes." Biosensors and Bioelectronics. 2005, 20.8: 1482-1490.
McDade, et al. "What a drop can do: dried blood spots as a minimally invasive method for integrating biomarkers into population-based research." Demography. 2007. 44.4: 899-925.
Merlin, et al. "Microfluidic-assisted growth of colloidal crystals." Soft Matter. 2012, 8.13: 3526-3537.
Ohji, Hiroshi, Sami Lahteenmaki, and Patrick J. French. "Macroporous silicon formation for micromachining." Micromachining and Microfabrication. International Society for Optics and Photonics, 1997. 189-197.
Ottesen, et al. "Microfluidic digital PCR enables multigene analysis of individual environmental bacteria." Science. 200, 314.5804: 1464-1467.
Parker SP, Cubitt WD. The use of the dried blood spot sample in epidemiological studies. J Clin Pathol. 1999. 52:633-639.
Petronis, et al. "Model porous surfaces for systematic studies of material-cell interactions." Journal of Biomedical Materials. 2003, Research Part A 66.3: 707-721.
Pichonat, et al. "Development of porous silicon-based miniature fuel cells." Micromech. Microeng. 2005, 15.9: S179-S184 doi:10.1088/0960-1317/15/9/S02.
Randall GC, Doyle PS. Permeation-driven flow in poly(dimethylsiloxane) microfluidic devices. Proc. Natl. Acad. Sci. 2005, 102:10813-10818.
Rea, et al. Point-of-Care Molecular Diagnostic Testing. Created Dec. 12, 2012 20:17. Published: Dec. 12, 2012. Published on IVD Technology. Available at http://www.ivdtechnology.com/print/3097. Accessed Jan. 6, 2014.
Shen, Feng, et al. "Nanoliter multiplex PCR arrays on a SlipChip." Analytical chemistry. 2010, 82.11: 4606-4612.
Shi, et al. "Ionic liquids promote PCR amplification of DNA." Chemical Communications . 2012, 48.43: 5325-5327.
Tuteja, Anish, et al. "Design parameters for superhydrophobicity and superoleophobicity." MRS bulletin. 2008, 33.08: 752-758.
Vozzi, et al. "Fabrication of PLGA scaffolds using soft lithography and microsyringe deposition." Biomaterials. 2003, 24: 2533-2540.
Wang, et al. "Direct extraction of double-stranded DNA into ionic liquid 1-butyl-3-methylimidazolium hexafluorophosphate and its quantification." Analytical chemistry 79.2 (2007): 620-625.

(56) References Cited

OTHER PUBLICATIONS

Wang, et al. "Palladium-silver thin film for hydrogen sensing." Sensors and Actuators B: Chemical. 2007, 123.1: 101-106.
Williams, et al. "The use of dried blood spot sampling in the National Social Life, Health, and Aging Project." The Journals of Gerontology Series B: Psychological Sciences and Social Sciences. 2009. 64.suppl 1: i131-i136.
Wong, et al. "Electrokinetic bioprocessor for concentrating cells and molecules." Analytical chemistry. 2004, 76.23: 6908-6914.
Yang, et al. "High sensitivity PCR assay in plastic micro reactors." Lab on a Chip. 2002, 2.4: 179-187.

* cited by examiner

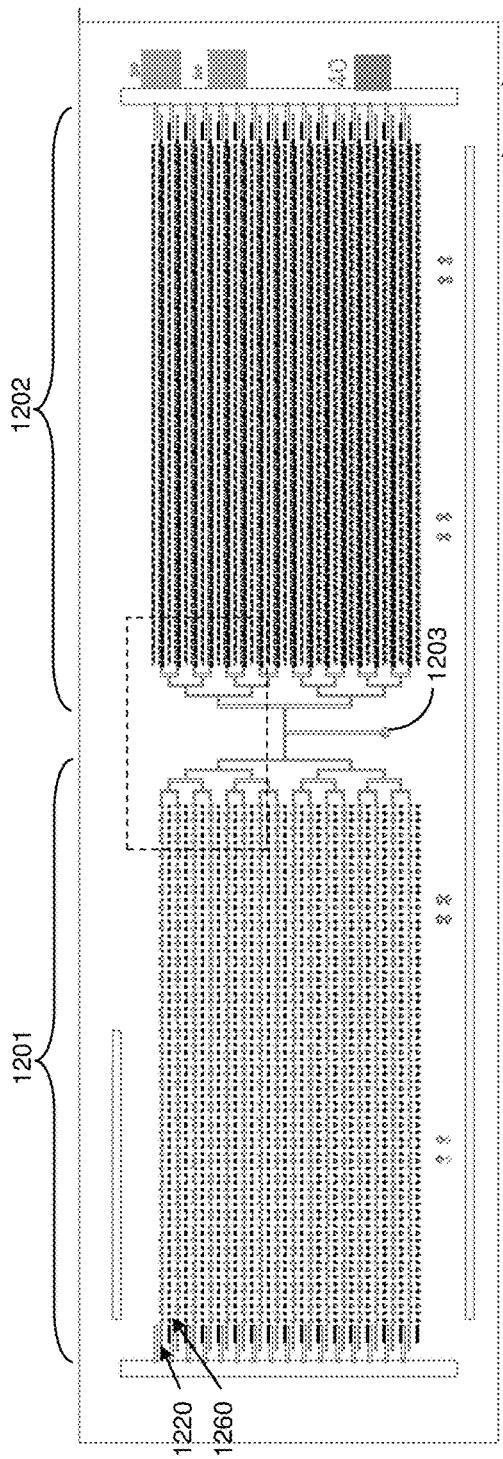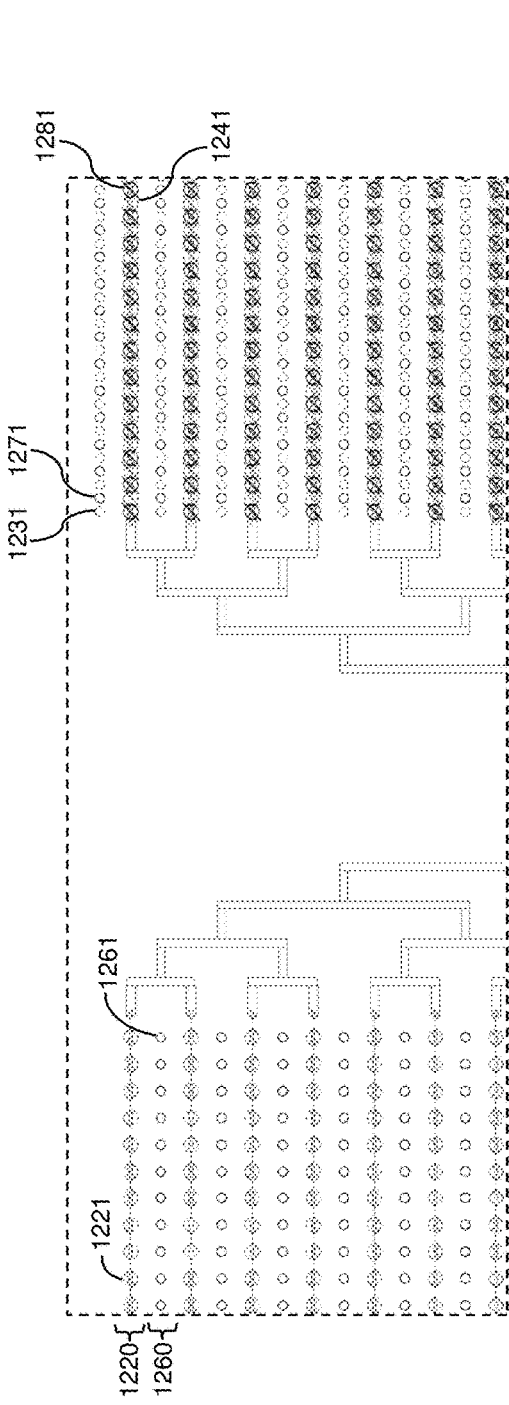
Figure 12A
Figure 12B

SLIP-INDUCED COMPARTMENTALIZATION

CROSS REFERENCE TO RELATED APPLICATION

This application claims benefit of U.S. Provisional Application No. 61/637,661, filed on Apr. 24, 2012, which is hereby incorporated by reference in its entirety.

STATEMENT REGARDING FEDERALLY SPONSORED RESEARCH

This invention was made with government support under Grant No. HR0011-11-2-0006 awarded by the Defense Advanced Research Projects Agency and under Grant No. HG006081 awarded by the National Institutes of Health. The government has certain rights in the invention.

BACKGROUND OF THE INVENTION

The present invention relates to fluidic devices for compartmentalizing samples. In particular, such devices allow for multiple reactions to be performed while minimizing contamination.

Fluidic devices and systems are useful for conducting various types of reactions, diagnostics, and assays while minimizing sample volumes, such as by compartmentalizing a sample into small volumes. Such devices and systems are useful for various types of assays, such as digital nucleic acid amplification, single molecule analysis, and multiplex reactions. Traditional methods for generation of compartments require complex control systems, such as a fluidic pump, one or valves, a centrifuge, etc. Accordingly, there is a need for simplified fluidic devices and systems capable of manipulating and generating small sample volumes while allowing for quantitative, multiplexed, and/or ultrasensitive diagnostics for various applications, including detection of nucleic acids or proteins.

SUMMARY OF THE INVENTION

The invention provides a fluidic device for compartmentalizing samples and methods of use thereof.

The invention features a device (e.g., a microfluidic device) for compartmentalization including: a first layer including a first region; and a second layer including a plurality of second regions; where the first region and the plurality of second regions are connected by relative movement of the first and second layers to form a plurality of combined regions, where, when a target fluid is present in the first layer, the relative movement results in separation of the target fluid into compartments that are separated by an immiscible fluid and located in the plurality of combined regions, and where the device, the target fluid, and the immiscible fluid form a system, and the surface energy of the system is reduced by the separation of the target fluid into compartments.

In some embodiments, the first region includes a first channel, and the second regions may be contained within a continuous channel or be discrete chambers. For example, the plurality of second regions includes a plurality of chambers, a plurality of hydrophilic surfaces, or a plurality of hydrophobic surfaces. In further embodiments, the device includes an array of the first channels (or a serpentine channel) and/or an array of the plurality of second regions.

In other embodiments, the plurality of second regions includes the plurality of hydrophilic surfaces, and the second layer further includes a plurality of hydrophobic surfaces alternating with and fluidically connected to the plurality of hydrophilic surfaces.

In some embodiments, the first region is one of a plurality of fluidically connected first regions, and the plurality of second regions includes a plurality of chambers, a plurality of hydrophilic surfaces, or a plurality of hydrophobic surfaces. In further embodiments, the device includes an array of the plurality of first regions and/or an array of the plurality of second regions. When a plurality of first regions is present, the regions may be contained in a channel with constant cross-section, or the first regions may be sections in a channel not having a constant cross-section.

In some embodiments, the plurality of first regions includes the plurality of hydrophilic surfaces, and the plurality of second regions includes a plurality of hydrophilic surfaces, where the hydrophilic surfaces of the plurality of first and second regions alternate with hydrophobic surfaces. In other embodiments, the plurality of first regions includes the plurality of hydrophobic surfaces, and the plurality of second regions includes a plurality of hydrophobic surfaces, where the hydrophobic surfaces of the plurality of first and second regions alternate with hydrophilic surfaces.

In some embodiments, the first layer further includes a plurality of third regions alternating with the plurality of first regions. In further embodiments, the plurality of first regions includes chambers, and the plurality of third regions includes channels connecting the chambers, where a cross-sectional dimension of the channel is less than a cross-sectional dimension of the chambers.

In some embodiments, the plurality of second regions includes chambers. In further embodiments, the second layer further includes a plurality of fourth regions, which are chambers alternating with and not fluidically connected to the plurality of second regions, where the third and fourth regions are connected by the relative movement. Alternatively, the fourth regions are hydrophobic surfaces (e.g., when the target fluid is hydrophilic) or hydrophilic (e.g., when the target fluid is hydrophobic). In some embodiments, the plurality of second regions includes hydrophilic or hydrophobic surfaces, and the second layer includes alternating hydrophobic and hydrophilic surfaces.

In other embodiments, the second layer further includes a plurality of fifth regions that are not fluidically connected with the plurality of second regions, where a second relative movement of the first or second layers connects the compartments with the fifth regions. In further embodiments, the fifth regions are fluidically connected. In some embodiments, the fifth regions contain a reagent fluid. In further embodiments, the second relative movement results in separation of the reagent fluid and mixture with the compartments. In some embodiments, the first region is connected to one of the plurality of second regions and one of the plurality of fifth regions after the second relative movement.

In some embodiments, the first layer includes a sixth region that is not fluidically connected to the first region, and the compartments are located in the second layer, where a second relative movement of the first or second layer connects the compartments with the sixth region. In further embodiments, the sixth region contains a reagent fluid. In other embodiments, the second relative movement results in separation of the reagent fluid and mixture with the compartments.

In some embodiments, the first layer further includes a first plurality of chambers that are not fluidically connected to each other or to the first region, and the second layer further includes a second plurality of chambers that are not connected to each other or the plurality of second regions, where, prior to the relative movement, the first region is fluidically connected to the second plurality of chambers, the relative movement results in connecting of the first plurality of chambers to the second plurality of chambers to form a second plurality of combined regions, and results in further separation of the target fluid into second compartments that are separated by an immiscible fluid and located in the second plurality of combined regions.

In some embodiments, the immiscible fluid is a liquid lubricant (e.g., any described herein). In other embodiments, the target fluid includes an aqueous fluid (e.g., any described herein). In yet other embodiments, the plurality of second regions contains the immiscible fluid. In some embodiments, the plurality of second regions including a binding agent (e.g., any described herein, such as those selected from an antibody, an antibody fragment, an oligopeptide, a polypeptide, a nucleic acid, a cellular receptor, a ligand, an aptamer, a MHC-peptide monomer or oligomer, biotin, avidin, an oligonucleotide, a coordination complex, a synthetic polymer, a carbohydrate, a charged surface, a modified nucleic acid, a nucleic acid analog, a filter, a matrix, a polymer, a charge switch material, a gel, a membrane, a fiber, a particle, a bead, an affinity resin, an ion exchange resin, a silica-based material, a magnetic material, or a combination thereof). In further embodiments, at least two of the plurality of second regions have different binding agents.

The invention also features a method of compartmentalizing a target fluid (e.g., any described herein) in a device, the method including: providing the device of the invention (e.g., any described herein), where the first region and the plurality of second regions are not in contact, introducing the target fluid to the first region, and moving the first layer or the second layer to form the plurality of combined regions, thereby separating the target fluid into compartments that are separated by an immiscible fluid and located in the plurality of combined regions.

In some embodiments, the method further includes introducing an immiscible fluid to at least one of the plurality of second regions. In some embodiments, at least one of the plurality of second regions includes a binding agent (e.g., any described herein), i.e., the second regions are capture regions. In further embodiments, a component of the target liquid binds to the binding agent.

In some embodiments, the method further includes performing a second relative movement of the first or second layers to connect the compartments with a plurality of fifth regions, to separate a reagent fluid in these fifth regions, and to mix the reagent fluid with the compartments.

In other embodiments, the method further includes performing a second relative movement of the first or second layers to connect the compartments with a plurality of sixth regions, to separate a reagent fluid in these regions, and to mix the reagent fluid with the compartments.

In any device or method described herein, a layer (e.g., the first layer, the second layer, or another layer) is planar or non-planar. In yet other embodiments, a layer (e.g., the first layer, the second layer, or a portion thereof) is differentially wetted.

In any device or method described herein, the device further includes a deformable layer (e.g., between the first layer and the second layer). In some embodiments, the device further includes a coating (e.g., on one or more of the first layer, the second layer, or the deformable layer, if present). In particular embodiments, the coating includes a fluoropolymer (e.g., any described herein).

In any device or method described herein, a layer (e.g., the first layer and/or the second layer) may translate longitudinally and/or rotate axially.

In any device or method described herein, the device may include more than two layers (e.g., three, four, five, six, seven, or more layers having one or more features, such as any described herein).

In any device or method described herein, the device further includes a lubricant (e.g., between the first layer and the second layer). Exemplary lubricants include a gas, a hydrocarbon, a fluorous substance, an ionic liquid, a non-Newtonian fluid, a lubricating powder or bead, or an immiscible fluid (e.g., as described herein).

In some embodiments, one or more of the regions includes a sample, a washing buffer, an elution buffer, a lysis agent, a reagent, a dye, a desiccant, a stabilizer, a protein, a nucleic acid, a filter, a membrane, or a marker (e.g., any described herein).

In any device or method described herein, the device may further include an injection port (e.g., for serial and/or sequential filling of the plurality of first chambers or at least one second chamber). In any device or method described herein, the device may further include one or more receiving chambers for controlling the volume of one or more fluids in the plurality of first regions and/or at least one second regions.

For any of the devices and methods described herein, the device is a microfluidic device. In some embodiments, the microfluidic device includes at least one feature that is 1,000 µm or less in at least one dimension. In other embodiments, the feature is at least one first region or at least one second region.

For any of the devices and methods described herein, sample analysis occurs with an electronic device (e.g., a cell phone, a smartphone, a mobile device, a mobile phone, a camera, a handheld camera, a video camera, an imaging device, or any detector, electronic device, or relay device described herein). In further embodiments, sample analysis includes relaying results from the sample analysis with the electronic device.

For any of the devices and methods described herein, sample storage, sample preparation, sample storage, sample treatment, sample volume quantification, and/or sample analysis occurs by use of an autonomous controller. In some embodiments, the controller includes a power element; a regulating element, which is optional and serves to maintains a relatively constant rate for the source of power; a timing element, which determines the rate of the relative movement of the device; a moving element, which promotes relative movement of the device; a transfer element, which transfers the force of the power source to the moving element and/or the timing element; and/or a switch, which is optional and serves to connect the power element either directly or indirectly to the moving element, where each of these elements can be interconnected either directly or indirectly (e.g., by a linkage, such as any described herein). Exemplary controllers are described herein.

Definitions

As used herein, "about" means +/−10% of the recited value.

By "above" is meant a relative position in which a first structure is in a higher position than a second structure. For instance, in a device including a first layer, a second layer above the first layer, and a third layer above the second layer, the term "above" provides the relative positional relationship of the first, second, and third layers and in no way signifies that the third layer must necessarily be the top or uppermost layer in the device. For instance, if the device is turned over, then the third layer would be the lowest layer in the device. Thus, it is understood that all relative positions described herein (e.g., above, beneath, between, etc.) are intended to encompass different orientations of the device in use, in operation, or during manufacture.

By "beneath" is meant a relative position in which a first structure is in a lower position than a second structure. For instance, in a device including a first layer, a second layer beneath the first layer, and a third layer beneath the second layer, the term "beneath" provides the relative positional relationship of the first, second, and third layers and in no way signifies that the first layer must necessarily be the top or uppermost layer in the device.

By "between" is meant a relative position in which an intermediate structure separates a first and a second structure. For instance, in a device including an intermediate layer disposed between a first and a second layer, the term "between" provides the relative positional relationship of the first, second, and intermediate layers and in no way signifies that the first layer must necessarily be the top or uppermost layer in the device.

By "chamber" is meant a volumetric portion of a layer capable of containing one or more substances, e.g., reagents, samples, immiscible fluids, and/or lubricants. Such chambers can have any useful structure, such as a well, a channel (e.g., a microchannel), a hole, a duct, a bridge, or a cavity having any useful cross-section or dimension(s).

By "to connect" is meant to allow for fluidic communication between two or more structures. Such fluidic communication can be between two or more similar structures (e.g., between two or more layers or between two or more chambers) or between two or more different structures (e.g., between one or more layers and one or more chambers).

By "fluidic communication" is meant the state of being able to pass a liquid or gas in a substantially unrestricted chamber. Fluidic communication can occur by any physical process, including diffusion across a membrane, active transport, or passive transport. Fluidic communication does not include limited diffusion of a substance (e.g., a reagent, sample, or fluid, as described herein) into the bulk material making up a layer.

By "immiscible fluid" is meant a first fluid (e.g., a gas or a liquid or a lubricant) that generally forms a different phase (e.g., forms an interface) over certain ranges of temperature, pressure, and composition as compared to a second fluid (i.e., target fluid). In some embodiments, the second fluid is an aqueous solution, a test sample, a sample for storage, preservation, processing, or analysis, and/or a reagent for storing, preserving, processing, or analyzing the sample; and the first fluid is a fluid that is immiscible with one or more of the second fluids at certain ranges of temperature, pressure, and composition useful for storing, preserving, processing, or analyzing the sample. An immiscible fluid includes those fluids having limited miscibility of the second fluid (e.g., a reagent, sample, or fluid, as described herein) over the certain ranges of temperature, pressure, composition, and other conditions when the device is in use. For instance, limited miscibility includes, e.g., limited dissolution of a first fluid is the second fluid, such as presence of from 1 ppb to 500 ppm (e.g., 1 ppb to 50 ppm) of the first fluid in the second fluid, as well as limited dissolution of a first fluid is the second fluid, such as presence of 1 ppb to 500 ppm (e.g., 1 ppb to 50 ppm) of the first fluid in the second fluid. A skilled artisan would understand methods of determining miscibility and the characteristics embodied in an immiscible fluid or in a combination of the immiscible fluid and the target fluid for storing, preserving, processing, or analyzing the sample.

By a "microfluidic" structure is meant a structure having at least one feature that is 1,000 µm or less in at least one dimension. Exemplary features include a layer (e.g., the thickness of a layer or the length, width, or height of a component embedded within a layer), a chamber (e.g., a well, a channel, a hole, a duct, a bridge, or a cavity), a membrane (e.g., the thickness of a membrane or the length, width, or height of a component (e.g., one or more pores or other physical structures) embedded within a membrane), or a capture region. In some embodiments, the structure includes more than one, two, three, four, five, six, seven, eight, nine, ten, twenty, or more features that are 1,000 µm or less in at least one dimension (e.g., height, width, depth, or thickness).

BRIEF DESCRIPTION OF THE DRAWINGS

FIGS. 12A-12B provide schemes having an area 1202 for compartmentalizing using an array of separated chambers, an area 1201 for compartmentalizing using an array 1220 of chambers 1221 connected by channels or necks, and an inlet 1203. Provided are a plan view (A) and a close-up view (B) of these areas. The device includes a top layer 1210 having an array 1220 of chambers connected by channels 1221, an array of separate chambers 1231, and another array of separated chambers 1241. The device also includes a bottom layer 1250 having an array 1260 of separated chambers 1261 (or receiving wells), an array of separate chambers 1271, and another array of separated chambers 1281.

DETAILED DESCRIPTION

Figure 1:
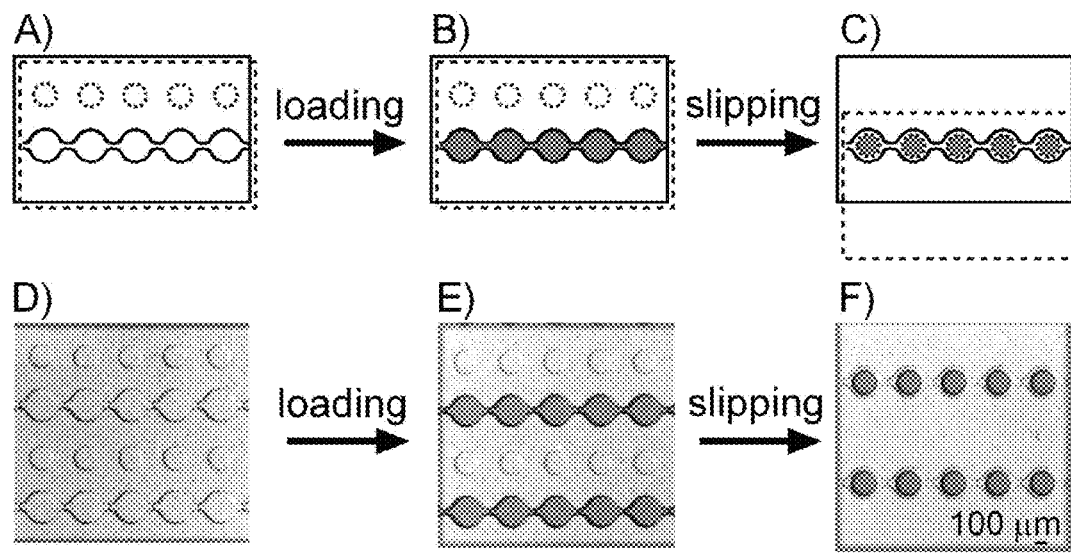
FIGS. 1A-1F provide schemes for surface tension driven compartmentalization on SlipChip. A: For the assembled SlipChip, the solid line is the top layer, and the dotted line is the bottom layer. Chambers on the top layer are connected by narrow channels. B: A solution can be introduced into the device through the connected chambers. C: The bottom layer can be slipped relative to the top layer to bring the chambers on the top layer in contact with receiving chambers (e.g., circular wells) on the bottom layer. The solution breaks up at the channel due to surface tension as the receiving chambers offer more space for a preferred shape of aqueous droplet. D-F: Bright field microphotographs are provided for a food dye experiment on SlipChip using the steps described in schemes A-C.

The invention provides devices and methods for compartmentalizing samples. In particular, such devices allow for multiple reactions to be performed while minimizing contamination. Described herein are structural features for such devices, as well as methods for their use in sample analysis.

The invention relates to use of surface energy to promote compartmentalization. Exemplary surface energy includes that of the target fluid, any interface described herein between two or more fluids or one or more fluids and a surface, such as liquid or solid surfaces. In general, surface energy [energy/area] can be determined by the Young's equation, as well as variations thereof, and/or by accounting for Gibbs free energy. Further, surface energy, including surface tension [force/length], can be determined between particular interfaces formed by and between different phases, including one or more of the following: a target fluid (e.g., a sample, a reagent, or combinations thereof), an immiscible fluid (e.g., a lubricant), and a surface of a device (e.g., any region described herein, such as a chamber, a channel, a surface, or a portion thereof, including characteristics such as geometry, dimension, texture, and/or surface characteristics). Exemplary interfaces include a target fluid/immiscible fluid interface, a target fluid/device interface, an immiscible fluid/device interface, and a target fluid/immiscible fluid/device interface. Accordingly, surface energy can be determined between any useful interface or fluid, as well as controlled by designing the extent of interaction at and between these interfaces.

In particular, the invention encompasses a device having two or more layers having features that can be connected by relative movement (e.g., as described herein). For instance, slipping or relative movement results in a change of surface energy (e.g., of the target fluid and/or the immiscible fluid), such that it is favorable for the target fluid to be compartmentalized. In some embodiments, the surface energy of the target fluid before slipping is less than the surface energy of the target fluid after slipping, such that it is favorable for the target fluid to be compartmentalized. In further embodiments, the surface energy of the target fluid in the first region of the first layer is less than the surface energy of the target fluid in the combined region formed by the first region and a second region in the second layer. For instance, different portions of the device can be designed to have different surface energies to promote compartmentalization after slipping.

In some non-limiting embodiments, the devices include a first region, as described herein, that facilitates surface tension driven compartmentalization of samples in a device. In some embodiments, a substance having surface energy A is contained in a first region. Upon relative movement of a layer of a device, a substance is exposed to a plurality of second regions and contained in a combined first region and second region, where the substance in this combined region has surface energy B. This change in surface energy (from surface energy A to surface energy B) can result in the substance preferentially forming compartments (e.g., droplets). In other embodiments, upon relative movement of a layer of a device, a substance contained in a first region (e.g., having volume $V_1$) is exposed to a plurality of second regions (e.g., having volume $V_2$). This increase in volume (from volume $V_1$ to volume $V_1+V_2$) can result in the substance preferentially forming compartments or droplets. In particular embodiments, the first region includes at least two first chambers connected by a first channel, where the geometry of the first channel and first chambers can promote break-up at distinct locations, such that uniform compartments can be formed. Other embodiments of controlling surface energy (e.g., by using surface chemistry rather than surface geometry) are described herein. Such compartments of a substance can be surrounded by any useful immiscible fluid, such as air, a lubricant, or any other fluid described herein.

Additional, non-limiting benefits of the device of the invention include less stringent requirements for aligning the layers in a device, ease of fabrication, and/or reduced cross-contamination. The devices and methods of the invention can be useful for any analysis (e.g., digital nucleic acid amplification, single molecule analysis, multiplex reaction, etc.).

Surface Energy

The invention relates to use of surface energy to control compartmentalization of a target fluid. Surface energy can be controlled by controlling the dimension, geometry, or texture of one or more regions and/or by controlling the surface characteristics (e.g., hydrophobicity, lipophobicity, fluorophilicity, and/or hydrophilicity). These different parameters can be used separately or together to create compartments by minimizing the surface energy of the system.

Surface energy can be determined or measured by any useful method. Exemplary methods includes use of the Young's equation, Gibb's free energy determinations, Wulff construction, as well as measurements of a contact angle (e.g., using a goniometer), surface tension (e.g., using the bubble pressure, capillary rise, drop volume, Du Noüy ring, Du Noüy-Padday, levitated drop, pendant drop, sessile drop, spinning drop, stalagmometric, or Wilhelmy plate methods).

Devices

The devices of the invention include structural features, such as a layer and/or a chamber (e.g., a well, a channel, a hole, a bridge, or a cavity, or any described herein). The chamber can be completed or partially enclosed (e.g., such as in an enclosed channel) or be open (e.g., such as in a well). The various structures described herein can have any useful dimension, cross-section, planarity, or surface characteristic. Any of the devices described herein can be used individually or in combination with the devices or with one or more features of the devices described in, e.g., U.S. Pub. Nos. 2006-0003439; 2007-0172954; 2010-0078077; 2010-0233026; 2011-0112503; 2011-0142734; 2011-0165037; 2011-0176966; 2011-0177586; and 2012-0329171; U.S. Pat. Nos. 7,129,091; 7,655,470; 7,901,939; 8,304,193; 8,273,573; and 8,329,407; U.S. patent application Ser. No. 13/648,922, filed Oct. 10, 2012, Ser. No. 13/868,009, filed Apr. 22, 2013, and Ser. No. 13/868,028, filed Apr. 22, 2013; Int. Pub. Nos. WO 2004/038363; WO 2009/149257; WO 2008/079274; and WO 2006/101851; and U.S. Provisional Pat. Appl. Nos. 60/379,927; 60/394,544; 60/585,801; 60/623,261; 60/763,574; 60/875,856; 60/881,012; 60/899,449; 60/930,316; 60/936,606; 60/962,426; 61/130,930; and 61/335,570. Further, any of these devices can be used in any method described herein, as well as those methods described in the above-mentioned U.S. Pat. Nos., U.S. Pub. Nos., U.S. Pat. Appl. No., Int. Pub. Nos., and U.S. Provisional Pat. Appl. Nos., which are incorporated herein by reference.

Dimensions, Cross-Sections, Texture, and Geometry

The layer, chamber, or other structure can have any useful dimension. Useful dimensions include any length, width, or depth that can be uniform or varied along any useful axis. Exemplary dimensions in any useful axis (e.g., perpendicular to the axis of fluid flow) include less than about 50 mm (e.g., less than about 40 mm, 20 mm, 15 mm, 10 mm, 5 mm, 2 mm, 1 mm, 500 µm, 200 µm, 60 µm, 50 µm, 40 µm, 30 µm, 15 µm, 10 µm, 3 µm, 1 µm, 300 nm, 100 nm, 50 nm, 30 nm, or 10 nm) or from about 10 nm to about 50 mm (e.g., 10 nm to 40 mm, 10 nm to 20 mm, 10 nm to 15 mm, 10 nm to 10 mm, 10 nm to 5 mm, 10 nm to 2 mm, 10 nm to 1 mm, 10 nm to 500 µm, 10 nm to 200 µm, 10 nm to 60 µm, 10 nm to 50 µm, 10 nm to 40 µm, 10 nm to 30 µm, 10 nm to 15 µm, 10 nm to 10 µm, 10 nm to 3 µm, 10 nm to 1 µm, 100 nm to 50 mm, 100 nm to 40 mm, 100 nm to 20 mm, 100 nm to 15 mm, 100 nm to 10 mm, 100 nm to 5 mm, 100 nm to 2 mm, 100 nm to 1 mm, 100 nm to 500 µm, 100 nm to 200 µm, 100 nm to 60 µm, 100 nm to 50 µm, 100 nm to 40 µm, 100 nm to 30 µm, 100 nm to 15 µm, 100 nm to 10 µm, 100 nm to 3 µm, 100 nm to 1 µm, 1 µm to 50 mm, 1 µm to 40 mm, 1 µm to 20 mm, 1 µm to 15 mm, 1 µm to 10 mm, 1 mm to 5 mm, 1 µm to 2 mm, 1 µm to 1 mm, 1 µm to 500 µm, 1 µm to 200 mm, 1 µm to 60 µm, 1 mm to 50 µm, 1 µm to 40 µm, 1 µm to 30 µm, 1 mm to 15 µm, 1 µm to 10 µm, 1 µm to 3 µm, 10 µm to 50 mm, 10 µm to 40 mm, 10 µm to 20 mm, 10 µm to 15 mm, 10 µm to 10 mm, 10 µm to 5 mm, 10 µm to 2 mm, 10 µm to 1 mm, 10 µm to 500 µm, 10 µm to 200 µm, 10 µm to 60 µm, 10 µm to 50 µm, 10 µm to 40 µm, 10 µm to 30 µm, 10 µm to 15 µm, 50 µm to 50 mm, 50 µm to 40 mm, 50 µm to 20 mm, 50 µm to 15 mm, 50 µm to 10 mm, 50 µm to 5 mm, 50 µm to 2 mm, 50 µm to 1 mm, 50 µm to 500 µm, 50 µm to 200 µm, 50 µm to 60 µm, 100 µm to 50 mm, 100 µm to 40 mm, 100 µm to 20 mm, 100 µm to 15 mm, 100 µm to 10 mm, 100 µm to 5 mm, 100 µm to 2 mm, 100 µm to 1 mm, 100 µm to 500 µm, or 100 µm to 200 µm).

The dimensions of any structure (e.g., one or more chambers) may be chosen to maintain a particular volumetric or linear flow rate of a fluid in the device and/or to control the size of the compartments. For example, such dimensions may be useful to control the filling of the device with particular fluids or the flow rate of such fluids through the areas. In another example, the dimension of the chamber or the chamber connecting the at least two chambers can be used to control the size of the compartment.

The layer, chamber, or other structure can include any useful texture. For instance, the texture of the structure can be modified to obtain particular surface energy characteristics. Exemplary textures include pores, nanostructures, microstructures, and superhydrophobic surfaces (e.g., honeycomblike hydrophobized polyelectrolyte multilayer surface coated with silica nanoparticles, micropost arrays, micropillars, micro-hoodoo structures, nanonails, fractals, electrospun fibers, or wire gratings, including those described in Tuteja et al., MRS Bulletin 33:752-758 (2008), which is incorporated herein by reference).

The layer, chamber, or other structure can include any useful cross-section or geometry. Cross-sections can be of any useful shape (e.g., rectangular, square, circular, oval, irregular, or triangular cross-sections) that can optionally vary along the axis of any structure. For instance, when the structure is a channel, the cross-section of the channel along the axis of fluid flow can change from one cross-sectional shape to another, such as from a circular to a rectangular cross-section. In another instance, the dimensions of the cross-section can be uniform or can vary along any axis, such as a channel that tapers or expands along the axis of fluid flow.

Figure 4:
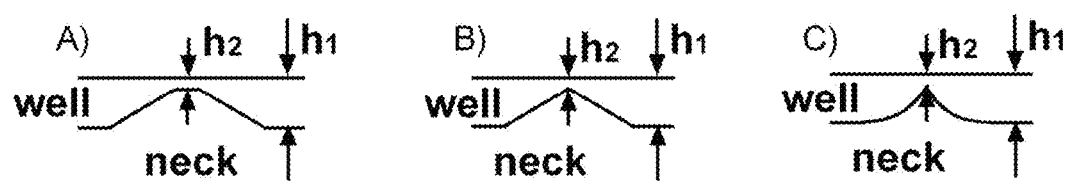
FIGS. 4A-4C provide cross-sectional views of different geometries of chambers (e.g., wells) and channels (e.g., necks) with different cross-sectional heights ($h_1$ versus $h_2$).

In particular, the cross-section can be optimized to promote break-up at interfaces between a chamber and a channel, where two or more chambers are connected by a channel that has a narrower cross-sectional dimension than a cross-sectional dimension of the chambers. For example, as shown in FIG. 4, the chamber or well has a cross-sectional dimension of $h_1$, and the channel or neck has a cross-sectional dimension of $h_2$, where $h_1 > h_2$. The area having $h_2$ provides a region that promotes an increased curvature of a substance (e.g., with air or any other fluid, such as a lubricant), as compared to the area having $h_1$. Based on this increased curvature, surface tension may promote break-up of the substance into compartments or droplets.

Planarity

The layer, chamber, or other structure can include any useful planarity. In some instances, the surfaces of the first and second layers are substantially planar to facilitate movement of these layers. Such layers can further be uniform or non-uniform in other characteristics, such as height, width, and/or depth.

Alternatively, the surfaces of the structures can be non-planar and substantially complementary to allow for movement. For instance, one or more layers can include a curvilinear surface, such as the surface of a cylinder, a concave surface, or a convex surface. In one example, the first layer includes a first cylindrical surface, and the second layer includes an annular cylinder having an opening, an inner cylindrical surface, and an outer cylindrical surface. When the first layer is inserted into the opening of second layer, the first cylindrical surface and the inner cylindrical surface of the second layer are complementary, thereby allowing the first layer to move within the second layer.

Accordingly, the layers can include any useful complementary surfaces, such as concentric spheres, cones, cylinders, etc.

Further, the device can include additional layers having any useful planarity, and each layer can have similar, different, or complementary structure characteristics (e.g., planarity). Moreover, to ensure that uniform pressure is applied over the first and second areas or layers, the surface may vary to ensure when pressure is applied in discrete locations along the device, a uniform pressure can be applied. For example, when the two surfaces are conical, pressure may be applied to bring two surfaces into close contact. Exemplary devices and their characteristics are described in U.S. Pub. No. 2012-0028342, U.S. Pub. No. 2012-0264132, Int. Pub. No. WO 2010/111265, U.S. patent application Ser. No. 13/868,009, filed Apr. 22, 2013, U.S. patent application Ser. No. 13/868,028, filed Apr. 22, 2013, as well as U.S. Provisional Pat. Appl. Nos. 61/162,922, filed Mar. 24, 2009; 61/262,375, filed Nov. 18, 2009; 61/340,872, filed Mar. 22, 2010; 61/516,628, filed Apr. 5, 2011; and 61/518,601, filed May 9, 2011, each of which is incorporated herein by reference in its entirety.

Surface Characteristics

The layer, chamber, or other structure can include any useful surface characteristics. Exemplary surface characteristics include differentially wetting (e.g., hydrophobic, lipophobic, fluorophilic, or hydrophilic), smoothness, or porosity. Each layer can have substantially the same or different surface characteristics. For instance, both the first and second layers can be substantially hydrophobic, or the first layer can be substantially hydrophobic, and the second layer can be substantially hydrophilic. Similarly, each of the first chambers of the first layer can have substantially the same or different surface characteristics. In one example, all of the first chambers are substantially hydrophilic, and the remaining portions of the first layer are hydrophobic, thereby allowing for preferentially wetting of aqueous reagents within the first chambers as compared to other portions of the first layer. By controlling the surface characteristics, fluid flow and/or compartmentalization can be controlled. For example, where an open chamber (e.g., an open well) is used, a fluid may be held within an open chamber using surface tension (i.e., a concave or convex meniscus), particularly if the open chamber has a surface characteristic allowing for preferentially wetting of the fluid.

Chambers in different layers can have substantially the same or different surface characteristics. For instance, first chambers in a first layer can have the same surface characteristics as second chambers in a second layer. Upon connecting the first and second chambers by relative movement, a substance will be compartmentalized within the volume formed by the combination of the first and second chambers. In another instance, the first chambers have different surface characteristics as the second chamber, where the first chambers are substantially hydrophobic, and the second chambers are substantially hydrophilic. If the substance to be compartmentalized is an aqueous solution, then the substance will preferentially wet the second chambers and the compartmentalized substance will more preferentially adhere within the second chambers. In a similar manner, the surface characteristics (e.g., hydrophobicity, lipophobicity, fluorophilicity, or hydrophilicity) of the chambers in one or more layers can be modified to obtain the desired compartments for a particular sample.

Furthermore, chambers and channels (e.g., channels connecting two chambers) in the same or different layer can have substantially the same or different surface characteristics. For instance, chambers and the channels connecting the chambers can have the same surface characteristics. In some embodiments, the chambers and channels are substantially hydrophobic. If the substance to be compartmentalized is an aqueous solution, then the substance will reside in the portion of the chamber or channel that will minimize surface tension. When the channel has a smaller cross-sectional dimension than the chamber, then the substance will preferentially remain in the chamber. In another instance, chambers and the channels connecting the chambers can have the difference surface characteristics. In some embodiments, the chambers are substantially hydrophilic, and the channels are substantially hydrophobic. If the substance to be compartmentalized is an aqueous solution, then the substance will reside preferentially in the chamber. In other embodiments, the chambers are substantially hydrophobic, and the channels are substantially hydrophilic. In a similar manner, the surface characteristics (e.g., hydrophobicity, lipophobicity, fluorophilicity, or hydrophilicity) of the chamber and channels can be modified to obtain the desired compartments for a particular sample.

Surface characteristics can be obtained by using any useful material or surface modification process. For instance, one or more chambers can include porous materials, e.g., porous glass, aluminum oxide, or a cellulose matrix. Such chambers may be made by depositing a matrix into the area, by patterning a porous layer, and/or by filling or coating a porous layer around areas. Exemplary cellulose patterning processes are described in Martinez et al., Anal. Chem. 80:3699-3707 (2008), Martinez et al., Angew. Chemie Int. Ed. 46:1318-1320 (2007), Martinez et al., Lab Chip 8:2146-2150 (2008), and Macek et al., Chromatographic Rev. 15:1-28 (1971); and other materials may be patterned by methods described in Vozzi et al., Biomaterials 24:2533-2540 (2003) for PLGA scaffolds; Desai et al., Biosens. Bioelectron. 15: 453-462 (2000), Pichonat et al., J. Micromech. Microeng. 15:S179-S184 (2005), Cohen et al., Biomed. Microdevices 5:253-259 (2003), Ohji et al., Proc. SPIE Int'l Soc. Optical Eng. 3223:189-197 (1997), and Chu et al., J. Microelectromech. Sys. 15: 671-677 (2006) for porous silicon membranes; De Jong et al., Lab Chip 5: 1240-1247 (2005) for thin devices; Petronis et al., J. Biomed. Mater. Res. 66:707-721 (2003) for silicon substrates; and Wang et al., Sens. Actuat. B 123:101-106 (2007) for palladium-silver thin film for hydrogen sensing, each of which is incorporated herein by reference in its entirety.

The layer, chamber, or other structure can be formed from any useful material. The materials used to form the devices of the invention are selected with regard to physical and chemical characteristics that are desirable for proper functioning of the device. Suitable, non-limiting materials include polymeric materials, such as silicone polymers (e.g., polydimethylsiloxane and epoxy polymers), polyimides (e.g., commercially available Kapton® (poly(4,4'-oxydiphenylene-pyromellitimide, from DuPont, Wilmington, Del.) and Upilex™ (poly(biphenyl tetracarboxylic dianhydride), from Ube Industries, Ltd., Japan)), polycarbonates, polyesters, polyamides, polyethers, polyurethanes, polyfluorocarbons, fluorinated polymers (e.g., polyvinylfluoride, polyvinylidene fluoride, polytetrafluoroethylene, polychlorotrifluoroethylene, perfluoroalkoxy polymer, fluorinated ethylene-propylene, polyethylenetetrafluoroethylene, polyethylenechlorotrifluoroethylene, perfluoropolyether, perfluorosulfonic acid, perfluoropolyoxetane, FFPM/FFKM (perfluorinated elastomer [perfluoroelastomer]), FPM/FKM (fluorocarbon [chlorotrifluoroethylenevinylidene fluoride]), as well as copolymers thereof), polyetheretherketones (PEEK), polystyrenes, poly(acrylonitrile-butadiene-styrene)(ABS), acrylate and acrylic acid polymers such as polymethyl methacrylate, and other substituted and unsubstituted polyolefins (e.g, cycloolefin polymer, polypropylene, polybutylene, polyethylene (PE, e.g., cross-linked PE, high-density PE, medium-density PE, linear low-density PE, low-density PE, or ultra-high-molecular-weight PE), polymethylpentene, polybutene-1, polyisobutylene, ethylene propylene rubber, ethylene propylene diene monomer (M-class) rubber), and copolymers thereof (e.g., cycloolefin copolymer); ceramics, such as aluminum oxide, silicon oxide, zirconium oxide, and the like); semiconductors, such as silicon, gallium arsenide, and the like; glass; metals; as well as coated combinations, composites (e.g., a block composite, e.g., an A-B-A block composite, an A-B-C block composite, or the like, of any materials described herein), and laminates (e.g., a composite material formed from several different bonded layers of identical or different materials, such as polymer laminate or polymer-metal laminates, e.g., polymer coated with copper, a ceramic-in-metal or a polymer-in-metal composite) thereof.

The device can be formed by any useful process, including but not limited to molding (e.g., injection molding, vacuum molding, or overmolding), machining (e.g., drilling, milling, or sanding), and etching (e.g., deep reactive ion etching, KOH etching, or HF etching). In microfluidic applications, the layers can be fabricated from a material that enables formation of high resolution features (e.g., microchannels, chambers, mixing features, and the like, that are of millimeter, micron, or submicron dimensions), such as by using microfabrication techniques (e.g., dry etching, wet etching, laser etching, laser ablation, molding, embossing, or the like, to have desired miniaturized surface features). Further, the material can be optionally treated to provide a chemically inert surface (e.g., by silanization with tridecafluoro-1,1,2,2-tetrahydrooctyl-1-trichlorosilane), a biocompatible surface (e.g., by treatment with bovine serum albumin), and/or a physically stable material (e.g., by extensive cross-linking).

The layers can include any useful material. For instance, a portion of a layer can include a membrane, or the entire layer can include a continuous membrane or a patterned membrane. Furthermore, such membranes can be integrated with one or more layers (e.g., by overmolding or lamination) having one or more chambers and/or inlets. Alternatively, such membranes can be present in a separate layer. Exemplary membranes include a PTFE (e.g., Teflon®) membrane, a polycarbonate membrane, a cellulose membrane, or other membranes that are known in the art.

The device can also include one or more deformable layers. Such deformable layers can be designed to deform as pressure is applied, such as to redistribute local pressure into uniform pressure over a surface of the device and/or to control connection or disconnection between layers or chambers.

Furthermore, one or more layers and/or chambers can be optionally coated. In particular embodiments, a coating is used to minimize cross-contamination between layers, where relative movement between layers can result in thin films of reagents forming between layers. The coating can be used to control surface chemistry (e.g., by increasing the contact angle to about 154° with water). In particular embodiments, one or more layers and/or chambers are coated with a fluoropolymer. Exemplary fluoropolymers include fluorinated ethylene propylene resin (e.g., Teflon® FEP TE-9568, a dispersion composed of approximately 54% (by total weight) of a negatively charged, hydrophobic colloidal fluoropolymer resin (0.1 to 0.30 µm FEP particles suspended in water) and approximately 6% (by weight of FEP resin) of a nonionic wetting agent and stabilizer based on the weight of the FEP solids), perfluoroalkoxy copolymer resin (e.g., Teflon® PFA TE-7224, a dispersion composed of approximately 60% (by total weight) of PFA resin (0.05 to 0.5 µm particles) dispersed in water and approximately 5% by weight of a nonionic wetting agent and stabilizer based on the weight of the PFA solids; or Teflon® PFAD 335D, a dispersion composed of approximately 60% (by total weight) of PFA resin (0.20 µm average diameter particles) dispersed in water and approximately 6% by weight of a nonionic surfactant based on the weight of the PFA solids), polytetrafluoroethylene (e.g., Teflon® PTFE DISP 30, a dispersion composed of approximately 60% (by total weight) of PTFE resin (0.220 µm average diameter particles) dispersed in water and approximately 6% by weight of a nonionic surfactant based on the weight of the PTFE solids), or a copolymer of tetrafluoroethylene and ethylene (e.g., Tefzel® Type LZ, CLZ, or CLZ-20, available in nominal gauges of 50, 100, 200, 500, 750, 1000, or 2000, having a thickness of 0.0005, 0.0010, 0.0020, 0.0050, 0.0075, 0.0100, or 0.0200 inches).

The device can include multiple layers to accommodate multiplexed sample processing, preparation, and/or analysis. In particular embodiments, the layers are provided in a stacked configuration having a top layer, a bottom layer, and a plurality of intermediate layers. The intermediate layers can have one or more chambers or arrays of chambers able to be connected by relative movement. Each of the layers can be connected and disconnected separately from the other layers within the stack. In this manner, connections and disconnections between layers can be controlled to perform the desired reactions or multiplexed analysis.

The layers can include a plurality of chambers, where each chamber may be the same or different. Furthermore, a plurality of arrays of such chambers can be present in one or more layers (e.g., see arrays in FIGS. 10A-10E, which can be connected sequentially or serially). Such chambers can include any volumetric structure. Each chamber in a layer or an array may have the same surface dimension, cross-section, planarity, or surface characteristic. Alternatively, each chamber in a layer or an array may have different surface dimensions, cross-sections, planarity, or surface characteristics. Exemplary chambers include an open groove or trench, a closed channel, an open or closed well, etc. Such chambers are useful for holding or transporting one or more reagents, samples, or fluids (e.g., a lubricant).

The device can be designed to include a plurality of chambers. As shown in FIGS. 10A-10E, the device can include two layers having 100 chambers in the top layer 1010. The top layer 1010 can include an array 1050 of first chambers 1060 connected by a first channel 1065 including an outlet 1066. The device can include multiple arrays 1050-1053 and/or registration marks 1081-1084 (e.g., to facilitate fabrication or alignment of layers). The arrays can include chambers and channels of different or the same geometry. For instance, in one of the arrays 1052, the chamber 1070 has a different geometry than the chamber 1060 in array 1050. In another example, the channel 1075 connecting the chambers has a different geometry than the channel 1065 in array 1050.

The arrays 1050-1053 can be connected by multiple channels 1025 and 1030, which in turn connect to an inlet 1020 to facilitate introducing of a substance (e.g., a reagent, solution, sample, or any described herein).

Figure 10A:
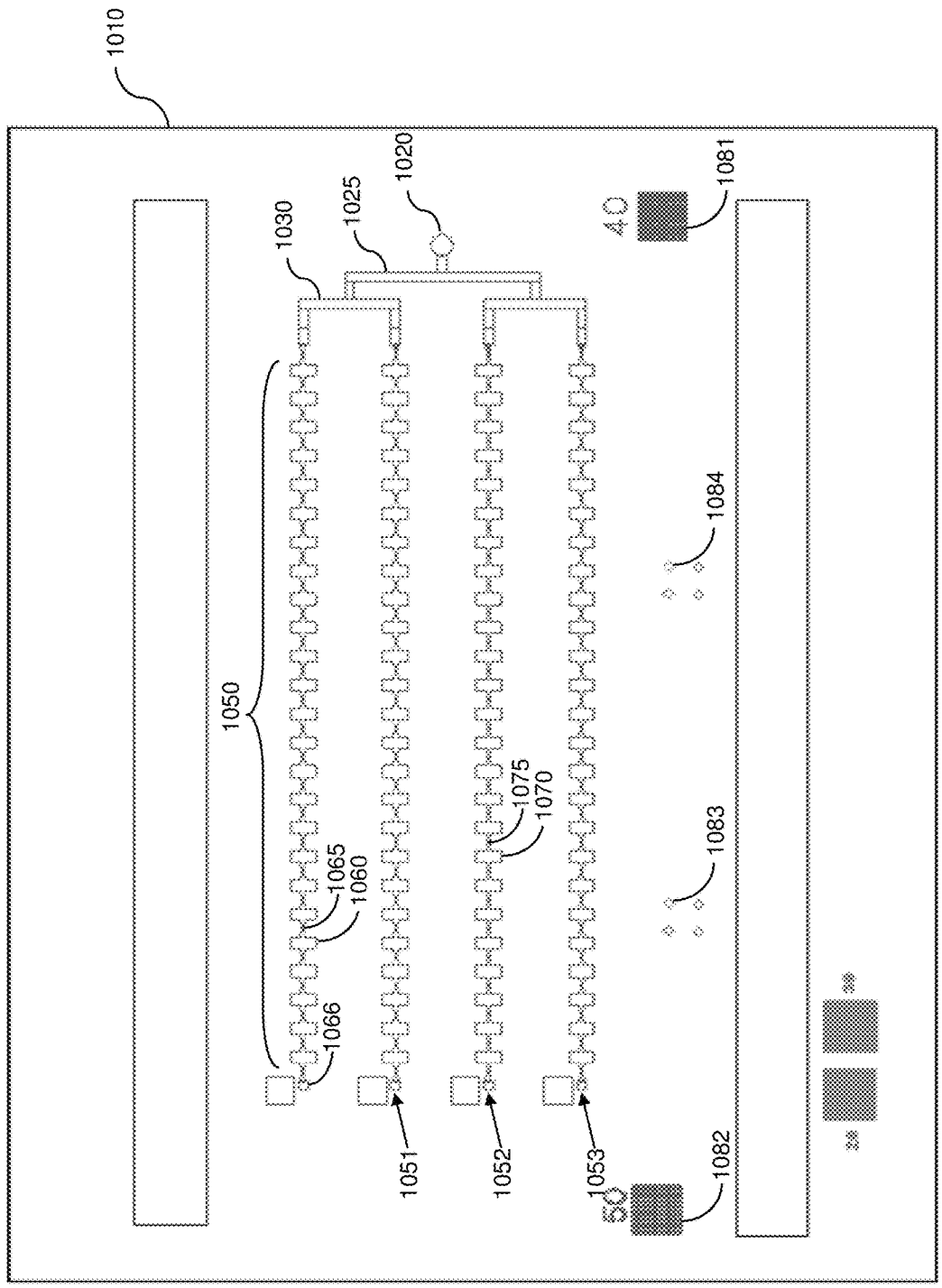
FIGS. 10A-10E provide schemes of an exemplary device having 100 chambers in the top layer. Provided are the top layer 1010 (A), bottom layer 2010 (B), and assembled top and bottom layers (C). Also provided is the device after the bottom layer is slipped up to a first position (D) and after the bottom layer is slipped up to a final position (E).
Figure 10B:
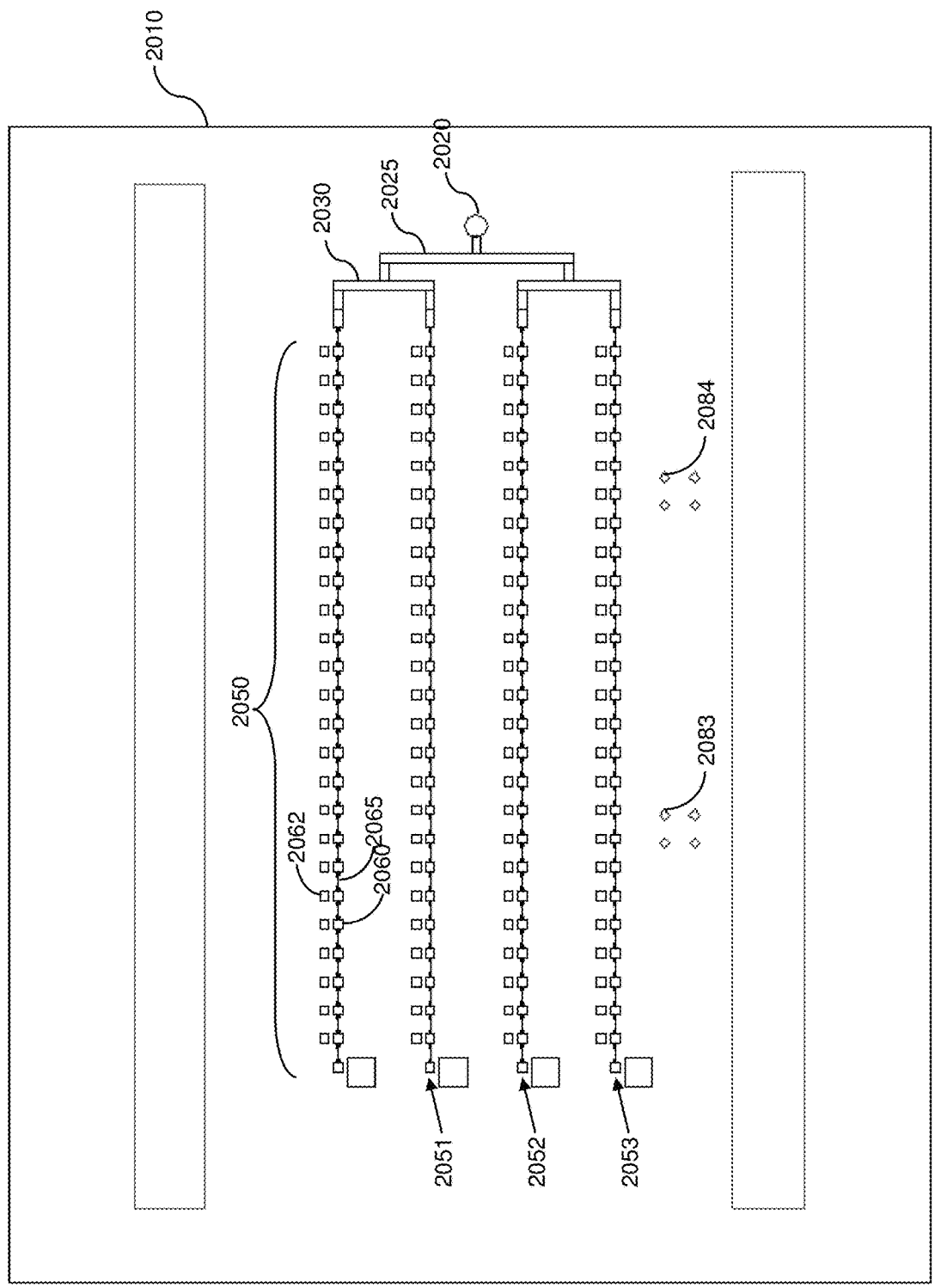
Figure 10C:
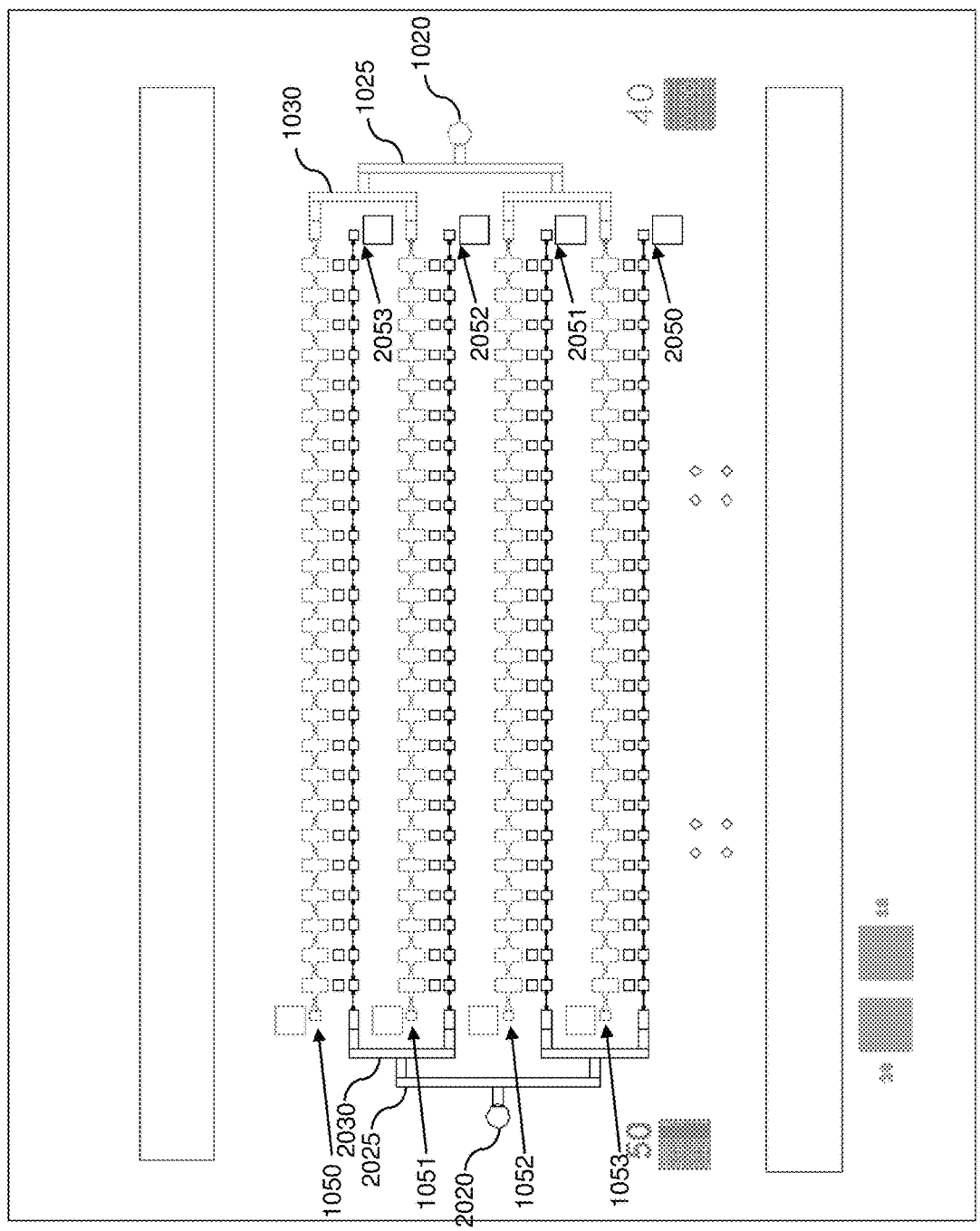
Figure 10D:
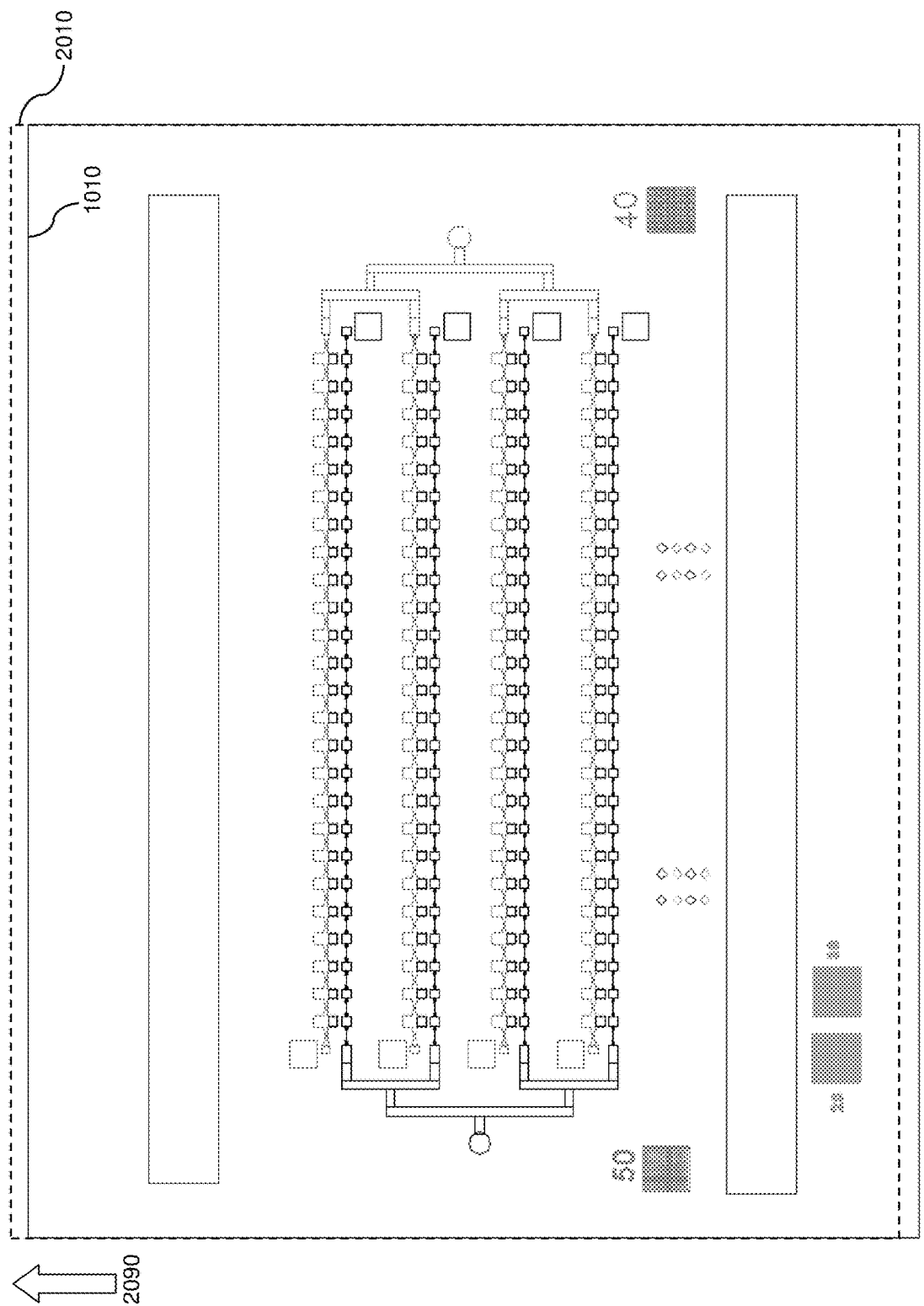
Figure 10E:
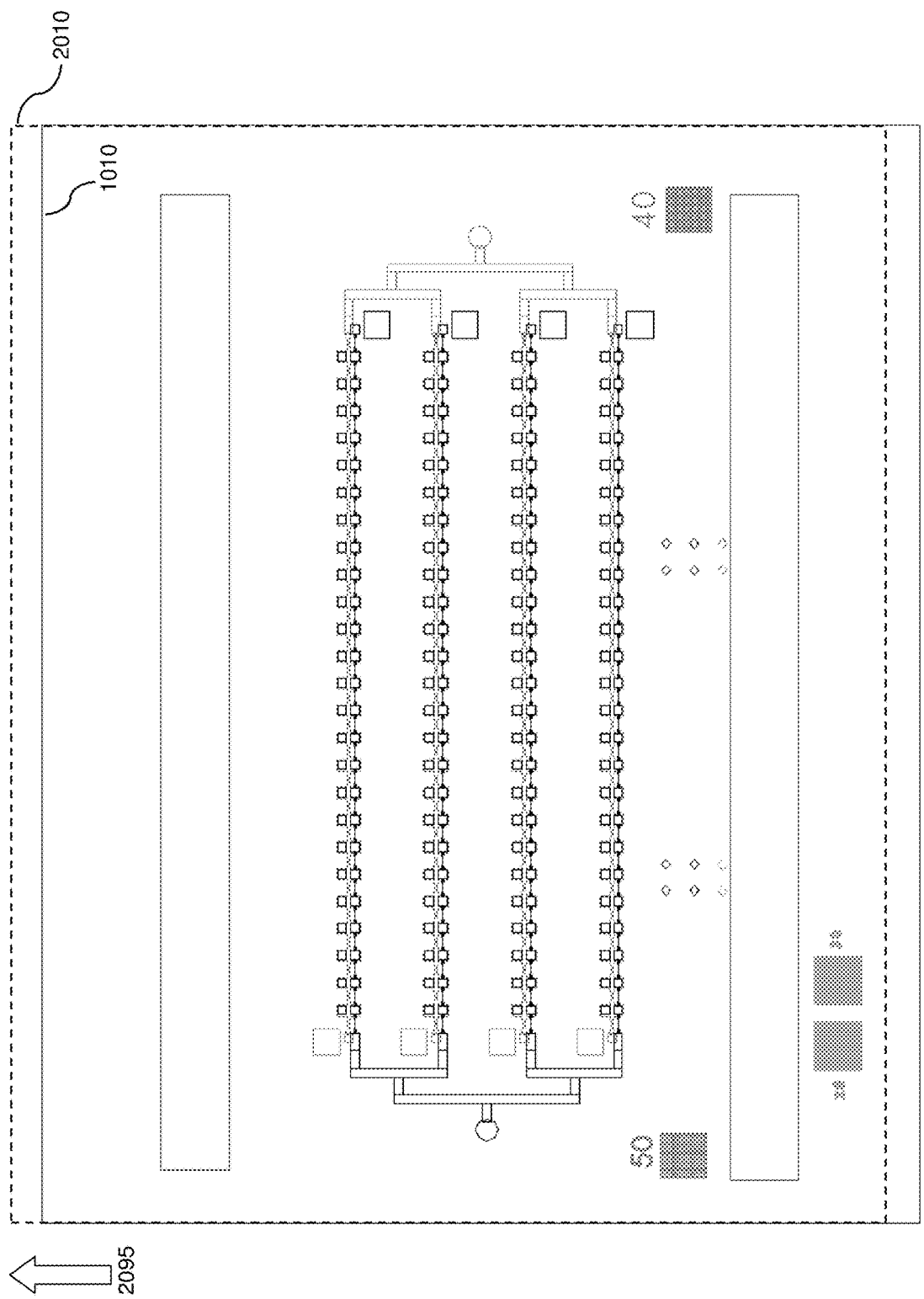
Figure 11A:
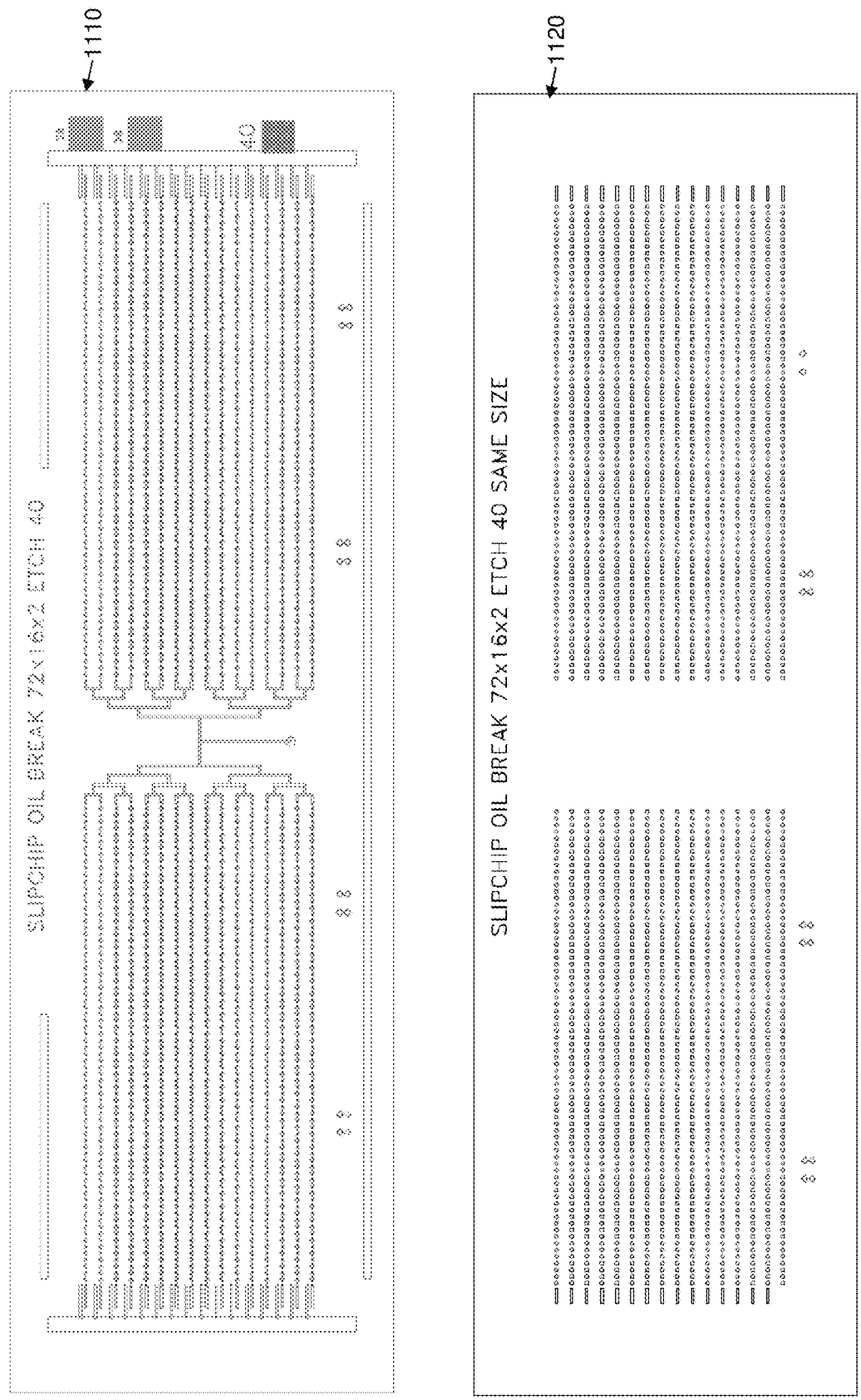
FIGS. 11A-11C provide schemes of an exemplary Digital PCR Chip (2304 chambers, 1×3 inch). Provided are the top layer 1110 and bottom layer 1120 (A), the assembled top and bottom layers (B), and the device after a first slip (C, indicated by arrow 1190).
Figure 11B:
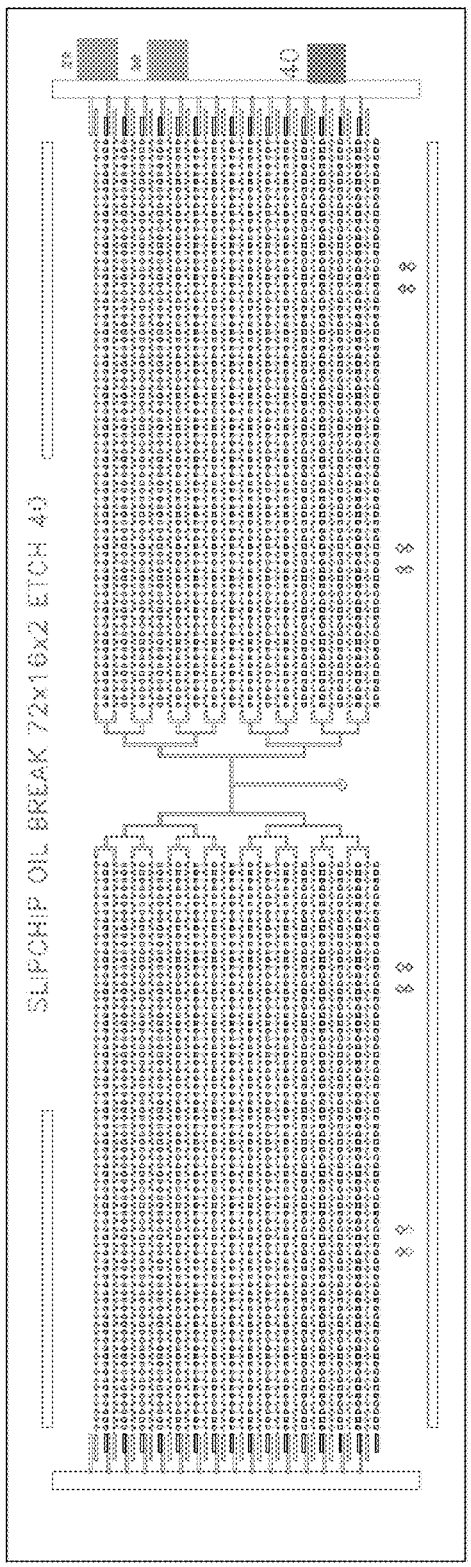
Figure 11C:
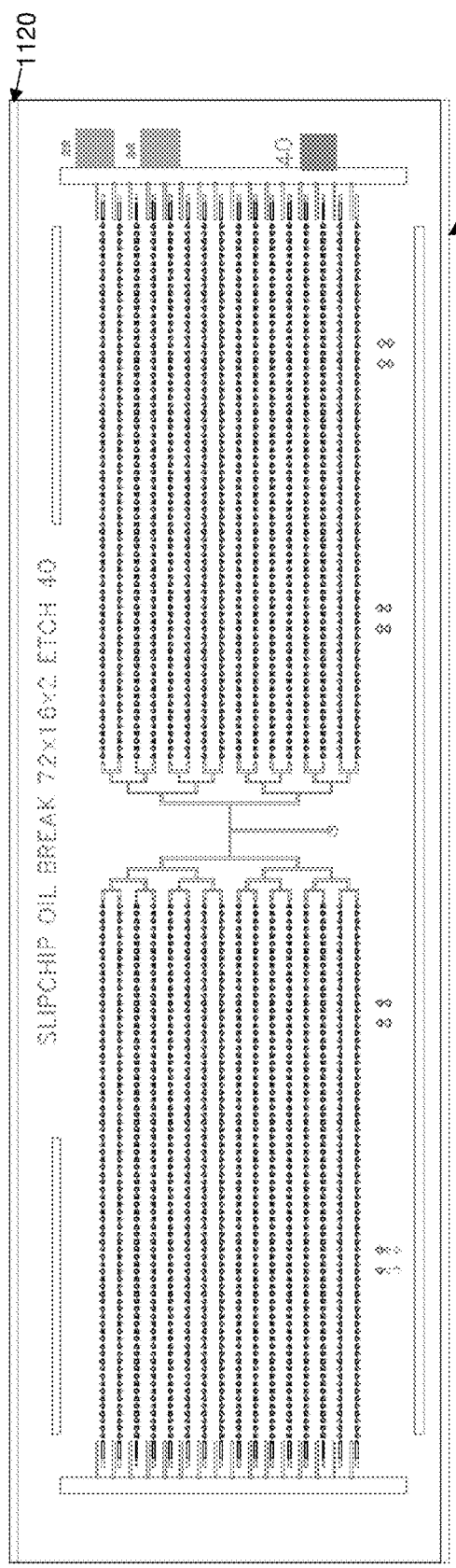

The bottom layer 2010 can include an array 2050 of second chambers 2062 and of third chambers 2060 connected by a second channel 2065. The device can include multiple arrays 2050-2053 and/or registration marks 2083-2084 (e.g., to facilitate fabrication or alignment of layers). The arrays 2050-2053 can be connected by multiple channels 2025 and 2030, which in turn connect to an inlet 2020 to facilitate introducing of a substance (e.g., a reagent, solution, sample, or any described herein). Assembly of the top and bottom layers (e.g., as shown in FIG. 10C) and movement of these layers (e.g., as indicated by arrows 2090 and 2095 in FIGS. 10D-10E) provides connections between the various chambers and channels. As shown in FIGS. 11A-11C, the device can include two layers having 2304 chambers in the top layer 1110. As shown in FIGS. 12A-12B, the device an include two layers with different areas allowing for different modes of compartmentalizing a substance.

In some embodiments, the first region (e.g., a first channel) is not preferentially wetted by an aqueous target fluid under the conditions of device use (e.g., the surface of the first channel is substantially hydrophobic and/or the channel is filled with a gas or a hydrophobic liquid, such as described herein).

A channel can be used to connect two chambers in the same layer. The surface dimensions, cross-sections, planarity, or surface characteristics of the channel can be optimized to break-up of a substance into compartments or droplets (e.g., microdroplets). In some embodiments, the channel is not preferentially wetted by liquid water under the conditions of device use (e.g., the surface of the channel is substantially hydrophobic and/or the channel is filled with a gas or a hydrophobic liquid, such as any fluid described herein). In some embodiments, the channel and the distance between two chambers is less than about 500 μm (e.g., less than about 300 μm, 100 μm, 50 μm, or 20 μm).

Capture Regions

The devices of the invention can include one or more capture regions (e.g., within any structure described herein, such as a region, including a chamber, a channel, or a well). The capture region can include any useful material to capture one or more targets or analytes (e.g., a nucleic acid or any described herein). Capture regions, such as those for use in combination with the devices herein, include those described in U.S. patent application Ser. No. 13/868,009, filed Apr. 22, 2013, and Ser. No. 13/868,028, filed Apr. 22, 2013, each of which is incorporated herein in its entirety.

A capture region includes a material or binding agent to which a component (e.g., analyte, nucleic acid, protein, carbohydrate, lipid, cell, cellular organelle, metabolite, drug, or toxin) in a sample binds.

Exemplary binding agents include antibodies, antibody fragments (e.g., Fc fragments), other oligo- or polypeptides, nucleic acids, cellular receptors, ligands, aptamers, MHC-peptide monomers or oligomers, biotin, avidin, oligonucleotides, coordination complexes, synthetic polymers (e.g., hydrophilic, hydrophobic, or charged), carbohydrates, charged surfaces, and combinations thereof. Modified nucleic acids (or oligo- or poly-nucleotides), protein, or analogs thereof may also be employed. Such modified nucleic acids and analogs include Locked Nucleic Acids, peptide nucleic acids, glycerol nucleic acids, morpholino nucleic acids, or threose nucleic acids connected, e.g., via the 5', 3' or 2' carbon of the radical, to a phosphate group and a base. Nucleic acids, modified nucleic acids, and nucleic acid analogs may include a purine or pyrimidine base, e.g., cytosine, guanine, adenine, thymine, uracil, xanthine, hypoxanthine, inosine, orotate, thioinosine, thiouracil, pseudouracil, 5,6-dihydrouracil, and 5-bromouracil. The purine or pyrimidine may be substituted as is known in the art, e.g., with halogen (i.e., fluoro, bromo, chloro, or iodo), alkyl (e.g., methyl, ethyl, or propyl), acyl (e.g., acetyl), or amine or hydroxyl protecting groups. Other non-natural bases, e.g., universal bases such as 5-nitro indole, may also be employed.

Exemplary materials includes a filter, a matrix, a polymer, a charge switch material, a gel, and a membrane (e.g., a silica membrane, a glass-fiber membrane, a cellulose membrane, a nitrocellulose membrane, a polysulfone membrane, a nylon membrane, a polyvinylidene difluoride membrane, a vinyl copolymer membrane, or an ion exchange membrane, including any described herein), a fiber (e.g., a glass fiber), or a particle (e.g., a silica particle, a bead, an affinity resin, or an ion exchange resin).

In some embodiments, the binding agent includes a bead or a particle. For instance, such beads or particles can be included in one or more first regions and/or one or more second regions to provide a spatial array of encoded beads or particles. In particular embodiments, multiplex analysis can be achieved using spatial encoding in these devices (e.g., any device described herein). In particular embodiments, the beads or particles can include a barcode, a color (e.g., fluorometric or spectrophotometric label), or combinations thereof for further encoding.

In some embodiments, the binding agent includes a silica-based material. Such silica-based materials can be useful for silica-based isolation procedures to capture a target (e.g., a nucleic acid) by virtue varying adsorption depending on the solute. For example, nucleic acids exhibit high adsorption in the presence of high concentrations of chaotropic salts (e.g., sodium iodide, sodium perchlorate, guanidinium thiocyanate, and guanidinium hydrochloride). Then the nucleic acid can be eluted by removal of the chaotropic salts with an alcohol based wash (e.g., ethanol) followed by a buffer (e.g., TE buffer) or water. Exemplary silica-based materials include silica membranes, silica structures (e.g., silica channels on microchips), silica particles (e.g., beads, resins), glass particles, diatoms, and silica-coated paramagnetic particles (e.g., Magnesil®). Such materials and procedures are commercially available, such as in Wizard® Technology (available from Promega) and NucleoSpin® Technology (available from Macherey-Nagel).

In some embodiments, the binding agent includes a magnetic material (e.g., magnetic beads) that can be used in isolation procedures to capture a target (e.g., nucleic acids). Under optimized conditions, targets selectively bind to the surface of magnetic beads. Magnetic beads can be coated with other materials (e.g., silica, agarose, charge switch material) to enhance binding to targets. Such materials and procedures are commercially available, such as in Magne-Sil® Technology (available from Promega) and Megarose® Technology (available from Whatman).

Binding agents may be specific for a molecule (e.g., a specific nucleic acid sequence or protein isoform), cell, etc. or to a class of molecules (e.g., nucleic acids or proteins), cell (e.g., white blood cell or bacterial cell), etc. The binding agent employed at one location may be the same or different from the binding agent employed at a second location. That is, the devices of the system may be employed for multiple assays of a sample for the same target, for multiple assays for different targets in a sample, or a combination thereof. For example, the devices may be used to assay for multiple nucleic acids in a sample. In addition, as the locations are spatially separated and known, the same reagent, e.g., fluorophore or chromophore, may be used to detect the presence or absence of a target. That is, the spatial location identifies the target being assayed, and the reagent determines the presence or absence of the target. Such embodiments greatly simplify the detection system requirements.

The number of locations used, either with the same or different binding agent may be any desired number, e.g., at least 10, 50, 100, 250, 500, 1000, 10,0000, 100,000, 1,000,000 or even higher. The capture region can include any useful dimension. In particular embodiments, the capture region has one or more dimensions that are less than about 1,000 μm.

Binding agents can be placed in specified locations and bound to the surface using methods known in the art. Alternatively, the binding agent may form all or part of the structure of the location.

Such capture regions and binding agents could allow for multiplex analysis. In particular embodiments, the device of the invention includes one or more arrays of such capture regions or binding agents (e.g., within an array of regions provided in FIGS. 8, 10A-10E, 11A-11C, 12A-12B, and 17-19). Further binding agents and processes, as well as multiplex analysis, are described in U.S. Pat. Nos. 5,658,548, 5,705,628, 5,808,041, 6,162,356, 7,429,470, 7,601,497, 7,718,262, 7,955,801, 8,283,037, and 8,323,899; U.S. Pub. Nos. 2005/142565, 2006/094051, 2006/110725, 2006/159962, 2007/015188, 2007/238114, 2007/221563, 2008/038725, 2008/318279, 2008/132694, 2008/161553, 2008/166703, 2010/178709, 2010/285578, 2010/190240, 2010/036104, 2011/059442, 2011/059866, 2011/177588, 2011/183325, 2012/214168, and 2013/030163; and; and Int. Pub. No. WO 03097831, each of which is incorporated by reference in its entirety.

Such capture regions or binding agents could be included in any portion of the device. For instance, the capture region can be included on the surface of any region described herein, within any region described herein, or both on and within any region described herein (e.g., capture regions can be included on the surface of a first region, within a first region, or both within and on the surface of a first region). In some embodiments, the capture regions could be on the surface of first regions (e.g., as a thin layer, like a hydrogel, or as a surface monolayer as in some hybridization assays) or could be filling a substantial part of the first region (e.g., a capture hydrogel or some other 3D matrix within a first chamber). Such capture regions or binding agents can be included in any layer, such as the first, second, third, or additional layers.

In some embodiments, the capture region includes a charge switch material having an ionizable group that changes charge based on ambient conditions. Such charge switch materials can be useful for ion exchange procedures to capture a target (e.g., a negatively charged target, such as a nucleic acid) with a charge switch material having positive charge at low pH (e.g., a pH<6.0 or 6.5 or a pH lower than or equal to the pKa of the ionizable group). Then, the target can be eluted by releasing it from the charge switch material, such as by elution at a raised pH (e.g., a pH≥8.5 or a pH higher than the pKa of the ionizable group). Exemplary charge switch materials include those with an ionizable group selected from a biological buffer (e.g., -2-acetamido-2-aminoethanesulfonic acid (ACES); N-2-acetamido-2-iminodiacetic acid (ADA); amino methyl propanediol (AMP); 3-1,1-dimethyl-2-hydroxyethylamino-2-hydroxy propanesulfonic acid (AMPSO); N,N-bis2-hydroxyethyl-2-aminoethanesulfonic acid (BES); N,N-bis-2-hydroxyethylglycine (BICINE); bis-2-hydroxyethyliminotrishydroxymethylmethane (Bis-Tris); 1,3-bistrishydroxymethylmethylaminopropane (Bis-Tris Propane); 4-cyclohexylamino-1-butane sulfonic acid (CABS); 3-cyclohexylamino-1-propane sulfonic acid (CAPS); 3-cyclohexylamino-2-hydroxy-1-propane sulfonic acid (CAPSO); 2-N-cyclohexylaminoethanesulfonic acid (CHES); 3-N,N-bis-2-hydroxyethylamino-2-hydroxypropanesulfonic acid (DIPSO); -2-hydroxyethylpiperazine-N-3-propanesulfonic acid (EPPS); -2-hydroxyethylpiperazine-N-4-butanesulfonic acid (HEPBS); -2-hydroxyethylpiperazine-N-2-ethanesulfonic acid (HEPES); -2-hydroxyethylpiperazine-N-2-propanesulfonic acid (HEPPSO); 2-N-morpholinoethanesulfonic acid (MES); 4-N-morpholinobutanesulfonic acid (MOBS); 3-N-morpholinopropanesulfonic acid (MOPS); 3-N-morpholino-2-hydroxypropanesulfonic acid (MOPSO); piperazine-N—N-bis-2-ethanesulfonic acid (PIPES); piperazine-N—N-bis-2-hydroxypropanesulfonic acid (POPSO); N-trishydroxymethyl-methyl-4-aminobutanesulfonic acid (TABS); N-trishydroxymethyl-methyl-3-aminopropanesulfonic acid (TAPS); 3-N-trishydroxymethyl-methylamino-2-hydroxypropanesulfonic acid (TAPSO); N-trishydroxymethyl-methyl-2-aminoethanesulfonic acid (TES); N-trishydroxymethylmethylglycine (TRICINE); trishydroxymethylaminomethane (Tris); polyhydroxylated imidazoles; triethanolamine dimers and polymers; and di/tri/oligo amino acids, for example Gly-Gly, Ser-Ser, Gly-Gly-Gly, and Ser-Gly), a polyhydroxylated amine (e.g., TRIS or Bis-Tris), imidazole, histidine, and polyhistidine. In some embodiments, the charge switch material can include Bis-Tris, a Bis-Tris polymer (e.g., formed by attachment of Bis-Tris monomers to a polyacrylic acid (PAA) backbone), PAA, or a combination of Bis-Tris and PAA (e.g., where both Bis-Tris and PAA are in polymeric form and can formed as a co-polymer or as layers including alternating Bis-Tris and PAA layers). In other embodiments, the charge switch material is a weakly basic polymer that has a cationic charge at acidic pH but has a neutral charge at basic pH. Such materials include poly[N-(3-imidazolylpropyl)methacrylamide hydrochloride-co-acrylamide], poly[N-(3-imidazolylpropyl)methacrylamide hydrochloride-co-2-hydroxyethyl methacrylate], poly(-vinylimidazole), poly(2-aminoethyl methacrylate hydrochloride-co-2-hydroxyethyl methacrylate), poly(1-vinylimidazole-co-2-hydroxyethyl methacrylate), poly[N-(1,1-dimethyl-3-imidazolylpropyl)acrylamide], or poly(N-2-methyl-1-vinylimidazole. Additional charge switch materials include those that are pH-insensitive but targets charge changes. Further charge switch materials are described in U.S. Pat. Nos. 5,582,988, 6,914,137 and 7,319,004, each of which is incorporated herein by reference.

Such materials and procedures are commercially available, such as in ChargeSwitch® Technology (available in numerous formats from Invitrogen Corp. or Life Technologies™ Corp., Carlsbad, Calif., such as in a ChargeSwitch® coated membrane, magnetic bead, or well plate). Further charge switch materials and/or ion exchange processes are described in U.S. Pat. Nos. 5,234,809, 6,718,742, 6,914,137, and 7,319,004; U.S. Pub. Nos. 2003/0008320, 2005/0053941, 2003/0054395, 2003/0173284, 2003/0130499, 2005/0053941, 2006/0154247, 2006/0263780, 2007/0122809, 2006/0024712, 2012/0196944, and 2012/0197009; and Int. Pub. Nos. WO 02/48164, WO 99/29703, WO 01/88185, WO 01/03149, WO 03/101494, WO 03/046177, WO 2005/012521, and WO 2006/004611, each of which is incorporated by reference in its entirety.

Movement of Layers

The devices of the invention include layers that allow for connection and disconnection of one or more chambers by relative movement. For example, in a first position, a first chamber is not connected to a second chamber (i.e., the first chamber does not fluidically communicate with the second chamber). Upon moving the first chamber relative to the second chamber, a connection is formed. This movement can be accomplished by moving the first layer having the first chamber relative to the second layer. Alternatively, this movement can include moving the second layer having the second chamber relative to the second layer. The connection between chambers can also occur via a channel, a bridge, a membrane, or any other structure described to provide fluidic communication between a first and second chamber.

Figure 7:
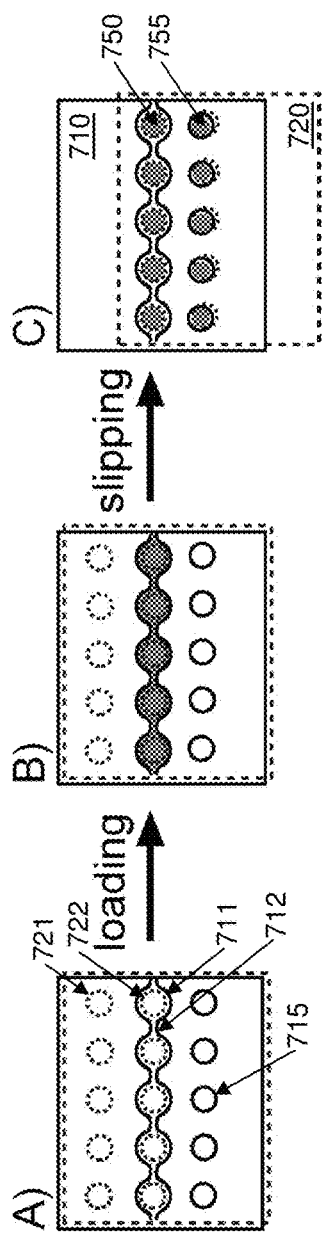
FIGS. 7A-7C provide schemes describing compartmentalization driven by surface tension and physical separation. The solid line indicates the top layer 710 having chambers 711 connected by a neck or channel 712 and receiving chambers 715, and the dotted line indicates the bottom layer 720 having receiving chambers 721 and additional receiving chambers 722. After slipping, samples can be compartmentalized in droplets 750 (in the connected chambers 711) or in separated chambers 715, where compartmentalized samples 755 can either be in the form of droplets (e.g., surrounded by a lubricant or an immiscible fluid, as described herein) or in the form of a solution surrounded by air.

The movement can be any useful relative movement. For instance, such movement can include axial rotation of two or more layers on the same axis or rotation of two or more layers on different axes. For example, the device can include two layers, each having a cylindrical, generally planar surface (e.g., layers 810 and 820 in FIG. 8). Relative movement of layer 810 on an axis results in axial rotation of layer 810 relative to layer 820. In another instance, such movement can include longitudinal translation between two or more layers. For example, the device can include two layers (e.g., top layer 710 and bottom layer 720 in FIG. 7). Relative movement of layer 720 in the downward direction results in longitudinal translation of layer 720 relative to layer 710. In yet another instance, the movement can be a combination of axial rotation and longitudinal translation.

Accordingly, the relative movement may be linear, rotational, or a combination of both. In some instances, two-dimensional motion (e.g., X-Y motion) may be accomplished through a combination of linear and/or rotational movements. For example, sliding and rotating means may be employed to effect linear and rotational sliding motion. In addition, such means for producing relative sliding motion may be constructed from, for example, motors, levers, pulleys, gears, hydraulics, pneumatics, a combination thereof, or other electromechanical or mechanical means known to one of ordinary skill in the art. Other examples of methods of controlling the motion of one part relative to another include, but are not limited to, sliding guides, rack and pinion systems (U.S. Pat. No. 7,136,688), rotational plates (U.S. Pat. No. 7,003,104), slider assemblies (U.S. Pub. Nos. 2007-0155451 and 2008-0058039), guide grooves (U.S. Pat. Nos. 5,805,947 and 5,026,113), piezoelectric actuators (U.S. Pub. No. 2005-0009582), ball bearings and notches (U.S. Pat. No. 2,541,413), and drive cables (U.S. Pat. No. 5,114,208), each of which is incorporated herein by reference in its entirety. Moreover, motion of layers relative to one another may be constrained by notches, retainers, and/or a system of holes and mating pins, for example, as are typically used alone or in combination in electrical connectors. Also, the motion of the layers relative to one another may be constrained by a case, posts, grooves and ridges, gears, or, for example in the case of rotational motion, a central axis. In certain embodiments, the device is configured to be manipulated by a robot.

For any of the layers described herein, the distance between layers may vary depending on the type of substrate. In certain embodiments, the distance may vary in different device positions, for example due to design or surface roughness. Generally speaking, the gap may range anywhere from 0.2 nanometers to 20 micrometers. In particular embodiments, the gap between layers is filled with any useful lubricant, such as those described herein.

The structures within the device and/or layers can be designed to accommodate the relative movement to be exerted. For instance, when rotation movement is used to connect or disconnect the layers, then the structural elements (e.g., chambers or channels) within the layer can be arrayed in a radial or spiral pattern.

Relative movement can be effected by any useful assembly. Exemplary assemblies for rotation include a rotary joint mechanism, a rotational actuation mechanism (e.g., employing a pull string for rotational actuation), and a rotational shaft assembly. The rotational motion may be achieved by standard mechanisms, including motors, springs, e.g., clock springs, pull strings, bearings, cams, rotatable hubs, cable elements, gears, and/or actuators. These mechanisms can be designed to control the number, force, and/or speed of rotations. The device may be designed to be activated only once, or it may be used indefinitely. The device may include one or more switches to prevent actuation prior to use. Switches may be disposed on the surface of the device, cap, or lid to ensure proper contact between these structures. Translation between layers may be guided by a guide/track configuration, or a ball bearing configured to slidingly engage the layers in order to limit the direction and amount of relative movement. In addition, the relative movement between the layers may be automated (e.g., using any useful mechanism, such as those described herein).

In one exemplary rotary joint mechanism, a rotatable layer is connected with a fixed layer. To achieve rotation, the rotatable layer can include an outer bearing (e.g., an outer ring bearing), and the fixed layer can include an inner bearing (e.g., an inner ring bearing), where these bearings allow for the outer bearing to rotate with respect to the inner bearing. Such bearing can include or be coupled to at least one motor (e.g., through a cable element, gear mechanism, etc.). Another exemplary assembly includes a stationary shaft interconnected to a base that is included in a fixed layer, and a rotatable layer that includes a hub rotatably interconnected to the stationary shaft. The hub can be supported in axial and radial directions by a bearing (e.g., oil- or air-filled bearing). The rotatable layer can include or be coupled to at least one motor (e.g., through a cable element, gear mechanism, etc.). The motor can be an actuator of any type, e.g., electrical motor, electroactive polymer, galvanometer actuator, hydraulic piston, microelectromechanical system (MEMS) actuator, piezoelectric actuator, relay, or stepper motor.

Relative movement can be effected by any useful autonomous controller. The autonomous controller can include any mechanism or assembly described herein. An autonomous controller can be useful for controlling the operations of a SlipChip, a thin-film SlipChip, or another device. Various functions can be part of the design of the controller to provide a hands-off interface for untrained user. These include, but are not limited to (1) pumping, (2) slipping, and (3) timing control of the first two operations and any of the device's operations. For example, multi-step pumping and slipping can be programmed by using the timing control. These operations may also be performed, for example, without the need of an energy source stored in the SlipChip devices (such as, for example, a battery).

In particular embodiments, the autonomous controller allows for controlling one or more processes (e.g., any described herein) without user input. For instance, such control can be effected by turning on a switch, which activates the autonomous controller. In some embodiments, the controller includes one or more elements that allow for hand-held or portable use. For instance, any of the components herein (e.g., a power element; a regulating element; a timing element; a moving element; a transfer element; a switch; and/or a linkage) can be provided in a miniaturized format that uses minimal power or no external power source.

Autonomous controllers (e.g., in combination with a pressure capping system, a sample loading system, a housing system, cell phone detection, as well as integration for devices and systems, such as those in FIGS. 45-48 and 53 in the following applications) include those described in U.S. patent application Ser. No. 13/868,009, filed Apr. 22, 2013, and Ser. No. 13/868,028, filed Apr. 22, 2013, each of which is incorporated herein in its entirety.

Lubricant

The devices and methods can include any useful lubricant. In some embodiments, the lubricant facilitates movement of the first, second, and/or intermediate layers and/or minimizes contamination between the first, second, and/or intermediate layers or chambers within these layers.

In addition, the lubricant can be selected to be substantially inert with respect to the substances (e.g., reagents and/or samples) that will be in contact with and/or transported through the device. For instance, the lubricant can optionally be a fluid that is substantially immiscible with the reagent(s) and/or sample(s). The lubricant can optionally be selected to have physical characteristics that promote compartmentalization of the reagent(s) and/or sample(s). For instance, the layers and/or chambers can be fluorophilic, and the lubricant can be a fluorous liquid. In this example, compartmentalization occurs by competing surface characteristics, where surface tension results in separating reagent and/or sample fluids into separate plugs or droplets encapsulated by the lubricant.

Exemplary lubricants include a gas (e.g., air), a hydrocarbon, a fluorous substance, an ionic liquid, a non-Newtonian fluid, or a lubricating powder or bead. Exemplary hydrocarbons include alkanes, paraffin oils, hexane, hexadecane, silicon oil, greases (e.g., Dow Corning high vacuum grease, Fomblin vacuum grease, Krytox greases), mineral oil, and other organic materials or polymers, as well as mixtures thereof. Exemplary fluorous substances include fluorocarbons (including perfluorinated and semifluorinated alkanes, e.g., octadecafluoro-decahydronaphthalene and perfluorooctylethane), alkyl and aryl fluorocarbons, halofluorocarbons (e.g., perfluorooctyl bromide), fluorinated alcohols (e.g., 1-(1,2,2,3,3,4,4,5,5,6,6-undeca-fluorocyclohexyl)ethanol or $C_6F_{11}C_2H_4OH$), fluorinated oils, liquid fluoropolymers (e.g., perfluoropolyethers), Fluorinert (3M), Krytox oils, Fomblin oils, and Demnum oils.

Ionic liquids include a cation and an anion, which form a salt and are in a liquid state. Exemplary cations include choline; imidazolium-based cations, such as optionally substituted imidazolium-based cations (e.g., 1-$C_{1-10}$ alkyl-3-$C_{1-10}$ alkyl-imidazolium, (3-$C_{1-10}$ alkyl-imidazolium-1-yl)-$C_{1-10}$alkanol, or 1-$C_{1-10}$ alkyl-2,3-di-$C_{1-10}$ alkyl-imidazolium, such as 1-$C_{1-10}$ alkyl-3-methyl-imidazolium, (3-methylimidazolium-1-yl)-$C_{1-10}$alkanol, or 1-$C_{1-10}$ alkyl-2,3-dimethylimidazolium) or bicyclic imidazolium-based cations (e.g., optionally substituted 2,3-$(CH_2)_{2-6}$-imidazolium, such as 1-alkyl-2,3-trimethyleneimidazolium or 1-alkyl-2,3-tetramethyleneimidazolium); pyridinium-based cations, such as 1-$C_{1-10}$ alkyl-pyridinium; pyrrolidinium-based cations, such as 1-$R_1$-1-$R_2$-pyrrolidinium, where each of $R_1$ and $R_2$ is independently $C_{1-10}$ alkyl; ammonium-based cations, such as $NRiR_2R_3R_4$, where each of $R_1$, $R_2$, $R_3$, and $R_4$ is independently $C_{1-10}$ alkyl; and phosphonium-based cations, such as $PR_1R_2R_3R_4$, where each of $R_1$, $R_2$, $R_3$, and $R_4$ is independently $C_{1-10}$ alkyl. Exemplary anions (e.g., such as X for any ionic liquid described herein) include a halogen (e.g., fluoride, bromide, chloride, or iodide); a phosphate anion (e.g., hexafluorophosphate [$PF_6$], dihydrogen phosphate [dhp], or tris(pentafluoroethyl) trifluorophosphate [FAP]); a borate anion (e.g., tetracyanoborate [TCB], tetrafluoroborate [$BF_4$], or bis(oxalato)borate [BOB]); a sulfonylimide anion $N(SO_2C_nF_{2n+1})(SO_2C_mF_{2m+1})$, where each of n and m is, independently, an integer between 1 to 10, and optionally n=m, such as bis(trifluoromethanesulfonyl)imide ($N(SO_2CF_3)_2$ or [TFSI]) or bis(perfluoroethanesulfonyl)imide ($N(SO_2C_2F_5)_2$; [BETI] or [PFSI]); a sulfonate anion (e.g., triflate [$SO_3CF_3$], mesylate [$SO_3CH_3$], or tosylate [$SO_3C_6H_4CH_3$]); an alkylsulfate anion (e.g., $C_{1-10}$ alkyl-$OSO_3$); a cyanimide anion (e.g., [$(CN)_2N$]); or a carboxylate anion (e.g., formate, acetate, lactate, oxalate, citrate, malate, glycolate, or saccharinate).

Exemplary ionic liquids include choline ionic liquids (e.g., choline dihydrogen phosphate (choline dhp) or choline saccharinate); 1-alkyl-3-methylimidazolium [R-mim] ionic liquids (e.g., such as 1-alkyl-3-methylimidazolium anion [R-mim][α] ionic liquids, including 1,3-dimethylimidazolium iodide, 1-ethyl-3-methylimidazolium bromide, 1-propyl-3-methylimidazolium bromide, 1-propyl-3-methylimidazolium chloride, 1-propyl-3-methylimidazolium bis(trifluoromethanesulfonyl)imide, 1-propyl-3-methylimidazolium bis(perfluoroethanesulfonyl)imide, 1-butyl-3-methylimidazolium bromide, 1-butyl-3-methylimidazolium chloride, 1-butyl-3-methylimidazolium bis(trifluoromethanesulfonyl)imide, 1-butyl-3-methylimidazolium bis(perfluoroethanesulfonyl)imide, 1-pentyl-3-methylimidazolium bromide, 1-hexyl-3-methylimidazolium bromide, 1-heptyl-3-methylimidazolium bromide, 1-octyl-3-methylimidazolium bromide, or 1-nonyl-3-methylimidazolium bromide); (3-methylimidazolium-1-yl)alkanol [ROH-mim] ionic liquids (e.g., such as (3-methylimidazolium-1-yl)alkanol anion [ROH-mim][α] ionic liquids, including 3-(3-methylimidazol-3-ium-1-yl)propan-1-ol bromide, 3-(3-methylimidazol-3-ium-1-yl)propan-1-ol chloride, 4-(3-methylimidazol-3-ium-1-yl)butan-1-ol bromide, 5-(3-methylimidazol-3-ium-1-yl)pentan-1-ol bromide, or 6-(3-methylimidazol-3-ium-1-yl)hexan-1-ol bromide); 1-alkyl-2,3-dimethylimidazolium [R-dmim] ionic liquids (e.g., such as 1-alkyl-2,3-dimethylimidazolium anion [R-dmim][α] ionic liquids, including 1,2,3-trimethylimidazolium iodide, 1-ethyl-2,3-dimethylimidazolium bromide, 1-propyl-2,3-dimethylimidazolium bromide, 1-butyl-2,3-dimethylimidazolium bromide, 1-pentyl-2,3-dimethylimidazolium bromide, 1-hexyl-2,3-dimethylimidazolium bromide, 1-heptyl-2,3-dimethylimidazolium bromide, 1-octyl-2,3-dimethylimidazolium bromide, or 1-nonyl-2,3-dimethylimidazolium bromide); 1-alkyl-2,3-trimethyleneimidazolium [R-3C-im] ionic liquids (e.g., such as 1-alkyl-2,3-trimethyleneimidazolium anion [R-3C-im] [α] ionic liquids, including 1-methyl-2,3-trimethyleneimidazolium iodide, 1-ethyl-2,3-dimethyleneimidazolium bromide, 1-propyl-2,3-dimethyleneimidazolium bromide, 1-butyl-2,3-dimethyleneimidazolium bromide, 1-pentyl-2,3-dimethyleneimidazolium bromide, or 1-hexyl-2,3-dimethyleneimidazolium bromide); 1-alkyl-2,3-tetramethyleneimidazolium [R-4C-im] ionic liquids (e.g., such as 1-alkyl-2,3-tetramethyleneimidazolium anion [R-4C-im] [α] ionic liquids, including 1-methyl-2,3-tetramethyleneimidazolium iodide, 1-ethyl-2,3-tetramethyleneimidazolium bromide, 1-propyl-2,3-tetramethyleneimidazolium bromide, 1-butyl-2,3-tetramethyleneimidazolium bromide, 1-pentyl-2,3-tetramethyleneimidazolium bromide, or 1-hexyl-2,3-tetramethyleneimidazolium bromide); and 1-butyl-3-methylimidazolium [Bmim] ionic liquids (e.g., such as 1-butyl-3-methylimidazolium anion [Bmim] [α]

ionic liquids, including 1-butyl-3-methylimidazolium hexafluorophosphate (Bmim $PF_6$) or 1-butyl 3-methylimidazolium lactate (Bmim lactate)).

In particular embodiments, the following ionic liquids can be used in combination with a nucleic acid (e.g., DNA and/or RNA): 1-alkyl-3-methylimidazolium [R-mim] ionic liquids (e.g., such as [R-mim][α] ionic liquids or any described herein); (3-methylimidazolium-1-yl)alkanol [ROH-mim] ionic liquids (e.g., such as [ROH-mim][α] ionic liquids or any described herein); 1-alkyl-2,3-dimethylimidazolium [R-dmim] ionic liquids (e.g., such as [R-dmim][α] ionic liquids or any described herein); [R-3C-im] ionic liquids (e.g., such as [R-3C-im][α] ionic liquids or any described herein); [R-4C-im] ionic liquids (e.g., such as [R-4C-im][α] ionic liquids or any described herein); or [Bmim] ionic liquids (e.g., [Bmim][α] ionic liquids or any described herein). Further ionic liquid are described in Shi et al., Chem. Commun. 48:5325-5327 (2012), Wang et al., Anal. Chem. 79:620-625 (2007), and Fukaya et al., AE1—Fourteenth International Symposium on Molten Salts Joint International Meeting, Oct. 3-Oct. 8, 2004, "Evaluation of a series of imidazolium based ionic liquids as solvents for nucleic acids," Abstract 2437, each of which is incorporated herein by reference in its entirety.

Exemplary non-Newtonian fluids include shear-thickening fluids, gels, including hydrogels, and carbohydrate-rich or lipid-rich phases, including lipidic cubic phase and other lipid mesophases. In some embodiments, permeability to gases may be desirable, for example in some applications that use live cells and tissues inside the device. Exemplary lubricating powders or beads include various Teflon® beads or powders (e.g., composed of PTFE (poly(1,1,2,2-tetrafluoroethylene), PFA (perfluoroalkoxy copolymer resin), or FEP (fluorinated ethylene propylene resin)), graphite, molybdenum disulfide, or tungsten disulfide. Any of these lubricants can optionally include one or more surfactants, for example to cause or prevent surface aggregation and/or to influence the stability of substances.

Exemplary lubricants include those described in U.S. patent application Ser. No. 13/868,009, filed Apr. 22, 2013, and Ser. No. 13/868,028, filed Apr. 22, 2013, each of which is incorporated herein in its entirety.

Immiscible Fluid

The devices and methods can include any useful immiscible fluid. In some embodiments, the immiscible fluid facilitates compartmentalization of one or more substances (e.g., a sample, a reagent, or any other useful substance, as described herein) in one or more first, second, and/or intermediate layers or chambers within these layers. In other embodiments, the immiscible fluid facilitates flow through one or more capture regions (e.g., as described herein).

An immiscible fluid is a fluid (e.g., a gas or a liquid) that is immiscible with one or more of the second fluids at certain ranges of temperature, pressure, and composition useful for storing, preserving, processing, or analyzing the sample. In some embodiments, the second fluid is an aqueous solution, a sample for storage, preservation, processing, or analysis, and/or a reagent for storing, preserving, processing, or analyzing the sample. In other embodiments, the fluid is immiscible with water or an aqueous solution.

Miscibility can be tested with any useful method under useful conditions for temperature, pressure, and composition. Generally, these useful conditions will be similar to those useful for sample storage, preservation, processing, or analysis. Useful temperature and pressure conditions include those for maintaining stability of the desired sample to be tested and/or the reagent(s) for use with this sample (e.g., a temperature of from about −80° C. to about 150° C., as well as any ranges therein, and a pressure generally of about 1 atm), as well as those for conducting the storage, preservation, processing, or analysis methods described herein. For instance, when the sample is a human blood sample, this sample should be maintained at or below the physiological temperature of about 37° C. Thus, useful immiscible fluids can be tested at a range of from about −80° C. to about 40° C. Further, if the human blood sample includes one or more nucleic acids that require additional analysis (e.g., by PCR requiring thermocycling at increased temperature of >90° C.), then useful immiscible fluids can be tested at a range from about −80° C. to about 100° C. Useful compositions include various ratios of the fluid to be tested for immiscibility in a mixture with a test sample, reagent, or substance, such as ratios to be used within the device for sample storage, preservation, processing, or analysis.

Methods for testing miscibility include, but are not limited to, light scattering, X-ray scattering, and/or neutron scattering to determine whether a single phase is present in a mixture (indicating miscibility) or multiple phases are present in a mixture (indicating immiscibility).

Exemplary immiscible fluids include ionic fluids, aqueous—aqueous immiscible fluids., oils, fluorocarbons, etc, as well as any lubricant described herein.

The immiscible fluid can be used as a component of any fluid, solution, or buffer described herein. For instance, the immiscible fluid can be included in one or more of a lubricant, a washing buffer, and/or an elution buffer. In some embodiments, the elution buffer (e.g., as described herein, such as for sample preparation) includes one or more immiscible fluids. For example, the immiscible fluid can be used to elute small volumes (e.g., about 750 μL, 500 μL, 250 μL, 100 μL, 50 μL, 10 μL, 5 μL, 1 μL, 750 nL, 500 nL, 250 nL, 100 nL, 50 nL, 10 nL, 5 nL, 1 nL, 750 pL, 500 pL, 250 pL, 100 pL, 50 pL, 10 pL, 5 pL, 1 pL, 750 fL, 500 fL, 250 fL, 100 fL, 50 fL, 10 fL, 5 fL, 1 fL, 750 aL, 500 aL, 250 aL, 100 aL, 50 aL, 10 aL, 5 aL, or 1 aL, including any ranges for these values, as described herein) from a chamber or a capture region. In one non-limiting embodiment, the elution buffer including one or more immiscible fluids (e.g., one or more ionic fluids, such as any described herein) removes water from the substance passing through the capture region. For example, the method includes filling or adding an elution buffer (e.g. including one or more immiscible fluids, such as an ionic liquid) to one or more capture regions, thereby removing and/or capturing an eluent (e.g., water, a target, an analyte, a nucleic acid, a sample, an impurity, etc.) with the elution buffer (e.g., immiscible fluid). In yet other non-limiting embodiments, the elution buffer including one or more immiscible fluids (e.g., one or more ionic fluids, such as any described herein) extracts an analyte (e.g., a nucleic acid, a target, a protein, an impurity, or any useful component of a sample).

Exemplary immiscible fluids include those described in U.S. patent application Ser. No. 13/868,009, filed Apr. 22, 2013, and Ser. No. 13/868,028, filed Apr. 22, 2013, each of which is incorporated herein in its entirety.

Moving Substances within Devices

The devices of the invention can include the use of one or more forces or gradients to move one or more substances within the device. A pressure gradient can be created by any component described herein, such as the capping system described herein. The devices herein can optionally include posts or other three-dimensional structures that partially or completely block a chamber and/or channel. For example, a post member is provided in a first layer, which blocks a chamber in a second layer upon moving the first layer relative to the second layer. In this manner, positive pressure may be generated in front of the post member and negative pressure may be generated behind. It may be used to load, dispose, or move a substance within the device. Flow may also be generated by the pressure gradient created by the relative movement.

Exemplary, non-limiting forces and gradients include use of centrifugal force; a surface tension gradient; osmotic pressure; capillary pressure, such as by including arrays of channels and/or chambers to create gradients of capillary pressure; positive or negative pressure that can be generated externally, for example by using pumps or syringes; slipping, such as by relative movement of one or more layers; pressure generated by compressing or expanding a chamber containing a fluid; an electric force; an electroosmotic force; gravity; a magnetic force; or a chemical reaction or process (e.g., by using reagents to produce a gaseous product, thereby generating pressure, such as the combination of sulfuric acid with a carbonate salt or the combination of sodium bicarbonate with a solid acid, for example tartaric acid, activated by addition of water; or by using reagents that consume gas, thereby causing a decrease in pressure, such as the combination of sodium hydroxide with carbon dioxide), which may be initiated externally or initiated by relative movement (e.g., by slipping). Further methods and devices for filling or loading fluids are described herein.

Target Fluids, including Samples and Reagents

The devices and methods of the invention can be used with any useful target fluids (e.g., a sample, a reagent, any other fluid described herein, as well as combinations thereof).

Samples can be obtained from a subject (e.g., human subject), a food sample (e.g., including an organism), or an environmental sample (e.g., including one or more organisms). Exemplary, non-limiting samples include blood, plasma, serum, sputum, urine, fecal matter (e.g., stool sample), swab, sweat, spinal fluid, amniotic fluid, interstitial fluid, tear fluid, bone marrow, tissue sample (e.g., a skin sample or a biopsy sample), a buccal mouthwash sample, an aerosol (e.g., produced by coughing), nucleic acid, cell (e.g., tumor cells, fetal cells in blood, stem cells, bacterial and fungal cells, T-cells, or B-cells), protein, enzyme, soil, water, compost pile, manure pile, sediment (e.g., marine or freshwater sediment), a water sample, an air sample, rock, a plant sample, a food sample, or a gut sample. The sample can include any useful target or analyte to be detected, filtered, concentrated, and/or processed.

Any analyte of interest can be present in the sample. Such analytes could be processed, captured, preserved, and/or removed for further analysis, treatment, reaction, and/or detection. Exemplary analytes include those described herein, such as those present in a test sample (e.g., any described herein), as well as one or more of the following: a protein (e.g., one or more antibodies such as Epstein-Barr virus (EBV) antibodies, hepatitis antigen/antibodies (e.g., hepatitis A, B, or C), or HIV antibodies, C-reactive protein (CRP), apolipoprotein (e.g., A-I or B), IGFBP-2, IGFB-3, transferrin receptor, lipoprotein (e.g., (a), B/A-1, or β), thyroglobulin, or hemoglobin (e.g., including glycosylated hemoglobin or HbA1c)), a nucleic acid (e.g., RNA or DNA), a cell (e.g., CD4+ lymphocyte), a virus (e.g., a whole virus, including HIV, CMV, hepatitis C virus, hepatitis B virus, hepatitis A virus, or herpes simplex virus), a parasite (e.g., *Toxoplasma gondii, Plasmodium falciparum, Trypanosoma cruzi, Giardia lamblia, Leishmania* spp, *Echinococcus granulosus, Schistosoma haematobium*, or *Brugia malayi*), a bacteria (e.g., *Mycobacterium leprae, Helicobacter pylori, Brucella* sp, or *Treponema pallidum*), a cytokine (e.g., IL-1, IL-1b, IL-2, IL-6, IL-7, IL-10, IL-13, IL-17, IFN, IFNg, TNF, or TNF-beta), an antibody (e.g., any herein), a hormone (e.g., estradiol, progesterone, prolactin, cortisol, dehydroepiandrosterone (DHEA, including its sulfate ester, DHEA-S), follicle-stimulating hormone (FSH), thyrotropin (TSH), thyroxine (T4), triiodothyronine (T3), luteinizing hormone (LH), insulin, leptin, sex hormone binding globulin (SHBG), somatomedin-C (IGF-1), testosterone, or androstenedione), an amino acid (e.g., arginine, histidine/urocanic acid, homocysteine, phenylalanine/tyrosine, and/or tryptophan), a drug (including candidate drugs or investigational new drugs for clinical trials), a small molecule (e.g., a peptide or peptoid, folate, or glucose), a contaminant (e.g., Hg, $H_2S$, sulfur oxides, etc.), a gas or vapor (e.g., oxygen, CO, $CO_2$, or any described herein), a volatile component (e.g., a volatile organic compound), an enzyme (e.g., a proteinase, an amylase, a protease, a glucanase, a lipase, a lactase, an amyloglucosidease, a glucoamylase, a protease, an isomerase, a cellulase, a ligninase, a xylanase, a catalase, a polymerase, trypsin, prostate-specific antigen (PSA), iduronidase, acid α-glucocerebrosidase (ABG), acid α-galactosidase A (GLA), lysosomal acid α-glucosidase (GAA), galactocerebroside α-galactosidase (GALC), or acid sphingomyelinase (ASM)), a sterol (e.g., cholesterol (e.g., including total cholesterol or high-density lipoprotein cholesterol (HDL)), or triglycerides).

Such analytes can be preserved (e.g., using any device herein, such as those having one or more membranes and/or bridges), analyzed (e.g., using any device herein, such as those having one or more capture regions), or preserved and analyzed (e.g., using any device herein, such as those having one or more membranes, bridges, and/or capture regions).

The device can be pre-loaded prior to use or subsequently loaded during use with any useful reagents. These reagents could also be included in any feature of the device, such as one or more chambers, layers (including portions thereof, such as, e.g., the portion of the layer lacking one or more chambers), capture regions, bridges, and/or membranes. Furthermore, such reagents can be used in gas, liquid, or solid form, as well as in a coating on the one or more features or in a coating on one or more solid supports (e.g., beads, particles, etc.) within one or more features, where such features include, e.g., one or more chambers, layers (including portions thereof, such as, e.g., the portion of the layer lacking one or more chambers), capture regions, bridges, and/or membranes.

Exemplary reagents include a desiccant (e.g., any described herein), a matrix (e.g., a stabilization matrix, such as any described herein), an organic or inorganic chemical, a compound, a mixture, a solution, an emulsion, a dispersion, a suspension, a molecule, an ion, a dimer, a macromolecule such as a polymer or protein, a nucleic acid, a biomolecule, an oligosaccharide (e.g., trehalose, sucrose, or maltose), an anticoagulant (e.g., heparin, EDTA, citrate, or oxalate), an inhibitor (e.g., to inhibit growth of one or more bacteria and/or other organisms, such as a chelator (e.g., any described herein), an antibiotic, a fluorinated polymer, PEG, albumin, a biocompatible coating (e.g., PDMS), an antifouling agent (e.g., tributyltin), or a biocide), a precipitate, a crystal, a chemical moiety or group, a particle, a nanoparticle, a reaction product, a solvent, a buffer (e.g., a washing buffer (e.g., Tris/EDTA; 70% ethanol; STET (Saline/Tris/EDTA/Triton*X-100 Solution); saline-sodium citrate (SSC) buffer; SSPE (0.2 M phosphate buffer, pH approx. 7.4, containing 2.98 M NaCl, and 0.02 M EDTA); FTA purification reagent, and the like) or an elution buffer (e.g., TRIS/EDTA; TRIS/acetate/EDTA, for example 4 mM Tris-acetate (pH 7.8), 0.1 mM EDTA, and 50 mM NaCl; TRIS/borate; TRIS/borate/EDTA; potassium phosphate/DMSO/glycerol; NaCl/TRIS/EDTA; NaCl/TRIS/EDTA/TWEEN; TRIS/NaCl/TWEEN; phosphate buffers; TRIS buffers; HEPES buffers; nucleic acid amplification buffers; or nucleic acid hybridization buffers)), a lysis agent (e.g., an enzyme (e.g., a lysosyme, a trypsin, proteinase K, or other proteases), a detergent (e.g., Triton X-100 (polyethylene glycol p-(1,1,3,3-tetramethylbutyl)-phenyl ether) or sodium dodecyl sulfate), or a chaotropic substance, such as any described herein), a chelating agent (e.g., diethylenetri-aminepentaacetic acid (DTPA), ethylenediaminetetraacetic acid (EDTA), ethylene glycol tetraacetic acid (EGTA), trans-1,2-diaminocyclohexane-N,N,N',N'-tetraacetic acid (CDTA), 1,2-bis(2-aminophenoxy)ethane-N,N,N',N'-tet-raacetic acid (BAPTA), 1,4,7,10-tetraazacyclododecane-1,4,7,10-tetraacetic acid (DOTA), N-(2-hydroxyethyl)ethylene-diamine-N,N',N'-triacetic acid, or nitrilotriacetic acid (NTA)), a reducing agent (e.g., 2-mercaptoethanol, thiosulfate, TCEP (tris-(2-carboxyethyl)phosphine), dithiothreitol, or dithioerythritol), a dye, a stabilizer, a marker, a salt (e.g., a urate salt), a surfactant (e.g., an anionic surfactant, such as sodium dodecyl sulfate, or a cationic surfactant), a base (e.g., a weak base, such as trishydroxymethyl methane), a fluorophore, or a fluid, any one of which may exist in the solid, liquid, or gaseous state. Further, any of these reagents can be combined with any other useful structure or solid support described herein, such as a filter, a membrane, or a particle, or any described for a capture region. In addition, one or more reagents can be combined in any useful manner.

Exemplary samples, reagents, and desiccants are described in U.S. patent application Ser. No. 13/868,009, filed Apr. 22, 2013, and Ser. No. 13/868,028, filed Apr. 22, 2013, each of which is incorporated herein in its entirety.

Sample Preservation

The devices of the invention can be useful for performing sample (e.g., biospecimen) preservation, such as by sample storage and stabilization in the liquid state or dry state, including molecular (e.g. proteins, nucleic acids) and cellular and multiple biospecimens (e.g., biological fluids and human biological fluids such as blood and plasma). Devices may include optional collection and/or optional sample preparation capabilities. In general, the devices allow for loading a sample, optionally combining the sample with a matrix, storing the resultant sample in the liquid or dry state for a desired time, and then recovering the sample. The matrix (e.g., stabilization matrix) can be liquid or solid, which can optionally be pre-loaded in the device, mixed with the sample prior to loading, or loaded in the device at the same time as the sample or at a different time.

Sample preservation can be performed in the device in any number of ways. In one instance, a highly active and high-capacity desiccant can be preloaded into the device. The device is sealed (e.g., by any useful method, such as those described herein by closing a valve) to prevent the desiccant from absorbing ambient moisture before the sample is loaded. The sample chamber can be optionally pre-coated with a preservative matrix to avoid degradation of the sample during drying and storage. For example, a 10 µL sample can be digitized or partitioned into hundreds of aliquots to make rapid drying and digital analysis both possible. In some embodiments, sample preservation or storage (e.g., where the sample is in a liquid state or a solid state) includes use of one or more matrices (e.g., stabilization matrices). Exemplary matrices are described in U.S. patent application Ser. No. 13/868,009, filed Apr. 22, 2013, and Ser. No. 13/868,028, filed Apr. 22, 2013, each of which is incorporated herein in its entirety.

Liquid sample storage and preservation can be performed using a SlipChip device. A liquid sample (such as blood, saliva, urine, blood plasma, serum, purified protein or nucleic acid solution, cell culture medium, environmental sample etc., or any other described herein) can be loaded in the device. Preservation and storage can be performed by adding an extra drying step. Drying the sample can be done with several strategies, such as by using a device including desiccant and a bridge, a device including desiccant and a porous membrane, a device including a first module having a porous material and a second module having a desiccant, or a device including a module including a porous material that allows for drying under ambient conditions. In some embodiments, a bridge is a channel. In other embodiments, a bridge is a chamber (e.g., a channel) in the intermediate layer, where relative movement connects the bridge to two or more first chambers. In yet other embodiments, a bridge is a chamber (e.g., a channel) in the intermediate layer, where relative movement connects the bridge to the first chamber and the second chamber. In some embodiments, a bridge is a chamber (e.g., a channel) in the intermediate layer, where relative movement connects the bridge to two or more second chambers. Such devices are described (see, e.g., FIGS. 1-9 and 13 in the following applications) in U.S. patent application Ser. No. 13/868,009, filed Apr. 22, 2013, and Ser. No. 13/868,028, filed Apr. 22, 2013, each of which is incorporated herein in its entirety, and allow for a drying strategy that is not dependent on external ambient conditions (such as humidity). The desiccant can be any useful desiccant, e.g., described herein. Furthermore, the drying process can result from water transport occurring through a gas (e.g., air), a liquid (e.g., an immiscible fluid, such as a lubricant or oil), or a solid (e.g., a porous membrane, which can include but are not limited to GoreTex, and porous membranes made of PE, PP, PTFE, PES, PC (commercially available from Millipore and Whatman/General Electrics), as well as any described herein).

The device can be loaded in parallel or in series (see, e.g., FIGS. 10-12 in U.S. patent application Ser. No. 13/868,009, filed Apr. 22, 2013, and Ser. No. 13/868,028, filed Apr. 22, 2013, each of which is incorporated herein in its entirety). The matrices can be preloaded in the device or pre-mixed with the sample. Loading and drying can be achieved simultaneously, in which volume can be controlled by controlling the rate of filling and/or the rate of evaporation. Such an approach can allow for storing sample volumes that are larger than the actual volume of the chambers, if the timescales of loading and drying are comparable.

Loading (e.g., by a lid or cap, as described herein) can incorporate features to irreversibly clip the lid to the main device (e.g., to keep the lid in place during transport and to prevent the user from unintentionally opening the lid after loading). Such features can be added externally (e.g., to a housing, as described n U.S. patent application Ser. No. 13/868,009, filed Apr. 22, 2013, and Ser. No. 13/868,028, filed Apr. 22, 2013, each of which is incorporated herein in its entirety) or to the device itself. Optionally, the lid may include one or more desiccants and/or matrices to dry any excess sample, if present.

In any of the devices herein, samples, analytes, or solutions can be retrieved from a device by connecting a chamber or series of chambers to inlet/outlet holes and then injecting an immiscible fluid (e.g., such as air, gas, mineral oil, a lubricant, etc.) in the chambers so that the samples, analytes, or solutions are pushed out of the device. Alternatively, the samples, analytes, or solutions can be recovered by aspiration through the via holes (e.g., using for example a pipettor, or a low vacuum source). In any of the devices herein, the sample can be rehydrated by injecting a solvent (e.g., water) in the device, and recovery can be performed on all stored samples or only on the sample stored in a particular chamber or subset of chambers. Further, one or more fluids (e.g., a sample, a reagent, a lubricant, or a matrix) can be injected in the device using any useful loading strategy, e.g., any described herein. Alternatively, some fluids can be pre-loaded in the device before assembly, by depositing such fluids (e.g., as droplets or microdroplets) in a set of chambers.

Various strategies can be implemented for drying, preserving, and/or rehydrating samples. In one example, vapor contact can be achieved through shallow empty bridges connecting the sample and the desiccant chambers. In this strategy, the sample to be preserved is digitized in a large number of chambers (e.g., volumes on the order of 10-100 mL). During drying, each sample chamber is connected to another chamber containing a desiccant (e.g., a solid desiccant salt) through a duct ("bridge"). In particular embodiments, the bridge is shallow enough to allow vapor diffusion, while preventing any physical contact between the liquid(s) and/or content(s) of the two chambers.

Exemplary devices, methods, and systems for sample preservation are described in U.S. patent application Ser. No. 13/868,009, filed Apr. 22, 2013, and Ser. No. 13/868,028, filed Apr. 22, 2013, each of which is incorporated herein in its entirety.

Sample Concentration

The devices of the invention can be useful for concentrating one or more samples. The sample and/or one or more analytes within the sample can be concentrated by any useful methods, e.g., evaporation. In one non-limiting embodiment, a sample is injected in the device and then exposed to a desiccant or an external atmosphere via a porous material (e.g. membrane). Here, the solvent of the sample will be removed, thus increasing the concentration of the analytes. In further embodiments, evaporation is used to initiate flow within a device, such as using the principles provided in, e.g., Randall et al., Proc. Natl. Acad. Sci. 102:10813-10818 (2005) and Merline et al., Soft Matter 8:3526-3537 (2012), each of which is incorporated by reference in its entirety.

Evaporation can be controlled by any useful device or method. In one non-limiting embodiment, evaporation results in complete drying of a sample, such as described in FIG. 58. For instance, the solvent for the sample is removed completely, and the resultant analytes are eluted with a known volume of a solution (e.g., water, a buffer, or any fluid described herein). The factor of concentration can be controlled, for example, by controlling the geometry of one or more chambers and/or capture regions. In another non-limiting embodiments, evaporation results in partial drying of a sample. For instance, evaporation occurs in a controlled region of the device for a given time. Then, the resultant concentrated solution can be used for further processing. The factor of concentration can be controlled, for example, by controlling the geometry of one or more chambers and/or capture regions, the total evaporation area (e.g., total area of the membrane exposed to the sample), and/or the evaporation time.

Exemplary devices, methods, and systems for sample concentration (e.g., FIGS. 49-52 and 58-64 in the following applications) are described in U.S. patent application Ser. No. 13/868,009, filed Apr. 22, 2013, and Ser. No. 13/868,028, filed Apr. 22, 2013, each of which is incorporated herein in its entirety.

Sample Treatment

The devices of the invention can be useful for performing sample treatment (e.g., for detoxifying a sample, preserving a sample, analyzing a sample, or determining the reaction progress of a sample). In particular embodiments, the device for sample treatment is any described herein for preserving or storing a sample (e.g., including one or more membranes and/or bridges). In particular embodiments, the device for sample treatment is any described herein for processing or analyzing a sample (e.g., including one or more capture regions).

In some embodiments, the device (e.g., including one or more membranes and/or bridges, as described herein) is useful for removing and/or collecting a vapor or a gas from the sample. In particular embodiments, the device includes a matrix (e.g., a collection matrix with appropriate selectivity for the vapor or gas of interest, or any described herein), where exposure of the sample to the matrix results in removing and/or collecting the vapor or gas of interest. Exemplary vapors and gases include $H_2S$, oxygen (e.g., $O_2$, as well as radical oxygen species), CO, $CO_2$, methane, sulfur oxides, mercury vapors, vapors of volatile organic compounds, carboxylic acids, amines, aldehydes, odorants, etc. In other embodiments, the device includes a matrix (e.g., a collection matrix with appropriate selectivity for one or more physical or chemical properties, such as polarity, size, charge, density, acidity, basicity, hydrophobicity, lipophilicity, or any described herein), where exposure of the sample to the matrix results in removing and/or collecting the analyte of interest having the desired physical or chemical property.

Various types of sample can be used for sample treatment. Exemplary samples include liquid samples (e.g., for the removal of volatile compounds) or gas samples (e.g., for the removal of some compounds from the gas mixture), as well as any described herein. Exemplary sample treatment steps include removing one or more contaminants, such as, for example, one or more toxic components, interfering components, or volatile components (e.g., prior to sample analysis in the device or prior to sample stabilization or preservation in the device), removing substances (e.g., oxygen) for enhancing preservation of such sample, and/or capturing one or more analytes of interest. In any of these embodiments, the matrix can be further analyzed, such as by removing the matrix from the device or by exposing the matrix to one or more elution buffer and analyzing the resultant eluent. In particular non-limiting embodiments, the device is made from materials not permeable or minimally permeable to the vapors being collected. A substantial expertise exists in the industry, for example, in plastic films that reduce oxygen and water vapor permeability. For example, permeability of cyclic olefin copolymer (COC) and cyclic olefin polymer (COP) is generally lower than that of polycarbonate (PC). Exemplary COC and COP include copolymers including norbornene (e.g., with ethene or ethylene), copolymers including tetracyclododecene (e.g., with ethene or ethylene), including TOPAS® COC containing an ethylene-norbornene copolymer (e.g., TOPAS-8007 (Tg=78° C.), TOPAS-5013 (Tg=130° C.), TOPAS-6015 (Tg=160° C.), and TOPAS 6017 (Tg=130° C.)), as well as any described herein.

Exemplary devices, methods, and systems for sample treatment, including collection matrices, are described in U.S. patent application Ser. No. 13/868,009, filed Apr. 22, 2013, and Ser. No. 13/868,028, filed Apr. 22, 2013, each of which is incorporated herein in its entirety.

Sample Preparation

The devices of the invention are useful for methods of processing, preparing, and/or analyzing a sample (e.g., any described herein). Such methods benefit from the devices of the invention, which include one or more layers, one or more chambers, and/or one or more capture regions capable of being connected or disconnected by relative movement. In particular, each step of these methods can be accomplished by controlling such relative movement, where even complicated or reiterated steps can be accommodated by controlling relative movement and by designing appropriate layers. For instance, a particular relative step between reagent(s) and the sample in different layers can be initiated by relatively moving the layers of the device to connect chambers containing the desired reagent(s) and sample.

The methods can further include partitioning a test sample (e.g., having a volume of more than about 1 mL) into separate aliquots (e.g., a plurality of droplets or a plurality of microdroplets each having a volume of less than about 1 mL), drying one or more of the aliquots (e.g., using one or more desiccants, as described herein), and/or recovering one or more of the aliquots (e.g., using one or more solvents, such as water, a buffer, or an organic solvent, as described herein). The volume of each aliquot can be controlled by appropriately sized chambers. Furthermore, such aliquots can be further compartmentalized by use of a lubricant to encapsulate the aliquot within a droplet or microdroplet. In particular embodiments, the volume is less than about 1 mL, 750 µL, 500 µL, 250 µL, 100 µL, 50 µL, 10 µL, 5 µL, 1 µL, 750 nL, 500 nL, 250 nL, 100 nL, 50 nL, 10 nL, 5 nL, 1 nL, 750 pL, 500 pL, 250 pL, 100 pL, 50 pL, 10 pL, 5 pL, 1 pL, 750 fL, 500 fL, 250 fL, 100 fL, 50 fL, 10 fL, 5 fL, 1 fL, 750 aL, 500 aL, 250 aL, 100 aL, 50 aL, 10 aL, 5 aL, or 1 aL. In other embodiments, the volume is from about 1 aL to about 1 mL (e.g., 1 aL to 750 µL, 1 aL to 500 µL, 1 aL to 250 µL, 1 aL to 100 µL, 1 aL to 50 µL, 1 aL to 10 µL, 1 aL to 5 µL, 1 aL to 1 µL, 1 aL to 750 nL, 1 aL to 500 nL, 1 aL to 250 nL, 1 aL to 100 nL, 1 aL to 50 nL, 1 aL to 10 nL, 1 aL to 5 nL, 1 aL to 1 nL, 1 aL to 750 µL, 1 aL to 500 µL, 1 aL to 250 µL, 1 aL to 100 µL, 1 aL to 50 µL, 1 aL to 10 µL, 1 aL to 5 µL, 1 aL to 1 µL, 1 aL to 750 fL, 5 aL to 1 nL, 5 aL to 750 µL, 5 aL to 500 µL, 5 aL to 250 µL, 5 aL to 100 µL, 5 aL to 50 µL, 5 aL to 10 µL, 5 aL to 5 µL, 5 aL to 1 µL, 5 aL to 750 nL, 5 aL to 500 nL, 5 aL to 250 nL, 5 aL to 100 nL, 5 aL to 50 nL, 5 aL to 10 nL, 5 aL to 5 nL, 5 aL to 1 nL, 5 aL to 750 µL, 5 aL to 500 µL, 5 aL to 250 µL, 5 aL to 100 µL, 5 aL to 50 µL, 5 aL to 10 µL, 5 aL to 5 µL, 5 aL to 1 µL, 5 aL to 750 fL, 1 fL to 1 nL, 1 fL to 750 µL, 1 fL to 500 µL, 1 fL to 250 µL, 1 fL to 100 µL, 1 fL to 50 µL, 1 fL to 10 µL, 1 fL to 5 µL, 1 fL to 1 µL, 1 fL to 750 nL, 1 fL to 500 nL, 1 fL to 250 nL, 1 fL to 100 nL, 1 fL to 50 nL, 1 fL to 10 nL, 1 fL to 5 nL, 1 fL to 1 nL, 1 fL to 750 µL, 1 fL to 500 µL, 1 fL to 250 µL, 1 fL to 100 µL, 1 fL to 50 µL, 1 fL to 10 µL, 1 fL to 5 µL, 1 fL to 1 pL, 1 fL to 750 fL, 1 µL to 1 nL, 1 µL to 750 µL, 1 µL to 500 µL, 1 µL to 250 µL, 1 µL to 100 µL, 1 µL to 50 µL, 1 µL to 10 µL, 1 µL to 5 µL, 1 µL to 1 µL, 1 µL to 750 nL, 1 µL to 500 nL, 1 pL to 250 nL, 1 µL to 100 nL, 1 µL to 50 nL, 1 µL to 10 nL, 1 µL to 5 nL, 1 µL to 1 nL, 1 µL to 750 µL, 1 µL to 500 µL, 1 µL to 250 µL, 1 µL to 100 µL, 1 µL to 50 µL, 1 µL to 10 µL, 1 µL to 5 pL, 1 nL to 1 nL, 1 nL to 750 µL, 1 nL to 500 µL, 1 nL to 250 µL, 1 nL to 100 µL, 1 nL to 50 µL, 1 nL to 10 µL, 1 nL to 5 µL, 1 nL to 1 µL, 1 nL to 750 nL, 1 nL to 500 nL, 1 nL to 250 nL, 1 nL to 100 nL, 1 nL to 50 nL, 1 nL to 10 nL, or 1 nL to 5 nL).

Various types of sample preparation and analysis can be conducted in the devices of the invention. Exemplary sample preparation and analysis include nucleic acid extraction, nucleic acid purification, nucleic acid enrichment, nucleic acid concentration, protein extraction, protein purification, protein enrichment, protein concentration, cell separation, sample enrichment, nucleic acid amplification, nucleic acid detection, protein detection, filtration, lysis, dehydration, rehydration, a binding reaction, a washing step, elution, an assay reaction, and/or detection of one or more samples or one or more analytes within a sample.

In particular, the methods described herein can be beneficial when analyzing samples with low concentrations of analytes, for example, dilute samples; rare nucleic acids, proteins, markers, and biomarkers of genetic or infectious disease; environmental pollutants; rare cells, such as circulating cancer cells, stem cells, or fetal cells in maternal blood for prenatal diagnostics; microbial cells in blood, sputum, bone marrow aspirates and other bodily fluids such as urine and cerebral spinal fluid for rapid early diagnostics of infections; viral loads (e.g., for HIV and/or HCV) in samples (e.g., in samples from subjects having or suspected of having chlamydia, gonorrhea, and/or HIV); enzymatic assays; cellular assays, such as to determine cell viability, cell adhesion, cell binding etc.; biological or chemical screens for catalytic activity, selectivity, or storage ability or sequestration (such as absorption of gas or trapping of toxic compounds, etc.); or analytical testing various properties such as electrical, magnetic, optical, etc. See e.g., U.S. Pub. Nos. 2005/0003399 and Int. Pub. No. WO 2009/048673, incorporated herein by reference. In particular, detecting low concentrations of an analyte (e.g., a single molecule or a single bacterium) remains a challenge in food, medical, and security industries. The device of the invention could be useful for concentrating such samples and performing analysis. In one example, the devices of the invention can be useful for creating a high local concentration of an analyte (e.g., by compartmentalization within a chamber and/or a droplet or by concentration by using a capture region) that would only be present in dilute concentrations for a bulk solution. In another example, devices of the invention can create high local concentrations of an analyte that can further be amplified, such as by PCR with a DNA sample or by quorum sensing with a bacterial sample. Accordingly, the devices of the invention can be used in combination with any useful PCR technique. Exemplary PCR techniques are disclosed in the following publications: US 2008/0166793, WO 08/069,884, US 2005/0019792, WO 07/081,386, WO 07/081,387, WO 07/133,710, WO 07/081,385, WO 08/063,227, US 2007/0195127, WO 07/089,541, WO 07/030,501, US 2007/0052781, WO 06/096571, US 2006/0078893, US 2006/0078888, US 2007/0184489, US 2007/0092914, US 2005/0221339, US 2007/0003442, US 2006/0163385, US 2005/0172476, US 2008/0003142, and US 2008/0014589, each of which is incorporated by reference herein in its entirety. The following articles, describing methods for concentrating cells and/or chemicals by making small volume areas with low numbers of items to no items being incorporated into the areas, with specific applications involving PCR, are incorporated by reference herein: Koh et al., Anal. Chem. 75:4591-4598 (2003); Gulliksen et al., Lab Chip. 5:416-420 (2005); Abrams et al., Ann N Y Acad. Sci. 1098:375-388 (2007); Cady et al., Proc. IEEE Sensors, 24-27 Oct. 2004 3:1191-1194 (2004); Ottesen et al., Science 314:1464-1467 (2006); Govind et al., Electrophoresis 27:3753-3763 (2006); Lapizco-Encinas et al., J. Microbiol. Methods 62:317-326 (2005); Wong et al., Anal. Chem.

76:6908-6914 (2004); Yang et al., Lab Chip 2:179-187 (2002); Du et al., Anal. Chem. 77:1330-1337 (2005); Huang et al., Science 315:81-84 (2004); Hong et al., Nat. Biotechnol. 22:435-439 (2004); Liu et al., Electrophoresis 23:1531-1536 (2003); Matsubara et al., Biosens. Bioelectron. 20:1482-1490 (2005); and Leamon et al., Nat. Methods 3:541-543 (2006).

The device of the present invention can be used to study and perform coagulation or clotting assays, protein aggregation, protein crystallization (including the use of lipidic cubic phase), crystallization and analysis of small molecules, macromolecules, and particles, crystallization and analysis of polymorphs, crystallization of pharmaceuticals, drugs and drug candidates, biomineralization, nanoparticle formation, the environment (via aqueous and air sampling), culturing conditions (e.g., stochastic confinement, lysis of cells, etc.), drug susceptibility, drug interactions, high throughput screening (e.g., one first substance with many, different second substances, or many, different first substances with many, different second substances), multiplex assays (e.g. PCR, Taqman, immunoassays (e.g., ELISA, FISH, etc.)), amplification (e.g., PCR, ligase chain reaction (LCR), transcription mediated amplification (TMA), reverse transcriptase initiated PCR, DNA or RNA hybridization techniques, sequencing, and the like), sandwich immunoassays, chemotaxis assays, ramification amplification (RAM), etc. Exemplary techniques for blood assays, crystallization assays, protein aggregation assays, culturing assays are described in U.S. Pat. Nos. 7,129,091, 6,949,575, 5,688,651, 7,329,485, 6,949,575, 5,688,651, 7,329,485, and 7,375,190; U.S. Pub. Nos. 2007/0172954, 2006/0003439, 2003/0022243, and 2005/0087122; and Int. Pub. Nos. WO 2007/089777 and WO 2009/015390, each of which is incorporated herein by reference in its entireties. The device of the present invention can be used for various syntheses, including catalysis, multistep reactions, immobilized multistep synthesis (e.g., small molecule, peptide and nucleic acid syntheses), solid state synthesis, radioisotope synthesis, etc. Finally, the device of the present invention can be used for purification and enrichment of samples.

In some embodiments, the device can contain chambers that are used as a positive control (e.g., an analyte pre-loaded in a chamber) and/or a negative control (e.g., a buffer pre-loaded in a chamber).

The devices and methods of the invention can be used to conduct any useful reaction. Exemplary, non-limiting reactions include photochemical and electrochemical reactions, chemical reactions such as synthetic reactions (e.g., synthesis of radioisotopes), neutralization reactions, decomposition reactions, displacement reactions, reduction-oxidation reactions, precipitation, crystallization (e.g., protein crystallization by free interface diffusion and/or vapor diffusion), combustion reactions, and polymerization reactions, as well as covalent and noncovalent binding, phase change, color change, phase formation, dissolution, light emission, changes of light absorption or emissive properties, temperature change or heat absorption or emission, conformational change, and folding or unfolding of a macromolecule such as a protein. Multistep reactions may be performed by controlling conditions at each subsequent relative movement of the device.

The device of the present invention can be designed to load multiple areas with different substances easily and economically. For example, the device is manufactured to include multiple chambers for preserving and analyzing multiple samples. Furthermore, each layer can be designed to perform a particular function. For example, a first layer allows for sample preparation (e.g., by including one or more desiccants, such as any described herein), second layer allows for sample purification (e.g., by use of one or more capture regions, such as any described herein), and a third layer allows for sample collection (e.g., any useful sample described herein).

Figure 8:
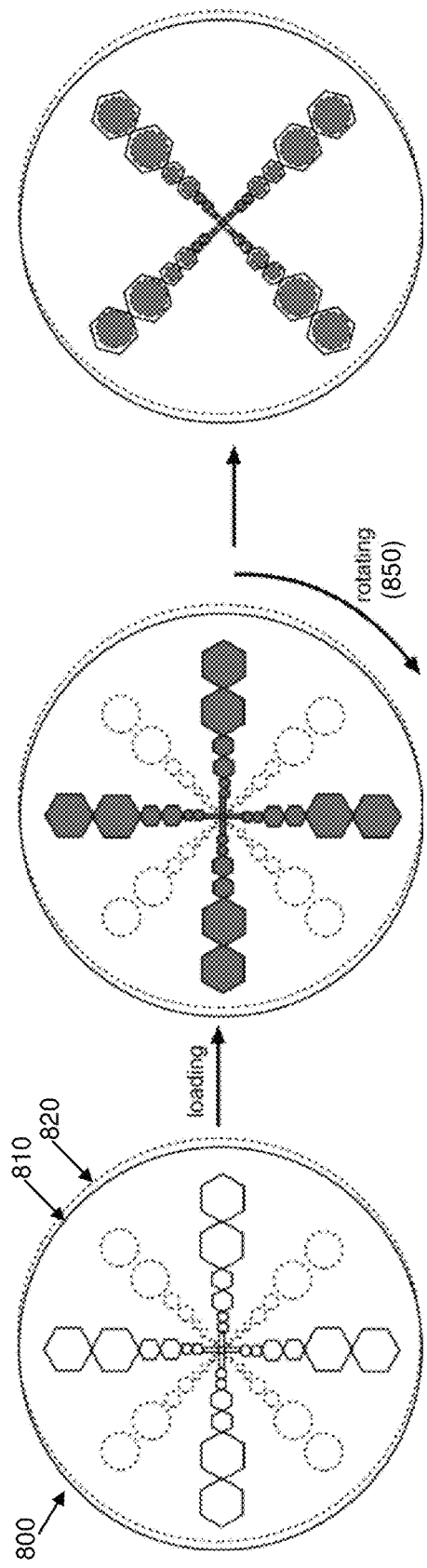
FIG. 8 provides a scheme describing a device 800 for rotational multivolume surface tension driven compartmentalization. The solid line indicates the top layer 810, the dotted line indicates the bottom layer 820, and the arrow 850 indicates relative rotational movement.

In other embodiments, the device could contain a plurality of chambers configured in the same locations as a standard multi-well plate or configured radially (e.g., such as in FIG. 8). Each layer can contain, for example, 6, 24, 96, 384, 1536, 3456, or 9600 chambers. In other embodiments, the device could contain at least about 1, 2, 3, 4, 5, 6, 7, 8, 9, 10, 20, 24, 30, 40, 48, 50, 60, 70, 80, 90, 96, 100, 200, 300, 384, 400, 500, 512, 1000, 1500, 1536, 2000, 2500, 3000, 3456, 3500, 4000, 4500, 5000, 6000, 7000, 8000, 9000, 9600, 10000, 1500, 2000, 2500, 3000, 4000, 5000, 6000, 7000, 8000, 9000, 10000, 20000, 30000, 40000, 50000, 60000, 70000, 80000, 90000, 100000, 200000, 200000, 400000, 500000, 600000, 700000, 800000, 900000, 1000000, or more chambers.

A multilayer approach can be used to extend the capability of the device further, such as integration of modules with various functions. Each layer can be designed to move freely (e.g., slip) relative to other layers. For example, in sample preparation, the separation matrix or nucleic acid extraction matrix can be embedded in the intermediate layer, reagent chambers are provided in the top layer, and receiving chambers are provided in the bottom layer. By slipping the intermediate layer, the capture region or matrix is aligned with each set of reagent chamber and receiving chamber, respectively. Receiving chambers with dead-end filling design can be used to control precisely the solution volume passing through the matrix. The speed of oil or lubricant displacement can be controlled by the gap and surface chemistry.

Exemplary devices, methods, and systems for sample preparation, including use of membrane matrices, are described in U.S. patent application Ser. No. 13/868,009, filed Apr. 22, 2013, and Ser. No. 13/868,028, filed Apr. 22, 2013, each of which is incorporated herein in its entirety (see, e.g., FIGS. 14-29, 54, and 55 in the aforementioned applications, which is incorporated herein in its entirety).

Sample preparation can also include the use of one or more pressure capping systems (e.g., including a cap, a lid, or a moving element, see, e.g., FIGS. 30-39, 43, and 44 in the following applications), such as those described in U.S. patent application Ser. No. 13/868,009, filed Apr. 22, 2013, and Ser. No. 13/868,028, filed Apr. 22, 2013, each of which is incorporated herein in its entirety.

The SlipChip platform can be compatible with a large variety of nucleic acid sample preparation methods, such as, for example, a combination of a chaotropic substance and a particle (e.g., any described herein, such as guanidinium thiocyanate with size-fractionated $SiO_2$ particles or with diatomaceous silicas (e.g., Celite®), as described in Boom et al., J. Clin. Microbiol. 28:495-503 (1990)), ChargeSwitch® and FTA (Whatman, GE) Chemistry. For example, SlipChip platform with ChargeSwitch® membrane has been validated with extraction of HIV viral RNA from spiked human plasma sample with efficiency comparable to commercial nucleic acid preparation method (see Examples herein). Furthermore, these nucleic acid sample preparation methods can be performed with multiplex analysis (e.g., by including one or more capture regions, as described herein).

SlipChip can integrate temperature control methods suitable for sample lysis for nucleic acid extraction, such as for example, temperature control methods based on simple phase transitions, where temperature is maintained constant during solid-liquid and liquid-solid phase transition, as described in the original application. As another example, SlipChip can be integrated with on-chip initiation mechanisms for temperature control such as initiation by slipping and mixing.

In some other embodiment, the membrane, matrix, or filter can be impregnated with at least one substance for lysing the cells, spores, or microorganisms in the sample, while drying the sample on the membrane, matrix, or filter by heating and/or absorbing moisture with the desiccant (e.g., such as described in U.S. Pat. Nos. 8,247,176 and 6,645,717, which is incorporated hereby by reference in its entirety). The released nucleic acid or other biomarkers can bind to the membrane matrix or filter, and further washing and elution can be applied.

Volume Quantification

The devices and systems of the invention can be used to quantify volumes of a sample, a reagent, or any useful substance (e.g., any described herein). In particular, quantification of volumes can be used in combination with any of the other devices and methods described herein, such as for sample preservation, sample treatment, sample preparation, and/or sample analysis. In particular, such volume quantification techniques can be useful for screening of special populations (such as newborns, infants, or small animals, e.g., for screening inherited metabolic disorders or lysosomal storage disorders, such as Fabry, Gaucher, Krabbe, Niemann-Pick A/B, and Pompe disease; for screening viral infections, such as HIV or CMV; or for screening other disorders using useful diagnostic markers, such as screening for succinylacetone, acylcarnitines, and amino acids to detect tyrosinemia type I (TYR 1) in newborns or infants), for use with a dried blood spot (DBS) sample (e.g., in combination with one or more sample preservation and/or storage devices and methods, as described herein), for screening metabolites (e.g., for pharmacokinetic, pharmacodynamic, toxicokinetic, or other drug monitoring assessments), for use in clinical trials (e.g., for pharmacokinetic or pharmacodynamic assessment of investigational drugs in clinical trials), and for determining adherence with particular drugs (e.g., for pharmacokinetic, pharmacodynamic, toxicokinetic, or other drug monitoring assessments). In particular embodiments, the test sample is a dried blood spot sample. In one non-limiting embodiment, the device including one or more of a membrane, a bridge, a matrix, a capture region, and/or a desiccant (e.g., a device for sample preservation including one or more of a membrane, a bridge, and/or a desiccant) is used, either with or without a collector, and a blood sample is introduced into the device. Next, the blood sample is dried (either partially or completely, e.g., as described herein). In some embodiments, the blood sample is dried onto a cellulose membrane that is optionally in fluidic communication with a desiccant. Then, the dried blood sample is processed and/or analyzed using one or more useful substances or reagents. Exemplary substances or reagents include a buffer (e.g., a wash buffer or an elution buffer, e.g., PBS containing 0.05% Tween 80 and 0.005% sodium azide, or any described herein), such as those used for screening in DBS technology, including amplification (e.g., PCR); detection of a virus, bacteria, protozoa, and/or helminth (e.g., HIV, hepatitis C virus, hepatitis B virus, hepatitis A virus, herpes simplex virus, rubella, measles, MMR (measles, mumps, and rubella), diphtheria, dengue, tetanus antitoxin, cytomegalovirus, human T-cell leukemia/lymphoma virus I or II, *Mycobacterium leprae*, *Helicobacter pylori*, *Brucella* sp, *Treponema pallidum*, *Toxoplasma gondii*, *Plasmodium falciparum*, *Trypanosoma cruzi*, *Giardia lamblia*, *Leishmania* spp, *Echinococcus granulosus*, *Schistosoma haematobium*, or *Brugia malayi*); detection of one or more metabolites (e.g., drug metabolites); detection of one or more analytes (e.g., any described herein, and including androstenedione, amino acids (e.g., arginine (Krebs cycle), histidine/urocanic acid, homocysteine, phenylalanine/tyrosine, and/or tryptophan), apolipoprotein (e.g., A-I or B), cortisol, CD4+ lymphocytes, cholesterol (e.g., including total cholesterol or high-density lipoprotein cholesterol (HDL)), C-reactive protein (CRP), dehydroepiandrosterone (DHEA, including its sulfate ester, DHEA-S), Epstein-Barr virus (EBV) antibodies, estradiol, folate, follicle-stimulating hormone (FSH), glucose, hemoglobin (e.g., including glycosylated Hemoglobin or HbA1c), hepatitis antigen/antibodies (e.g., hepatitis A, B, or C), HIV antibodies, homocysteine, IFNg, IGF-I, IGFBP-2, IGFB-3, IL-1b, IL-6, insulin, leptin, luteinizing hormone (LH), lipoprotein (e.g., (a), B/A-1, or β), prostate-specific antigen (PSA), progesterone, prolactin, retinol, sex hormone binding globulin (SHBG), somatomedin-C, testosterone, transferrin receptor, thyrotropin (TSH), thyroxine (T4), thyroglobulin, triglycerides, triiodothyronine (T3), or TNF (e.g., TNFa)); detection of one or more diagnostic markers for special populations, such as a newborn, a neonate, or an infant (e.g., detection of IgG antibodies for diagnosing infections; detection of succinylacetone, acylcarnitines, and amino acids for diagnosing tyrosinemia type I (TYR 1); detection of medium chain acyl CoA dehydrogenase for diagnosing MCAD deficiency; detection of human chorionic gonadotropin (hCG) for diagnosing Down syndrome; detection of glycated hemoglobin for diagnosing insulin-dependent diabetes; detection of trypsin for diagnosing cystic fibrosis; detection of HIV-specific antibodies and/or of HIV virus in combination with PCR; detection of thyroxine (T4) and thyrotropin (TSH) for diagnosing congenital hypothyroidism; detection of one or more enzymes (e.g., acid α-glucocerebrosidase (ABG), acid α-galactosidase A (GLA), lysosomal acid α-glucosidase (GAA), galactocerebroside α-galactosidase (GALC), or acid sphingomyelinase (ASM)) involved in lysosomal metabolism for diagnosing lysosomal storage disorders (e.g., Pompe, mucopolysaccharidosis (e.g., type I), Fabry, Gaucher, or Niemann-Pick type A/B diseases); for DNA analysis in combination with PCR analysis (e.g., for detecting or diagnosing acetylator polymorphism, alcohol dehydrogenase, alpha 1-antitrypsin, cystic fibrosis, Duchenne/Becker muscular dystrophy, glucose-6-phosphate dehydrogenase, hemoglobinopathy A, hemoglobinopathy S, hemoglobinopathy C, hemoglobinopathy E, D-Punjab, beta-thalassemia, hepatitis B virus, HCMV, HIV-1, HTLV-1, Leber hereditary optic neuropathy, MCAD, PKU, *Plasmodium vivax*, sexual differentiation, or 21-deoxycortisol); for detecting certain antigens (e.g., hepatitis B virus or HIV-1); for detecting certain antibodies (e.g., adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, *leptospira*, measles/mumps/rubella *Mycobacterium leprae*, *Mycoplasma pneumoniae*, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli* vesicular stomatis virus, *Wuchereria bancrofti*, or yellow fever virus); or screening of one or more drug metabolites or drug analytes (e.g., for pharmacokinetic, pharmacodynamic, toxicokinetic, or other drug monitoring assessments in clinical trials, in clinical monitoring, or in determining adherence with particular drugs, where exemplary drugs include anti-cancer drugs such as everolimus or tacrolimus; acetaminophen; investigational new drugs; or others). Further analytes, DBS assays, and methods are described in McDade et al., Demography 44:899-925 (2007); Cassol et al., J. Clin. Microbiol. 29:667-671 (1991); Bellisaro et al., Clin. Chem. 46:1422-1424 (2000); Williams et al., J. Gerontol. B Psychol. Sci. Soc. Sci. 64B(suppl_1): i131-i136 (2009); Parker et al., J. Clin. Pathol. 52:633-639 (1999); Li et al., Biomed. Chromatograph. 24:49-65 (2010); and De Jesus et al., Clin. Chem. 55:158-164 (2009), each of which is incorporated herein in its entirety.

Exemplary devices, methods, and systems for volume quantification are described in U.S. patent application Ser. No. 13/868,009, filed Apr. 22, 2013, and Ser. No. 13/868,028, filed Apr. 22, 2013, each of which is incorporated herein in its entirety.

Combined Sample Preservation, Sample Treatment, Sample Preparation, and/or Volume Quantification, and Kits Thereof Any of the devices and/or methods herein can be combined to achieve multiplexed sample storage, sample preservation, and/or analysis (e.g., such as in a kit with a collector). For instance, the devices herein for sample preservation and/or volume quantification (e.g., including one or more membranes, bridges, and/or desiccants) can be combined with one or more features provided for devices herein for sample treatment and/or sample analysis (e.g., including one or more capture regions). Exemplary devices, methods, and systems for multiplexed, combined analyses, as well as kits, are described in U.S. patent application Ser. No. 13/868,009, filed Apr. 22, 2013, and Ser. No. 13/868,028, filed Apr. 22, 2013, each of which is incorporated herein in its entirety.

Cell Phone Detection

The systems of the invention can further includes a detection system for detecting and/or relaying the results of the analysis. A cell phone (or equivalent hand held camera) can be used to image a pattern of dots on a SlipChip device, to automatically process the photograph for analysis, and to autonomously send and receive results. To allow for a high level of medical care, results can be transmitted to reference laboratories or remote physicians without user effort. In some embodiments, the device and the cell phone can be provided together for maximum utility in the field.

Exemplary devices, methods, and systems for detection with an electronic device (e.g., an a cell phone, a smartphone, a mobile device, a mobile phone, a camera, a handheld camera, a video camera, or an imaging device) are described in U.S. patent application Ser. No. 13/868,009, filed Apr. 22, 2013, and Ser. No. 13/868,028, filed Apr. 22, 2013, each of which is incorporated herein in its entirety.

Integration for Devices and Systems

The devices and systems of the invention can be integrated with other devices to allow multistep processes. For example, the sample preparation modules can be included in the device by exploiting the modularity of SlipChip devices, in order to prepare the sample before storage.

Examples include but are not limited to devices for multistep protocols for nucleic acid extraction and filtration elements to separate plasma from whole blood using membranes and/or integrated filtration elements such as geometrical features in the device (for example, restrictions or a gap between the plates). The device can include further optional components useful for use, as described herein.

Exemplary devices, methods, and systems for integration with devices (e.g., pressure capping, sample loading, automated analysis, a pressurization apparatus, a loading apparatus, an injection port for serial and/or sequential filling of the chamber(s), a heating element, an on-chip lysis component, a plasma separation component, a detector, markers, or molecular recognition module) are described in U.S. patent application Ser. No. 13/868,009, filed Apr. 22, 2013, and Ser. No. 13/868,028, filed Apr. 22, 2013, each of which is incorporated herein in its entirety.

EXAMPLES

Example 1: Device for Surface Tension Drive Compartmentalization

The devices of the invention can include one or more structures (e.g., channels) to promote surface tension drive compartmentalization. We designed devices including chambers connected by channels in the top layer (FIGS. 1A (solid line) and 1D), where the surface was rendered hydrophobic. Separate, unconnected receiving chambers were incorporated into the bottom layer (FIGS. 1A (dashed line) and 1D), and the surface can be either hydrophobic or hydrophilic. For loading these devices, reagents can be preloaded into the receiving chambers in the top layer either with or without a lubricant. As shown in FIGS. 1B and 1E, a solution was introduced into the device through the continuous fluidic path formed by the chambers and channels in the top layer. Then, the top layer was slipped relative to the bottom layer to connect the chambers in the top layer with the chambers in the bottom layer (FIGS. 1C and 1F). In particular, the receiving chambers in the bottom layer provided additional space (and a lubricant, e.g. oil), which allows the fluid to break up at the channels due to surface tension. As shown in FIGS. 1C and 1F, individual reaction compartments (or droplets) were formed.

Example 2: Device Including Additional Receiving Chambers

Figure 2:
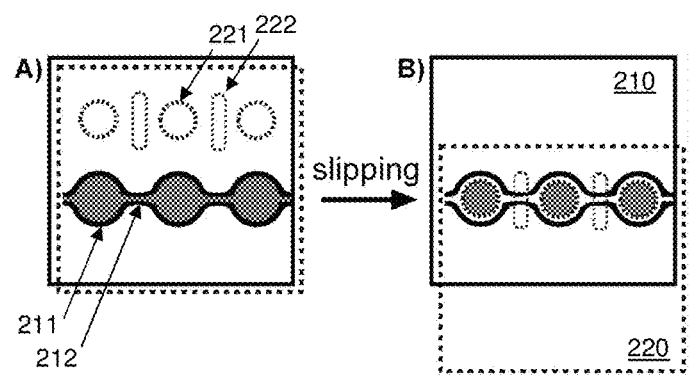
FIGS. 2A-2B provide schemes for additional receiving chambers 222 for channels 212 to facilitate compartmentalization and prevent cross-contamination. The solid line indicates the top layer 210 having chambers 211 connected by a channel 212, and the dotted line indicates the bottom layer 220 having receiving chambers 221 and additional receiving chambers 222 that are elongated.
Figure 3:
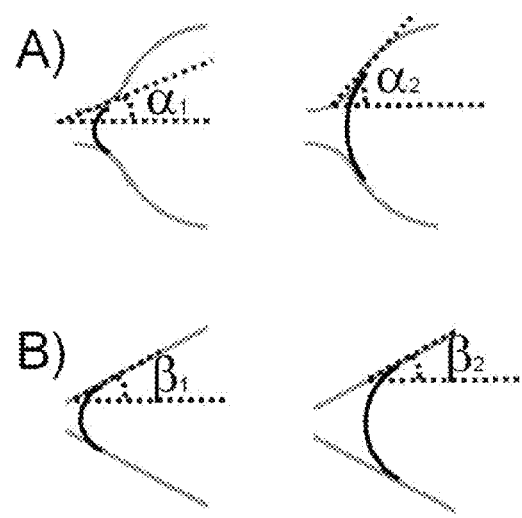
FIGS. 3A-3B provide schemes for different geometries of channels and chambers for surface tension driven compartmentalization. Solid grey lines indicate the shape of the chambers and channels, and solid black lines indicate the front of a solution. With the same horizontal distance, design of FIG. 3A provides a larger change in radius ($\alpha_1$ versus $\alpha_2$) than the design of FIG. 3B ($\beta_1$ versus $\beta_2$).

The devices of the invention can also include additional receiving chambers, such as a plurality of third chambers in the bottom layer. As shown in FIG. 2, the device includes a top layer 210 including first chambers 211 (or wells) connected by channels 212 (or necks). The bottom layer 220 includes second chambers 221(receiving wells) and third chambers 222 (or additional receiving wells). These additional receiving chambers can facilitate the break-up of a sample after slipping and prevent cross-contamination during downstream applications. In particular embodiments, the additional receiving chambers include a lubricant. In other embodiments, these additional receiving chambers in the bottom layer are designed to overlap with the channels in the first layer after slipping.

Example 3: Design Considerations for Devices

The structures of the device can be designed using principles related to fluid break-up, such as by pressure or surface tension forces. The relation of pressure difference and surface tension is described by the Young-Laplace equation as:

$$\Delta p = \gamma \left( \frac{1}{R_x} + \frac{1}{R_y} \right) \quad \text{(Eq. 1)}$$

where $R_x$ and $R_y$ are radii of curvature in each of the axes. As can be seen, a greater change of R would introduce a greater difference of pressure, which is preferred for solution breaking up at the channels. Thus, the chambers and channels connecting the channels can be designed to promote a great would offer a greater change in radii. For the exemplary, non-limiting designs described in FIGS. 3A-3B, the change in radii for the design in FIG. 3A is greater than that in FIG. 3B. Further, the chambers and/or channels can also be designed to have different cross-sectional dimensions (e.g., height, as described in FIG. 4) to facilitate the breakup of solution at the channel section. In particular embodiments, the chambers and channels are designed to provide a greater change in the cross-sectional dimension between the cross-sectional dimension of the chamber and the cross-sectional dimension of the channel.

Example 4: Multistep Slipping of Surface Tension Driven Compartmentalization SlipChip The devices of the invention can be designed to promote multiple reaction steps and/or reagents. In one embodiment, two or more steps of slipping can be programmed in the surface tension driven compartmentalization SlipChip to process, mix, or analyze two or more reagents.

Figure 5:
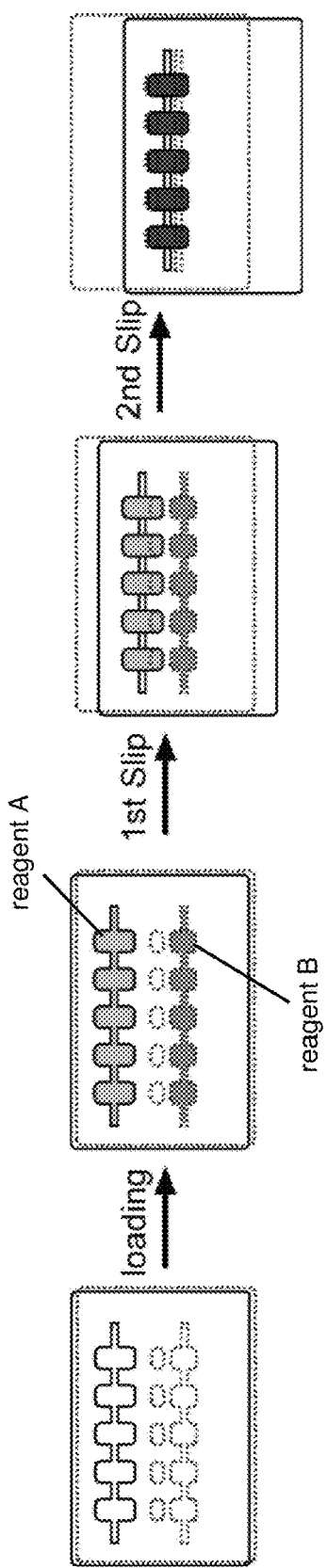
FIG. 5 provides a scheme for compartmentalizing and mixing of two reagents (reagents A and B). The black solid line indicates the top layer, and the dotted line indicates the bottom layer. After the first slip, reagent A is compartmentalized. After the second slip, compartmentalized reagent A is mixed with reagent B, and the resultant combination of these reagents (A+B) are also compartmentalized.
Figure 6:
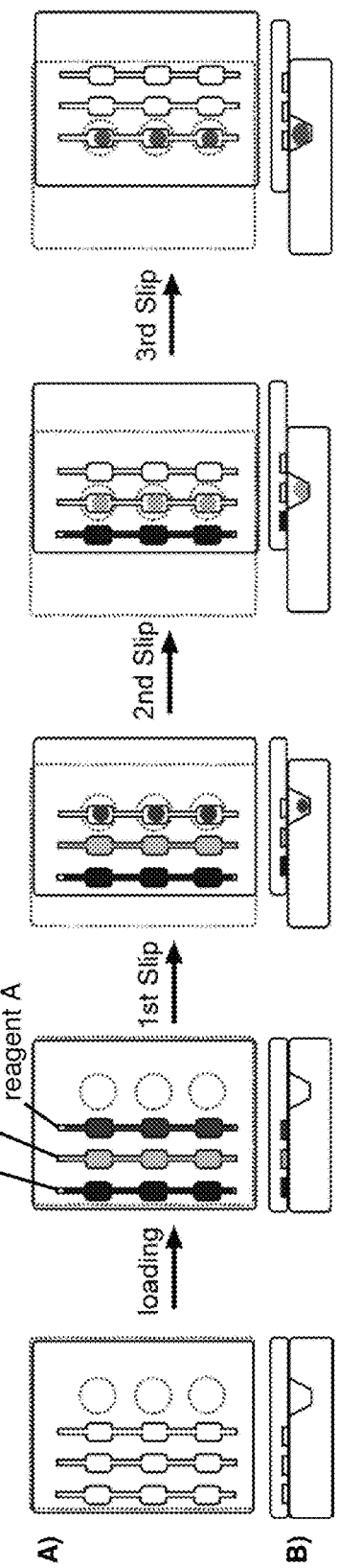
FIGS. 6A-6B provide schemes for sequential compartmentalization and addition/mixing of reagents in plan view (A) and side view (B). The solid line indicates the top layer, and the dotted line indicates the bottom layer. After the first slip, reagent A is compartmentalized. After the second slip, compartmentalized reagent A is mixed with reagent B, and the resultant combination of these reagents (A+B) are also compartmentalized. After the third slip, compartmentalized reagents A+B are mixed with reagent C, and the resultant combination of these reagents (A+B+C) are also compartmentalized.

As described in FIGS. 5 and 6, the device can include multiple arrays of chambers and channels to facilitate the use of multiple reagents in the device. Such devices can allow for N×M combinations of solutions or reagents, where N and M are integers greater than 1. In one embodiment, different substances can be added to the plurality of chambers sequentially by surface tension driven compartmentalization with multistep slipping. In particular embodiments, the depth or height of chambers of the top layer is less than the depth or height of chambers of the bottom layer. For example, if the density of a lubricant is less than the sample solution (e.g., an aqueous solution), then break-up of the samples due to surface tension will provide droplets that settle at the bottom of the chambers in the bottom layer. In another embodiment, the depth or height of the chambers of the bottom layer can be less than depth or height of chambers of the top layer, and the lubricant is less dense than the sample solution (e.g., an aqueous solution). In other embodiments, density differences are not required to achieve such effects, and compartmentalization arises from surface tension driven forces.

Other types of slipping and layouts can be used, including spiral layouts. Furthermore, slips could be performed in different directions (e.g., any described herein, such as in FIG. 8).

Example 5: Parallel Control of Slip-Compartmentalization Versus Surface Tension Driven Compartmentalization on the Same SlipChip The devices of the invention can be designed to promote various types of compartmentalization. In some embodiments, the continuous fluidic path contains chambers 711 connected by a channel 712 in the top layer 710 and separated chambers 722 (dashed line) in a bottom layer 720 (see, e.g., FIG. 7A). The receiving chambers are designed on both top and bottom layers, which include chambers 715 in the top layer and 721 in the bottom layer. A sample can be introduced through the fluidic path (FIG. 7B). The bottom layer 720 is slipped relative to the top layer 710, and the receiving chambers 721 on the bottom layer overlap with chambers 711 connected by the channel 712 on the top layer, and individual droplets 750 are achieved by surface tension. The chambers 722 in the bottom layer containing solution overlap with receiving chambers 715 on the top layer and form compartments 755. This setup is, e.g., preferred by PCR thermal cycling, while in other embodiments, the receiving chambers on the top layer are not necessary.

Example 6: Rotational and Surface Tension Driven Compartmentalization

The devices of the invention can be designed to promote compartmentalization after relative rotational movement. In one embodiment, relative movement can be achieve by rotating one layer for certain degree relative a second layer. In other embodiments, areas of multiple volumes or chambers can be used, which is useful, for example, for digital analysis with expanded dynamic range. An exemplary device including rotational movement and an array of chambers having multiple volumes is provided in FIG. 8.

Example 7: Recovery of Solution after Processing on SlipChip

After processing or analyzing a sample, the resultant sample can be recovered by any useful method. In some embodiments, a sample is recovered by connecting using a lubricant of a third phase (e.g., air or another immiscible fluid) through a fluidic path in the device. The recovered product can be applied for other analysis, such as, e.g., sequencing,

Example 8: Digital Nucleic Acid Amplification on Surface Tension Driven Compartmentalization SlipChip A surface tension driven compartmentalization SlipChip was applied for digital PCR. Using a device such as that in FIG. 1, the connected chamber had a radius of 1100 µm and depth of 50 µm, whereas the channel had a width of 50 µm, and the shallowest part of the channel is 10 µm. The PCR solution and protocol for amplification of *S. aureus* nuc gene was as described in Shen et al., Anal. Chem. 82:4606-4612 (2010). First, a solution was introduced into the device and slipped to compartmentalize as described in FIG. 1. Then, the SlipChip was placed on a flat adaptor on a thermal cycler for thermal cycling. After amplification, the SlipChip was imaged using fluorescent microscope.

Figure 9:
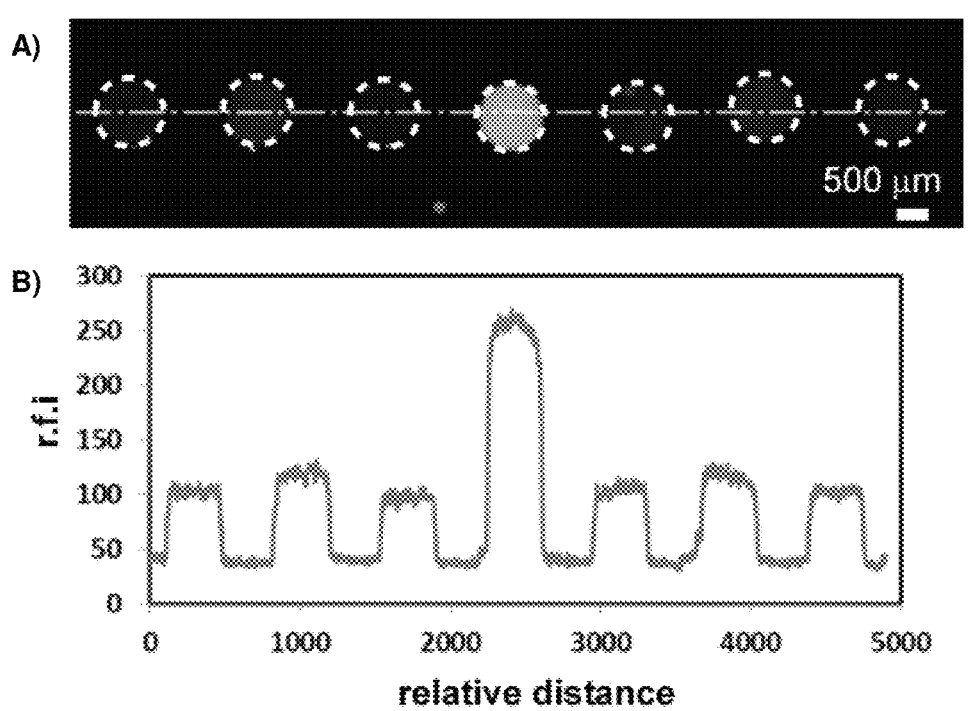
FIGS. 9A-9B provide digital PCR of *S. aureus* nuc gene on a sample that underwent surface tension driven compartmentalization in a SlipChip. Provided are (A) a fluorescence microphotograph and (B) a graph quantifying relative fluorescence intensity (r.f.i.) in the chambers of the SlipChip.

Digital amplification was achieved in the experiment, as there was significant increase of fluorescent intensity in positive chamber and no increase of fluorescent intensity in the negative chambers (FIG. 9). No cross contamination was observed, as evidenced by the a single positive chamber in between an array of negative chambers. The size of seven adjacent chambers was measured with an average of 106045.7 relative units and a standard deviation of 5774.0 relative units. The variation in surface area was approximately 5.4% among these seven adjacent chambers. Based on these data, surface tension driven compartmentalization can prevent cross contamination even under thermal cycling conditions.

Example 9: Exemplary Devices Including Second Chambers

Figure 13:
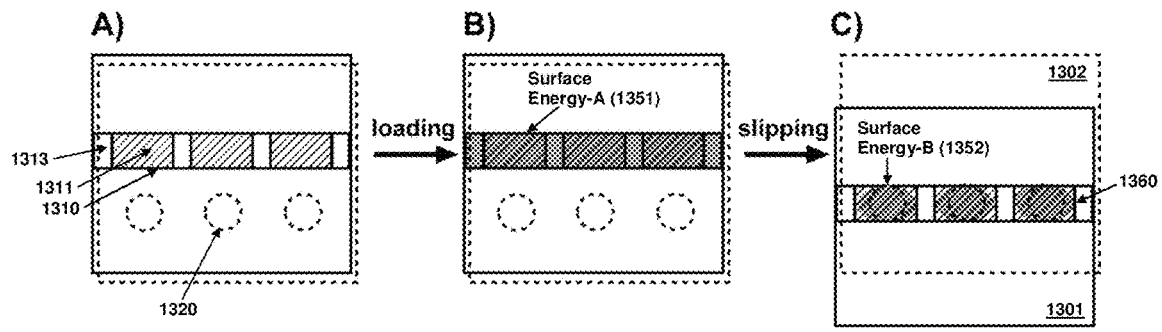
FIGS. 13A-13C provide schemes of a first layer 1301 and a second layer 1302 having various regions. A: The first layer includes a channel 1310 having a plurality of first regions 1311 and a plurality of third regions 1313, where first regions 1311 and third regions 1313 may have the same or different surface energies. The second layer includes second regions 1320 (e.g., chambers). B: A target fluid (gray, e.g., a sample) can be loaded into the channel 1310, where the target fluid has surface energy-A (1351). C: After slipping by relative movement, the target fluid is compartmentalized, where the compartmentalized fluid has surface energy-B (1352). In some embodiments, the surface energy of the system is determined by the surface energy of the target fluid. In this instance, the surface energy of the system before slipping (FIG. 13A) is greater than the surface energy of the system after slipping and compartmentalization (FIG. 13C). In one non-limiting embodiment, the surface energy of the system can be controlled by controlling the surface energy of the target fluid. For instance, accounting for surface energy-A (1351) of the target fluid before compartmentalization and surface energy-B (1352) of the target fluid energy after compartmentalization, the surface energy of the system is minimized by the formation of compartments in the combined region formed by the first region 1311 and the second region 1320. In particular embodiments, the fluid 1360 surrounding the target fluid is an immiscible fluid (e.g., any described herein, including air, oil, or a lubricant).
Figure 14:
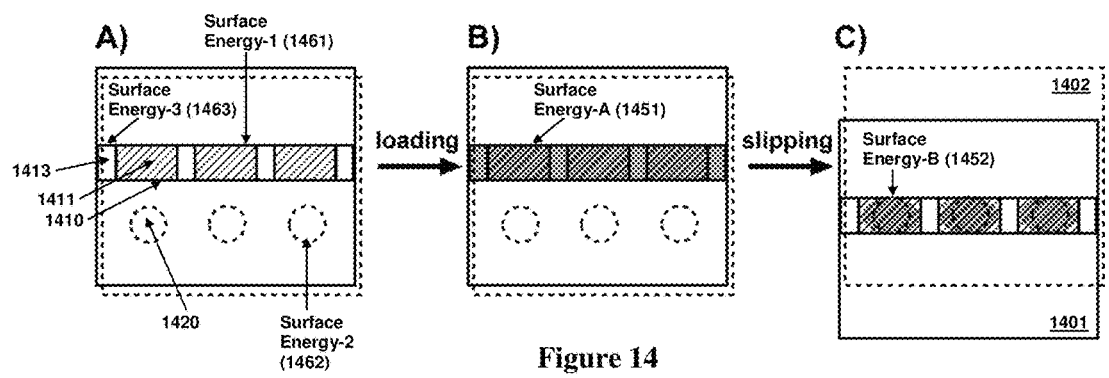
FIGS. 14A-14C provide schemes of a first layer 1401 and a second layer 1402 having various regions. A: The first layer 1401 includes a channel 1410 having a plurality of first regions 1411 and a plurality of third regions 1413, where first regions 1411 have surface energy-1 (1461) and the third regions 1413 have surface energy-3 (1463). Surface energy-1 and -3 may be the same or different. The second layer 1402 includes second regions 1420 (e.g., chambers) having surface energy-2 (1462). B: A target fluid (gray, e.g., a sample) can be loaded into the channel 1410, where the target fluid has surface energy-A (1451). C: After slipping by relative movement, the target fluid is compartmentalized, where the compartmentalized fluid has surface energy-B (1452). In some embodiments, the surface energy of the system is determined by the surface energy of the first region and the third region. In some embodiments, surface energy-1 and -3 are different, and surface energy-A of the target fluid is closer in energy to surface energy-1 than surface energy-3. This difference promotes compartmentalization of the target fluid in the combined region (see, e.g., FIG. 14C). In other embodiments, a third region 1413 is hydrophobic, and a first region 1411 is hydrophilic. In this example, an aqueous target fluid can be loaded into the channel, and, after slipping, the aqueous target fluid breaks up at the third region and is compartmentalized in the combined region (see, e.g., FIG. 14C).
Figure 15:
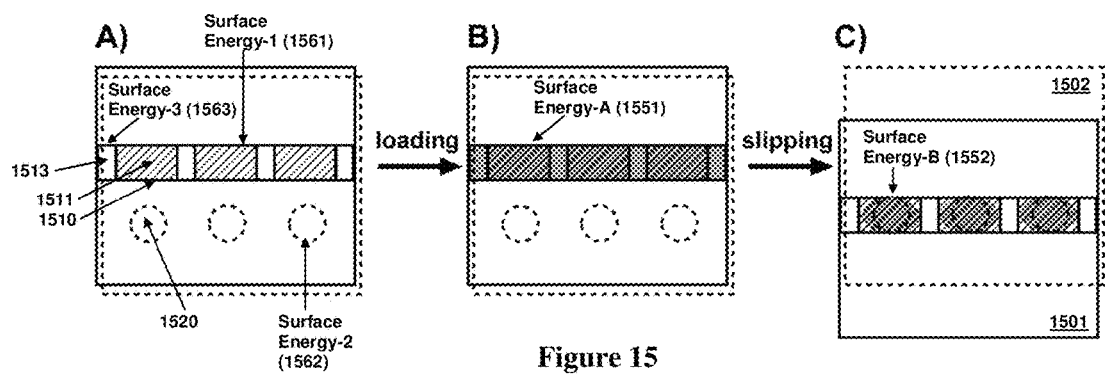
FIGS. 15A-15C provide schemes of a first layer 1501 and a second layer 1502 having various regions. A: The first layer 1501 includes a channel 1510 having a plurality of first regions 1511 and a plurality of third regions 1513, where first regions 1511 have surface energy-1 (1561) and the third regions 1513 have surface energy-3 (1563). Surface energy-1 and -3 may be the same or different. The second layer 1502 includes second regions 1520 (e.g., chambers) having surface energy-2 (1562). B: A target fluid (gray, e.g., a sample) can be loaded into the channel 1510, where the target fluid has surface energy-A (1551). C: After slipping by relative movement, the target fluid is compartmentalized, where the compartmentalized fluid has surface energy-B (1552). In some embodiments, the surface energy of the system is determined by the surface energy of the first region, second region, and the third region. In some embodiments, surface energy-1, -2, and -3 can be the same or different, and the surface energy of the system is determined by the interplay of surface energy-1 (i.e., energy of the interfaces between device surface of the first region and the target fluid and/or immiscible fluid), surface energy-2 (i.e., energy of the interfaces between device surface of the second region and the target fluid and/or immiscible fluid), surface energy-3 (i.e., energy of the interfaces between device surface of the third region and the target fluid and/or immiscible fluid), surface energy-A (i.e., energy of the interfaces between device surface of the first region, the third region, the target fluid, and/or the immiscible fluid), and surface energy-B (i.e., energy of the interfaces between device surface of the first region, the target fluid, and/or the immiscible fluid). By balancing the interplay of these surface energies, the surface energy of the system is minimized by forming compartments of target fluid surrounded by an immiscible fluid (see, e.g., FIG. 15C).

The device can include a first layer having various first regions and a second layer having a plurality of second chambers (see, e.g., FIGS. 13-15).

In some embodiments, the surface energy of the system is minimized by using a device having a plurality of first regions 1311 and a plurality of third regions 1313, where first regions 1311 and third regions 1313 may have the same or different surface energies (FIGS. 13A-13B). In further embodiments, the surface energy of the system is determined by the surface energy of the target fluid. In this instance, the surface energy of the system before slipping (FIG. 13A) is greater than the surface energy of the system after slipping and compartmentalization (FIG. 13C).

In some embodiments, the first layer contains a channel 1410 with patterns of areas of different surface energy (surface energy-1 and surface energy-3 in FIG. 14). For instance, in particular embodiments, the first region 1411 can be hydrophobic, and the third region 1413 can be hydrophilic. An aqueous target fluid can be loaded into the channel. After slipping, the channel in the first layer can be overlapped with receiving wells in the second layer, where the aqueous target fluid is then compartmentalized primarily within the first region 1411 to minimize the surface energy of the system including the first region, the second region, the third region, and the target fluid.

In yet other embodiments, the surface energy of the system includes consideration of all relevant surfaces and interfaces (e.g., solid-solid, solid-fluid, fluid-fluid, as well as solid-fluid-fluid interfaces, where the fluid can be a gas or a liquid). For instance the surface energy of the system includes the interplay of surface energy-1 (i.e., energy of the interfaces between device surface of the first region and the target fluid and/or immiscible fluid), surface energy-2 (i.e., energy of the interfaces between device surface of the second region and the target fluid and/or immiscible fluid), surface energy-3 (i.e., energy of the interfaces between device surface of the third region and the target fluid and/or immiscible fluid), surface energy-A (i.e., energy of the interfaces between device surface of the first region, the third region, the target fluid, and/or the immiscible fluid), and surface energy-B (i.e., energy of the interfaces between device surface of the first region, the target fluid, and/or the immiscible fluid) (see, e.g., FIGS. 15A-15C and the brief description of these figures provided herein. In one non-limiting example (in FIG. 15), the target fluid can be an aqueous solution, the first and/or second regions (1511 and 1512) can be hydrophilic, and the third regions (1513) are hydrophobic. After slipping and compartmentalization, the surface energy of the system will be minimized by forming compartments within the combined region of the first and second regions.

Accordingly, the present invention encompasses the devices, as well as methods, that account for various surface energies of the target fluid, immiscible fluid, and surface of a device (or a portion thereof, e.g., such as any region, chamber, channel, or capture region) to compartmentalize the target fluid.

Example 10: Exemplary Devices Including Second Regions

Figure 16:
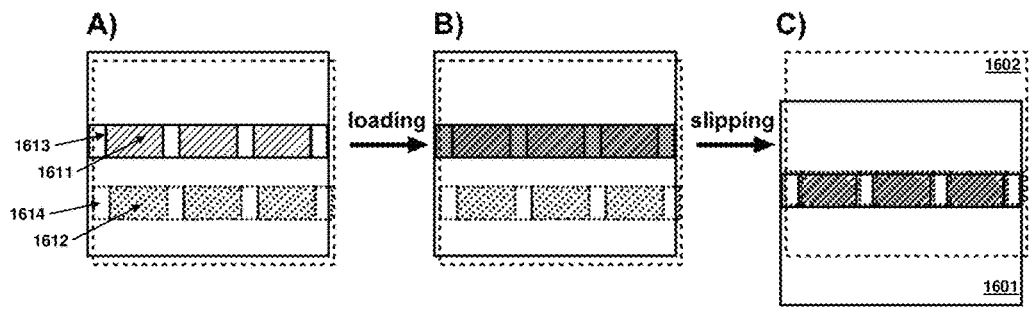
FIGS. 16A-16C provide schemes of a first layer 1601 and a second layer 1602 having various regions. A: The first layer 1601 includes a channel having a plurality of first regions 1611 and a plurality of third regions 1613. The second layer 1602 includes a channel having a plurality of second regions 1612 and a plurality of fourth regions 1614. B: A target fluid (gray, e.g., a sample) can be loaded into the first region. C: After slipping by relative movement, the target fluid is compartmentalized.

The device can include a first layer having various first regions and a second layer having a plurality of second regions (see, e.g., FIG. 16).

In some embodiments, a first layer includes patterns of a first region 1611 and a third region 1613 (e.g., having different surface energy, surface energy-1 and surface energy-2, in FIG. 16A). Further, the second layer includes patterns of a second region 1612 and a fourth region 1614. In particular embodiments, the second layer includes patterns of regions that are complementary to the patterns of regions in the first layer. In further embodiments, the target fluid is loaded into the first regions, and, after slipping, the target fluid forms compartments based on the difference in surface energy in between the first region and the combined first region and second region.

In other embodiments, the second regions and/or fourth regions are designed such that, after slipping and compartmentalization, the surface energy of the system after compartmentalization is lower than the surface energy of the system before compartmentalization. For instance, the surface energy of the system when the target fluid is in the first region is more than the surface energy of the system when the target fluid in the combined region (e.g., the combined region formed from a first region 1611 and second region 1612 in FIG. 16), such that the change in surface energy of the system provides a plurality of compartments. In a further embodiment, the fourth region can be designed to preferentially break droplets at the interface of the target fluid and the surface of the fourth region or the interface formed between the target fluid, immiscible fluid, and the surface of the fourth region. In one non-limiting example, the target fluid can be an aqueous solution, the first and second regions (1611 and 1612) can be hydrophilic, and the third and fourth regions (1613 and 1614) are hydrophobic. After slipping and compartmentalization, the surface energy of the system will be minimized by forming compartments within the combined region of the first and second region. In another non-limiting example, the target fluid can be a hydrocarbon, the first and second regions (1611 and 1612) can be hydrophilic, and the third and fourth regions (1613 and 1614) are hydrophobic. After slipping and compartmentalization, the surface energy of the system will be minimized by forming compartments within the combined region of the third and fourth regions.

Example 11: Exemplary Devices Including Arrays

Figure 17:
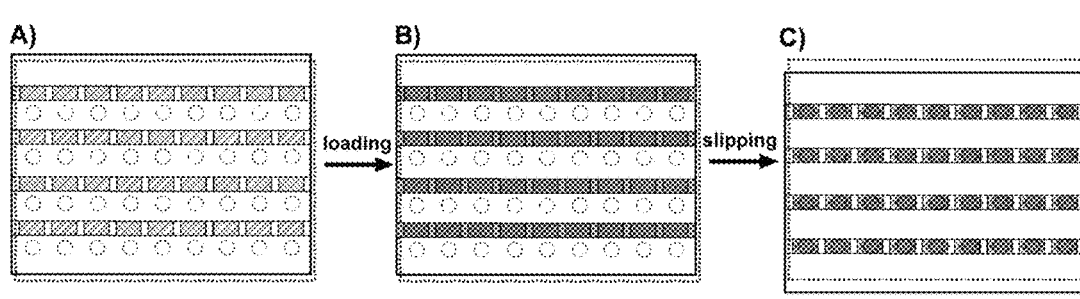
FIGS. 17A-17C provide schemes for exemplary arrays of first and third regions in the first layer (solid lines) and arrays of second regions (e.g., second chambers) in the second layer (dashed lines) (A, see, e.g., FIGS. 15A-15C for first and third regions), as well as these layers after loading a sample (B) and after slipping and compartmentalization (C).
Figure 18:
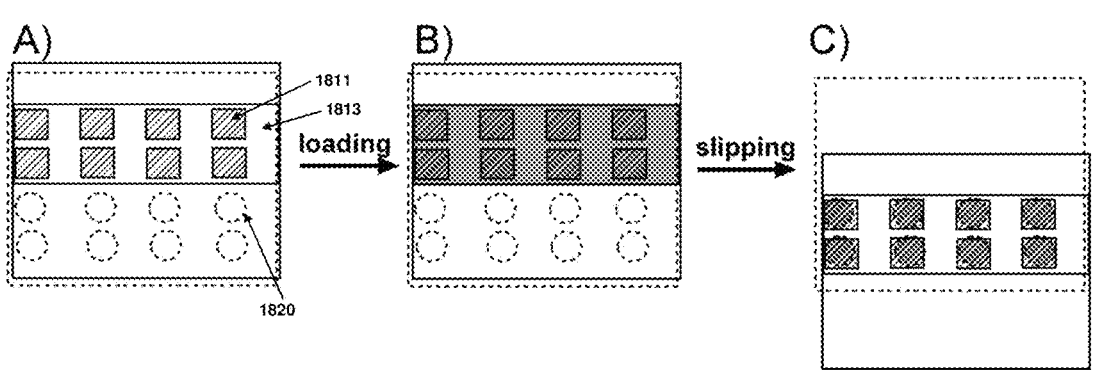
FIGS. 18A-18C provide schemes for exemplary arrays of first 1811 and third regions 1813 in the first layer (solid lines) and arrays of second regions 1820 (e.g., second chambers) in the second layer (dashed lines), as well as these layers after loading a sample (B) and after slipping and compartmentalization (C).
Figure 19:
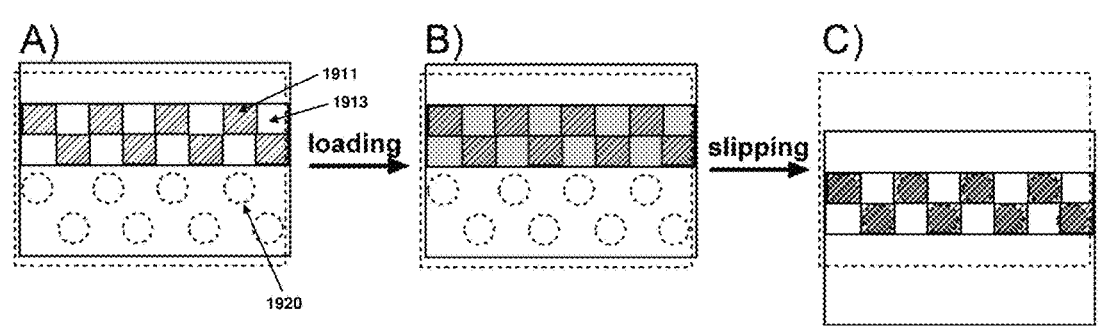
FIGS. 19A-19C provide schemes for exemplary arrays of first 1911 and third regions 1913 in the first layer (solid lines) and arrays of second regions 1920 (e.g., second chambers) in the second layer (dashed lines), as well as these layers after loading a sample (B) and after slipping and compartmentalization (C).

The devices of the invention can include various arrays (see, e.g., FIGS. 17-19). In some embodiments, the first layer includes an array of multiple first regions with alternating third regions (e.g., having areas of different surface energy for the first and third regions). The second layer can include an array of chambers (FIGS. 17A-17C). These arrays can be arranged in any useful format, such as alternating rows for first and second regions (FIGS. 17A-17C) and any geometric arrangement that allows for connection by relative movement of the first and second layers to form a plurality of combined regions (see, e.g., FIGS. 18A-18C and 19A-19C).

Example 12: Exemplary Devices Including a First Channel

Figure 20:
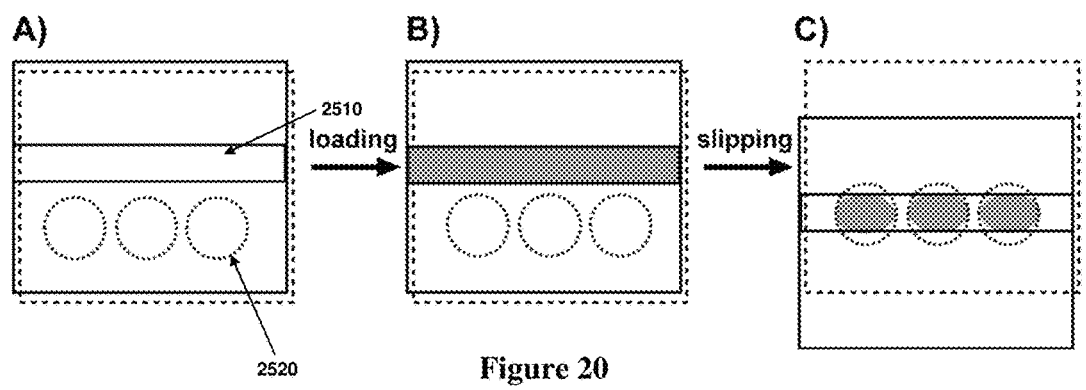
FIGS. 20A-20C provide schemes for a first layer (solid lines) having a first channel 2510 and a second layer (dashed lines) having a plurality of second regions 2520 (A), as well as these layers after loading a sample (B) and after slipping and compartmentalization (C).
Figure 21:
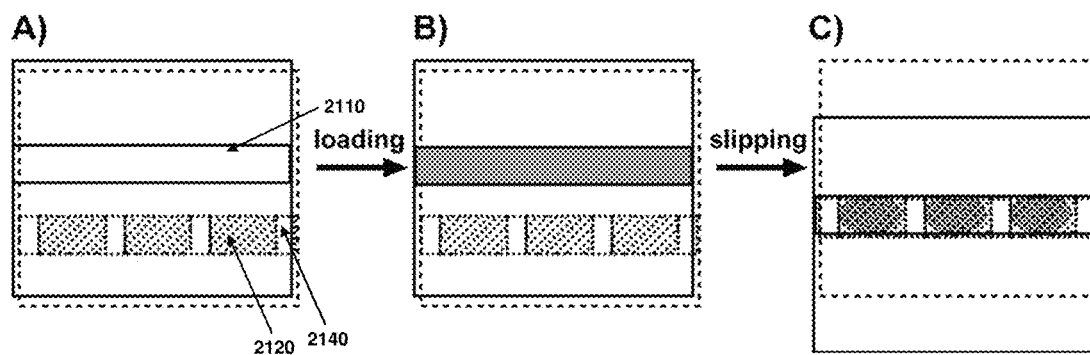
FIGS. 21A-21C provide schemes for a first layer (solid lines) having a first channel 2110 and a second layer (dashed lines) having a plurality of second regions 2120 and a plurality of fourth regions 2140 (A), as well as these layers after loading a sample (B) and after slipping and compartmentalization (C).

The devices of the invention can include a first layer having a first channel (see, e.g., FIGS. 20-21). The surface energy of the system is reduced by separating the target fluid into compartments by using a second layer having a particular geometry (e.g., second chambers in FIG. 20A) or having second regions having different surface characteristics (e.g., second and fourth regions in FIG. 21A). After loading and slipping, compartments of the target fluid are formed (FIGS. 20B-20C and 21B-21C).

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A system for compartmentalization comprising a device, a target fluid, an immiscible fluid, and a surface energy,
   wherein the device comprises
   (i) a first layer comprising a first region; and
   (ii) a second layer comprising a plurality of second regions;
      wherein said first region and said plurality of second regions are connected by relative movement of the first and second layers from a first position, wherein the first region is not connected to the plurality of second regions, to a second position, wherein the first region is connected to the plurality of second regions to form a plurality of combined regions,
      wherein, in said first position, said target fluid is present in said first region, and wherein relative movement of said device from said first position to said second position results in separation of said target fluid into compartments that are separated by said immiscible fluid and located in said plurality of combined regions, and
      wherein, in said second position, the surface energy of the system is reduced from a first surface energy before said separation of said target fluid into said compartments to a second surface energy after said separation of said target fluid into said compartments.

2. The system of claim 1, wherein said device is a microfluidic device.

3. The system of claim 1, wherein said first region comprises a first channel and wherein said plurality of second regions comprises a plurality of chambers, a plurality of hydrophilic surfaces, or a plurality of hydrophobic surfaces.

4. The system of claim 3, further comprising an array of said first channels and/or an array of said plurality of second regions.

5. The system of claim 3, wherein said second layer comprises said plurality of chambers.

6. The system of claim 3, wherein said plurality of second regions comprises said plurality of hydrophilic surfaces, wherein said plurality of hydrophilic surfaces alternate with and are fluidically connected to a plurality of hydrophobic surfaces.

7. The system of claim 1, wherein said first region is one of a plurality of fluidically connected first regions, and said plurality of second regions comprises a plurality of chambers, a plurality of hydrophilic surfaces, or a plurality of hydrophobic surfaces.

8. The system of claim 7, further comprising an array of said plurality of first regions and/or an array of said plurality of second regions.

9. The system of claim 7, wherein said plurality of first regions comprises said plurality of hydrophilic surfaces, and said plurality of second regions comprises a plurality of hydrophilic surfaces, wherein the hydrophilic surfaces of the plurality of first and second regions alternate with hydrophobic surfaces.

10. The system of claim 7, wherein said plurality of first regions comprises said plurality of hydrophobic surfaces, and said plurality of second regions comprises a plurality of hydrophobic surfaces, wherein the hydrophobic surfaces of the plurality of first and second regions alternate with hydrophilic surfaces.

11. The system of claim 7, wherein said first layer further comprises a plurality of third regions alternating with said plurality of first regions.

12. The system of claim 11, wherein said plurality of first regions comprises chambers, and said plurality of third regions comprises channels connecting said chambers, wherein a cross-sectional dimension of said channel is less than a cross-sectional dimension of said chambers.

13. The system of claim 12, wherein said plurality of second regions comprises chambers.

14. The system of claim 13, wherein the second layer further comprises a plurality of fourth regions, which are chambers alternating with and not fluidically connect to the plurality of second regions, wherein the third and fourth regions are connected by the relative movement.

15. The system of claim 12, wherein said plurality of second regions comprises hydrophilic or hydrophobic surfaces, and said second layer comprises alternating hydrophobic and hydrophilic surfaces.

16. The system of claim 1, wherein said second layer further comprises a plurality of fifth regions that are not fluidically connected with the plurality of second regions, wherein a second relative movement of the first or second layers connects the compartments with the fifth regions.

17. The system of claim 16, wherein the fifth regions are fluidically connected.

18. The system of claim 17, wherein the fifth regions contain a reagent fluid.

19. The system of claim 17, wherein the second relative movement results in separation of said reagent fluid and mixture with said compartments.

20. The system of claim 17, wherein the first region is connected to one of the plurality of second regions and one of the plurality of fifth regions after the second relative movement.

21. The system of claim 1, wherein the first layer comprises a sixth region that is not fluidically connected to the first region, and the compartments are located in the second layer and wherein a second relative movement of the first or second layer connects the compartments with the sixth region.

22. The system of claim 21, wherein the sixth region contains a reagent fluid.

23. The system of claim 22, wherein the second relative movement results in separation of said reagent fluid and mixture with said compartments.

24. The system of claim 1, wherein the first layer further comprises a first plurality of chambers that are not fluidically connected to each other or to the first region, and the second layer further comprises a second plurality of chambers that are not connected to each other or the plurality of second regions, wherein, prior to the relative movement, the first region is fluidically connected to the second plurality of chambers, the relative movement results in connecting of the first plurality of chambers to the second plurality of chambers to form a second plurality of combined regions, and results in further separation of said target fluid into second compartments that are separated by an immiscible fluid and located in said second plurality of combined regions.

25. The system of claim 1, wherein said immiscible fluid is a liquid lubricant.

26. The system of claim 25, wherein said target fluid comprises an aqueous fluid.

27. The system of claim 1, wherein said plurality of second regions contains said immiscible fluid.

28. The system of claim 1, wherein said first layer and/or second layer translates longitudinally to produce said relative movement.

29. The system of claim 1, wherein said first layer and/or second layer rotates axially on the same or different axis to produce said relative movement.

30. The system of claim 1, wherein the plurality of second regions comprises a binding agent.

31. The system of claim 30, wherein the binding agent is selected from the group consisting of an antibody, an antibody fragment, an oligopeptide, a polypeptide, a nucleic acid, a cellular receptor, a ligand, an aptamer, a MHC-peptide monomer or oligomer, biotin, avidin, an oligonucleotide, a coordination complex, a synthetic polymer, a carbohydrate, a charged surface, a modified nucleic acid, a nucleic acid analog, a filter, a matrix, a polymer, a charge switch material, a gel, a membrane, a fiber, a particle, a bead, an affinity resin, an ion exchange resin, a silica-based material, a magnetic material, and a combination thereof.

32. The system of claim 31, wherein at least two of the plurality of second regions have different binding agents.

* * * * *

UNITED STATES PATENT AND TRADEMARK OFFICE
CERTIFICATE OF CORRECTION

PATENT NO. : 9,803,237 B2  
APPLICATION NO. : 13/869856  
DATED : October 31, 2017  
INVENTOR(S) : Rustem F. Ismagilov and Feng Shen It is certified that error appears in the above-identified patent and that said Letters Patent is hereby corrected as shown below:

(57) Abstract, Line 4, after "using one or more first chambers," replace "connect" with --connected--.

Signed and Sealed this  
Fifteenth Day of May, 2018

Andrei Iancu  
*Director of the United States Patent and Trademark Office*

UNITED STATES PATENT AND TRADEMARK OFFICE
CERTIFICATE OF CORRECTION

| | |
|---|---|
| PATENT NO. | : 9,803,237 B2 |
| APPLICATION NO. | : 13/869856 |
| DATED | : October 31, 2017 |
| INVENTOR(S) | : Rustem F. Ismagilov |

It is certified that error appears in the above-identified patent and that said Letters Patent is hereby corrected as shown below:

In the Specification

Column 1, Lines 13-14, "government support under Grant No." should read --government support under contract number--

Signed and Sealed this
First Day of January, 2019

Andrei Iancu
*Director of the United States Patent and Trademark Office*